US011622998B2

(12) United States Patent
Kim et al.

(10) Patent No.: US 11,622,998 B2
(45) Date of Patent: Apr. 11, 2023

(54) ANTI-INFLAMMATORY PEPTIDES AND COMPOSITION COMPRISING THE SAME

(71) Applicants: GemVax & KAEL Co., Ltd., Daejeon (KR); Sang Jae Kim, Daejon (KR)

(72) Inventors: Sang Jae Kim, Seoul (KR); Kyung Hee Kim, Seongnam-si (KR); Kyu-Yong Lee, Seongnam-si (KR); Seong-Ho Koh, Seongnam-si (KR); Hyun-Hee Park, Seongnam-si (KR); Sung Jin Huh, Seongnam-si (KR); Woo Jin Lee, Seongnam-si (KR); Bum Joon Kim, Seongnam-si (KR)

(73) Assignee: GemVax & KAEL Co., Ltd., Daejeon (KR)

(*) Notice: Subject to any disclaimer, the term of this patent is extended or adjusted under 35 U.S.C. 154(b) by 31 days.

(21) Appl. No.: 17/112,935

(22) Filed: Dec. 4, 2020

(65) Prior Publication Data

US 2021/0085757 A1    Mar. 25, 2021

Related U.S. Application Data

(62) Division of application No. 16/230,732, filed on Dec. 21, 2018, now Pat. No. 10,888,606, which is a (Continued)

(30) Foreign Application Priority Data

May 11, 2012 (KR) .................... 10-2012-0050529
May 11, 2012 (KR) .................... 10-2012-0050533
Jul. 2, 2012 (KR) .................... 10-2012-0071989
Sep. 19, 2012 (KR) .................... 10-2012-0104144
Sep. 19, 2012 (KR) .................... 10-2012-0104207

(51) Int. Cl.
A61K 38/08 (2019.01)
A61K 38/45 (2006.01)
A61K 38/00 (2006.01)
A61K 8/64 (2006.01)
C07K 7/06 (2006.01)
C07K 14/47 (2006.01)
A61Q 19/00 (2006.01)
A61P 25/00 (2006.01)
A61P 25/28 (2006.01)
C12N 9/02 (2006.01)
C07K 7/08 (2006.01)
A23L 33/18 (2016.01)

(52) U.S. Cl.
CPC .............. *A61K 38/45* (2013.01); *A23L 33/18* (2016.08); *A61K 8/64* (2013.01); *A61Q 19/00* (2013.01); *C07K 7/08* (2013.01); *C07K 14/4703* (2013.01); *C12N 9/0069* (2013.01); *C12N 9/0083* (2013.01); *C12Y 113/11* (2013.01); *C12Y 114/99001* (2013.01); *C12Y 207/07049* (2013.01); *A23V 2002/00* (2013.01); *A61K 38/00* (2013.01); *Y02A 50/30* (2018.01)

(58) Field of Classification Search
CPC .......... A61K 38/00; A61K 38/45; A61K 8/64; A61P 11/00; A61P 11/06; A61P 13/00; A61P 15/00; A61P 17/00; A61P 19/00; A61P 19/02; A61P 19/04; A61P 19/08; A61P 1/00; A61P 1/04; A61P 21/00; A61P 25/00; A61P 25/28; A61P 29/00; A61P 29/02; A61P 31/00; A61P 31/04; A61P 31/10; A61P 31/12; A61P 33/00; A61P 35/00; A61P 37/02; A61P 37/06; A61P 37/08; A61P 9/00; A61Q 19/00; C07K 14/4703; C07K 7/08; C07K 14/47
See application file for complete search history.

(56) References Cited

U.S. PATENT DOCUMENTS 7,030,211 B1    4/2006    Gaudernack et al.
7,794,723 B2    9/2010    Gaudernack et al.
(Continued)

FOREIGN PATENT DOCUMENTS

JP    2002520293 A    7/2002
KR    20110060940 A    6/2011
(Continued)

OTHER PUBLICATIONS

Dementia from Merck Manual, pp. 1-17. Accessed Jul. 29, 2009. (Year: 2009).*

(Continued)

*Primary Examiner* — Julie Ha
(74) *Attorney, Agent, or Firm* — Clark & Elbing LLP; Susan M. Michaud

(57) ABSTRACT

A peptide with anti-inflammatory activity is described, wherein the peptide comprises at least one amino acid sequence among SEQ ID NO: 2 to SEQ ID NO: 179, the peptide has above 80% homology of amino acid sequence with above-mentioned sequences, or the peptide is the fragment of the above-mentioned peptides. An inflammatory composition comprising the above mentioned peptides is also described. The peptides that have at least one amino acid sequence of SEQ ID NO: 2 to SEQ ID NO: 179 shows outstanding efficacy in both suppressing inflammation and in prophylactic means, Therefore, the composition comprising those peptides can be used as anti-inflammatory pharmaceutical compositions or as cosmetic compositions, in turn, treating and preventing a variety of different types of inflammatory diseases.

7 Claims, 160 Drawing Sheets

Specification includes a Sequence Listing.

Related U.S. Application Data division of application No. 15/354,139, filed on Nov. 17, 2016, now Pat. No. 10,206,981, which is a division of application No. 14/400,321, filed as application No. PCT/EP2013/055327 on Mar. 15, 2013, now Pat. No. 9,527,888.

(56) References Cited

U.S. PATENT DOCUMENTS

| | | | |
|---|---|---|---|
| 8,252,282 B2 | 8/2012 | Santos | |
| 9,527,888 B2 | 12/2016 | Kim et al. | |
| 9,572,900 B2 | 2/2017 | Kim | |
| 9,631,184 B2 | 4/2017 | Kim | |
| 9,757,473 B2 | 9/2017 | Kim | |
| 9,902,945 B2 | 2/2018 | Kim | |
| 10,206,981 B2 | 2/2019 | Kim et al. | |
| 2003/0100093 A1 | 5/2003 | Cech et al. | |
| 2007/0190561 A1 | 8/2007 | Morin et al. | |
| 2010/0003229 A1 | 1/2010 | Santos | |
| 2011/0150873 A1 | 6/2011 | Grainger | |
| 2011/0183925 A1 | 7/2011 | Sato et al. | |
| 2011/0318380 A1 | 12/2011 | Brix et al. | |
| 2013/0129760 A1 | 5/2013 | Gaudernack et al. | |
| 2015/0099693 A1 | 4/2015 | Kim et al. | |
| 2015/0125438 A1 | 5/2015 | Kim et al. | |
| 2015/0343095 A1* | 12/2015 | Kim | C07K 14/00 435/367 |
| 2016/0120966 A1 | 5/2016 | Kim | |
| 2017/0081376 A1 | 3/2017 | Kim et al. | |
| 2017/0112941 A1 | 4/2017 | Panitch et al. | |
| 2017/0112942 A1 | 4/2017 | Kim | |
| 2017/0275603 A1 | 9/2017 | Kim et al. | |
| 2018/0134749 A1 | 5/2018 | Kim | |

FOREIGN PATENT DOCUMENTS

| | | |
|---|---|---|
| WO | WO-0002581 A1 | 1/2000 |
| WO | WO-2009025871 A1 | 2/2009 |
| WO | WO-2011101173 A1 | 8/2011 |

OTHER PUBLICATIONS

Mattson MP, "Pathways towards and away from Alzheimer's disease," Nature, 2004, 430: 631-639. (Year: 2004).*

Perez et al., "The beta-amyloid precursor protein of Alzheimer's disease enhances neuron viability and modulates neuronal polarity," The Journal of Neuroscience, 1997, 17(24): 9407-9414. (Year: 1997).*

Schenk et al., "Immunization with amyloid-beta attenuates Alzheimer-disease-like pathology in the PDAPP mouse," Nature, 1999, 400: 173-177. (Year: 1999).*

Yampolsky et al., "The Exchangeability of Amino Acids in Proteins," Genetics, 2005, 170: 1459-1472. (Year: 2005).*

Altschul, S.F., et al., "Basic Local Alignment Search Tool," *J. Mol. Biol.* 215:403-410, Academic Press Limited, United States (1990).

Bonaldi, T., et al., "Monocytic cells hyperacetylate chromatin protein HMGB1 to redirect it towards secretion," *EMBO J.* 22(20):5551-5560, European Molecular Biology Organization, Germany (2003).

Dahlgren, K.N., et al., "Oligomeric and Fibrillar Species of Amyloid-β Peptides Differentially Affect Neuronal Viability," *J. Biol. Chem.* 277(35):32046-32053, The American Society for Biochemistry and Molecular Biology, Inc., United States (2002).

Martínez, P. and Blasco, M.A., "Telomeric and extra-telomeric roles for telomerase and the telomere-binding proteins," *Nat. Rev. Cancer* 11(3):161-176, Macmillan Publishers Limited, United Kingdom (2011).

Pearson, W.R. and Lipman, D.J., "Improved tools for biological sequence comparison," *Proc. Natl. Acad. Sci. USA* 85:2444-2448, National Academy of Science, United States (1988).

Smith, T.F. and Waterman, M.S., "Comparison of Biosequences," *Adv. Appl. Math.* 2:482-489, Academic Press, Inc., United States (1981).

Thompson, J.D., et al., "Clustal W: improving the sensitivity of progressive multiple sequence alignment through sequence weighting, position-specific gap penalties and weight matrix choice," *Nucleic Acids Res.* 22(22):4673-4680, Oxford University Press, United Kingdom (1994).

Yankner, B.A., et al., "Neurotrophic and Neurotoxic Effects of Amyloid β Protein: Reversal by Tachykinin Neuropeptides," *Science* 250(4978):279-282, American Association for the Advancement of Science, United States (1990).

International Search Report for International Patent Application No. PCT/EP2013/055327, European Patent Office, Netherlands, dated Oct. 9, 2013, 8 pages.

Written Opinion for International Patent Application No. PCT/EP2013/055327, European Patent Office, Netherlands, dated Oct. 9, 2013, 6 pages.

International Preliminary Report on Patentability for International Patent Application No. PCT/EP2013/055327, International Bureau of WIPO, Switzerland, dated Nov. 11, 2014, 7 pages.

Ko, Y.J., et al., "The Anti-Inflammatory Effect of Human Telomerase-Derived Peptide on *P. gingivalis* Lipopolysaccharide-Induced Inflammatory Cytokine Production and its Mechanism in Human Dental Pulp Cells," *Mediators of Inflammation* 2015:385127, pp. 1-8, Hindawi Publishing Corporation, Egypt (Oct. 2015).

Cho, Y.J., "A Godsend About to Arrive," GemVax (082270), Hana Daetoo Securities Co., Ltd., Company Report, 8 pages (Sep. 10, 2012).

Fonesca, S.B., et al., "Recent advances in the use of cell-penetrating peptides for medical and biological applications," *Adv. Drug Deliv. Rev.* 61(11).953-964, Elsevier B.V., Netherlands (2009).

Heitz, F., et al., "Twenty years of cell-penetrating peptides: from molecular mechanisms to therapeutics," *Br. J. Pharmacol.* 157(2):195-206, The British Pharmacological Society, United Kingdom (2009).

Lee, S-A., et al., "Heat shock protein-mediated cell penetration and cystosolic delivery of macromolecules by a telomerase-derived peptide vaccine," *Biomaterials* 34(30):7945-7505, Elsevier Ltd., United Kingdom (Jul. 2013).

Luft, R., et al., "A case of severe hypermetabolism of nonthyroid origin with a defect in the maintenance of mitochondrial respiratory control: a correlated clinical, biochemical, and morphological study," *J. Clin. Invest.* 41(9):1776-1804, American Society for Clinical Investigation, United States (1962).

Kalnins, A., et al. "Sequence of the lacZ gene of *Escherichia coli*," *The EMBO Journal* 2(4):593-597, Wiley-Blackwell, Germany (1983).

Smith, D.B. and Johnson, K.S., "Single-step purification of polypeptides expressed in *Escherichia coli* as fusions with glutathione S-transferase," *Gene* 67(1):31-40, Elsevier Science Publishers B.V., Netherlands (1988).

International Search Report for International Patent Application No. PCT/KR2013/008438, Korean Intellectual Property Office, Republic of Korea, dated Dec. 23, 2013, 3 pages.

International Preliminary Report on Patentability for International Patent Application No. PCT/KR2013/008438, The International Bureau of WIPO, Switzerland, dated Mar. 24, 2015, 5 pages.

Written Opinion for International Patent Application No. PCT/KR2013/008438, Korean Intellectual Property Office, Republic of Korea, dated Dec. 23, 2013, 5 pages.

Santos, J.H., et al., "Mitochondrial hTERT exacerbates free-radical-mediated mtDNA damage," *Aging Cell* 3(6):399-411, Wiley-Blackwell Publishing Ltd., United Kingdom (2004).

Non-Final Office Action dated Apr. 12, 2016, in U.S. Appl. No. 14/400,322, Kim, S.J., et al., filed Nov. 10, 2014.

Final Office Action dated Sep. 7, 2016, in U.S. Appl. No. 14/400,322, Kim, S.J., et al., filed Nov. 10, 2014.

Final Office Action dated Apr. 13, 2017, in U.S. Appl. No. 14/400,322, Kim, S.J., et al., filed Nov. 10, 2014.

Advisory Action dated Jul. 24, 2017, in U.S. Appl. No. 14/400,322, Kim, S.J., et al., filed Nov. 10, 2014.

Non-Final Office Action dated Apr. 16, 2018, in U.S. Appl. No. 14/400,322, Kim, S.J., et al., filed Nov. 10, 2014.

Non-Final Office Action dated Apr. 25, 2016, in U.S. Appl. No. 14/400,321, Kim, S.J., et al., filed Nov. 10, 2014.

Non-Final Office Action dated Nov. 2, 2016, in U.S. Appl. No. 14/429,637, Kim, S.J., et al., filed Mar. 19, 2015.

(56) References Cited

OTHER PUBLICATIONS

Final Office Action dated Mar. 29, 2017, in U.S. Appl. No. 14/429,637, Kim, S.J., et al., filed Mar. 19, 2015.
Advisory Action dated Jul. 5, 2017, in U.S. Appl. No. 14/429,637, Kim, S.J., et al., filed Mar. 19, 2015.
Horwich, A.L., et al., "A leader peptide is sufficient to direct mitochondrial import of a chimeric protein," *EMBO J.* 4(5): 1129-1135, Wiley-Blackwell, Germany (1985).
Armstrong, J.S., "Mitochondrial Medicine: Pharmacological Targeting of Mitochondria in Disease," *British Journal of Pharmacology* 151(8):1154-1165, Wiley-Blackwell, United Kingdom (2007).
Lopez, M., et al., "Mitochondia-targeted Nitroxides as MRI Contrast Agents and Chemotherapeutics," *Free Radical Biology & Medicine* 45(Suppl. 1):S55, Elsevier Inc., Netherlands (2008).
Salaklang, J., et al., "Superparamagnetic nanoparticles as a power systems biology characterization tool in the physiological context," *Angewandte Chemie Int. Ed.* 47(41):7857-7860, Wiley-Blackwell, United Kingdom (2008).
Non-Final Office Action dated Apr. 22, 2016, in U.S. Appl. No. 14/429,644, Kim, S.J., et al., filed Mar. 19, 2015.
Du, C., et al., "Conformational and topological requirements of cell-permeable peptide function," *J. Pept. Res.* 51(3):235-43, Springer, Germany (1998).
Schwarze, S.R., et al., "In vivo protein transduction: delivery of a biologically active protein into the mouse," *Science* 285(5433):1569-72, American Association for the Advancement of Science, United States (1999).
Ge, D., and Levicky, R., "A comparison of five bioconjugatable ferrocenes for labeling of biomolecules," *Chem. Comm. (Camb)* 46(38):7190-7192, Royal Society of Chemistry, United Kingdom (2010).

Non-Final Office Action dated Dec. 22, 2016, in U.S. Appl. No. 14/903,827, Kim, S.J., et al., filed Jan. 8, 2016.
Godet, Y., et al., "Analysis of spontaneous tumor-specific CD4 T-cell immunity in lung cancer using promiscuous HLA-DR telomerase-derived epitopes: potential synergistic effect with chemotherapy response," *Clinical Cancer Research* 18(10): 2943-2953, American Association for Cancer Research, United States (2012).
Prostatitis from Merck Manual, pp. 1-4, accessed Apr. 20, 2020.
Epididymitis and Epididymo-orchitis from Merck Manual, pp. 1-2, accessed Apr. 20, 2020.
Bacterial Urinary Tract Infections from Merck Manual, pp. 1-10, accessed Apr. 20, 2020.
List of Respiratory Diseases from Merck Manual, pp. 1-4, accessed Apr. 20, 2020.
Nonallergic rhinitis from Merck Manual, pp. 1-3, accessed Apr. 20, 2020.
Allergic rhinitis from Merck Manual, pp. 1-6, accessed Apr. 20, 2020.
Asthma from Merck Manual, pp. 1-19, accessed Apr. 20, 2020.
Cystic fibrosis from Merck Manual, pp. 1-15, accessed Apr. 20, 2020.
Coronaviruses and Acute Respiratory Syndromes (COVID-19, MERS, and SARS) from Merck Manual, pp. 1-6, accessed Apr. 20, 2020.
Weikun, "Relationship between telomerase and cell proliferation and inflammatory diseases," Foreign Medical Sciences Section of Immunology 27(3):174-177 (2004) (5 pages) (English language abstract).
Office Action dated Mar. 1, 2021 for Chinese Patent Application No. 201810794313.7, Kim et al., "Anti-inflammatory peptides and composition comprising the same," filed Mar. 15, 2013 (14 pages).
Office Action dated Mar. 1, 2021 for Chinese Patent Application No. 201810797270.8, Kim et al., "Anti-inflammatory peptides and composition comprising the same," filed Mar. 15, 2013 (13 pages).

* cited by examiner

HMGB1

HMGB1

HMGB1

HMGB1

| Pep RIA 13 (µM) | 0 | 0 | 1 | 10 | 50 |
| --- | --- | --- | --- | --- | --- |
| 20µM β-Amyloid | 0 | + | + | + | + |

HMGB1

HMGB1

HMGB1

HMGB1

HMGB1

| Pep RIA 26 (µM) | 0 | 0 | 1 | 10 | 50 |
| 20µM β-Amyloid | 0 | + | + | + | + |

HMGB1

HMGB1

HMGB1

HMGB1

HMGB1

HMGB1

HMGB1

HMGB1

| Pep RIA 83 (µM) | 0 | 0 | 1 | 10 | 50 |
|---|---|---|---|---|---|
| 20µM β-Amyloid | 0 | + | + | + | + |

HMGB1

HMGB1

HMGB1

HMGB1

HMGB1

HMGB1

HMGB1

HMGB1

HMGB1

HMGB1

HMGB1

HMGB1

HMGB1

| Pep RIA 175 (μM) | 0 | 0 | 1 | 10 | 50 |
| 20μM β-Amyloid | 0 | + | + | + | + |

HMGB1

HMGB1

SEQUENCE LISTING

```
<160> NUMBER OF SEQ ID NOS: 180

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 17
<212> TYPE: PRT
<213> ORGANISM: Homo sapiens

<400> SEQUENCE: 2

Arg Glu Ala Arg Pro Ala Leu Leu Thr Ser Arg Leu Arg Phe Ile Pro
1               5                   10                  15
```

Lys

<210> SEQ ID NO 3
<211> LENGTH: 18
<212> TYPE: PRT
<213> ORGANISM: Homo sapiens

<400> SEQUENCE: 3

His Arg Glu Ala Arg Pro Ala Leu Leu Thr Ser Arg Leu Arg Phe Ile
1               5                   10                  15

Pro Lys

<210> SEQ ID NO 4
<211> LENGTH: 19
<212> TYPE: PRT
<213> ORGANISM: Homo sapiens

<400> SEQUENCE: 4

Gln His Arg Glu Ala Arg Pro Ala Leu Leu Thr Ser Arg Leu Arg Phe
1               5                   10                  15

Ile Pro Lys

<210> SEQ ID NO 5
<211> LENGTH: 20
<212> TYPE: PRT
<213> ORGANISM: Homo sapiens

<400> SEQUENCE: 5

Arg Gln His Arg Glu Ala Arg Pro Ala Leu Leu Thr Ser Arg Leu Arg
1               5                   10                  15

Phe Ile Pro Lys
            20

<210> SEQ ID NO 6
<211> LENGTH: 21
<212> TYPE: PRT
<213> ORGANISM: Homo sapiens

<400> SEQUENCE: 6

Val Arg Gln His Arg Glu Ala Arg Pro Ala Leu Leu Thr Ser Arg Leu
1               5                   10                  15

Arg Phe Ile Pro Lys
            20

<210> SEQ ID NO 7
<211> LENGTH: 22
<212> TYPE: PRT
<213> ORGANISM: Homo sapiens

<400> SEQUENCE: 7

Glu Val Arg Gln His Arg Glu Ala Arg Pro Ala Leu Leu Thr Ser Arg
1               5                   10                  15

Leu Arg Phe Ile Pro Lys
            20

<210> SEQ ID NO 8
<211> LENGTH: 23
<212> TYPE: PRT
<213> ORGANISM: Homo sapiens

<400> SEQUENCE: 8

-continued

Ala Glu Val Arg Gln His Arg Glu Ala Arg Pro Ala Leu Leu Thr Ser
1               5                   10                  15

Arg Leu Arg Phe Ile Pro Lys
            20

<210> SEQ ID NO 9
<211> LENGTH: 24
<212> TYPE: PRT
<213> ORGANISM: Homo sapiens

<400> SEQUENCE: 9

Glu Ala Glu Val Arg Gln His Arg Glu Ala Arg Pro Ala Leu Leu Thr
1               5                   10                  15

Ser Arg Leu Arg Phe Ile Pro Lys
            20

<210> SEQ ID NO 10
<211> LENGTH: 25
<212> TYPE: PRT
<213> ORGANISM: Homo sapiens

<400> SEQUENCE: 10

Ser Glu Ala Glu Val Arg Gln His Arg Glu Ala Arg Pro Ala Leu Leu
1               5                   10                  15

Thr Ser Arg Leu Arg Phe Ile Pro Lys
            20                  25

<210> SEQ ID NO 11
<211> LENGTH: 26
<212> TYPE: PRT
<213> ORGANISM: Homo sapiens

<400> SEQUENCE: 11

Leu Ser Glu Ala Glu Val Arg Gln His Arg Glu Ala Arg Pro Ala Leu
1               5                   10                  15

Leu Thr Ser Arg Leu Arg Phe Ile Pro Lys
            20                  25

<210> SEQ ID NO 12
<211> LENGTH: 27
<212> TYPE: PRT
<213> ORGANISM: Homo sapiens

<400> SEQUENCE: 12

Glu Leu Ser Glu Ala Glu Val Arg Gln His Arg Glu Ala Arg Pro Ala
1               5                   10                  15

Leu Leu Thr Ser Arg Leu Arg Phe Ile Pro Lys
            20                  25

<210> SEQ ID NO 13
<211> LENGTH: 28
<212> TYPE: PRT
<213> ORGANISM: Homo sapiens

<400> SEQUENCE: 13

Arg Glu Leu Ser Glu Ala Glu Val Arg Gln His Arg Glu Ala Arg Pro
1               5                   10                  15

Ala Leu Leu Thr Ser Arg Leu Arg Phe Ile Pro Lys
            20                  25

<210> SEQ ID NO 14
<211> LENGTH: 29

```
<212> TYPE: PRT
<213> ORGANISM: Homo sapiens

<400> SEQUENCE: 14

Leu Arg Glu Leu Ser Glu Ala Glu Val Arg Gln His Arg Glu Ala Arg
1               5                   10                  15

Pro Ala Leu Leu Thr Ser Arg Leu Arg Phe Ile Pro Lys
            20                  25

<210> SEQ ID NO 15
<211> LENGTH: 30
<212> TYPE: PRT
<213> ORGANISM: Homo sapiens

<400> SEQUENCE: 15

Gln Leu Arg Glu Leu Ser Glu Ala Glu Val Arg Gln His Arg Glu Ala
1               5                   10                  15

Arg Pro Ala Leu Leu Thr Ser Arg Leu Arg Phe Ile Pro Lys
            20                  25                  30

<210> SEQ ID NO 16
<211> LENGTH: 18
<212> TYPE: PRT
<213> ORGANISM: Homo sapiens

<400> SEQUENCE: 16

Arg Glu Ala Arg Pro Ala Leu Leu Thr Ser Arg Leu Arg Phe Ile Pro
1               5                   10                  15

Lys Pro

<210> SEQ ID NO 17
<211> LENGTH: 19
<212> TYPE: PRT
<213> ORGANISM: Homo sapiens

<400> SEQUENCE: 17

His Arg Glu Ala Arg Pro Ala Leu Leu Thr Ser Arg Leu Arg Phe Ile
1               5                   10                  15

Pro Lys Pro

<210> SEQ ID NO 18
<211> LENGTH: 20
<212> TYPE: PRT
<213> ORGANISM: Homo sapiens

<400> SEQUENCE: 18

His Arg Glu Ala Arg Pro Ala Leu Leu Thr Ser Arg Leu Arg Phe Ile
1               5                   10                  15

Pro Lys Pro Asp
            20

<210> SEQ ID NO 19
<211> LENGTH: 19
<212> TYPE: PRT
<213> ORGANISM: Homo sapiens

<400> SEQUENCE: 19

Arg Glu Ala Arg Pro Ala Leu Leu Thr Ser Arg Leu Arg Phe Ile Pro
1               5                   10                  15

Lys Pro Asp
```

```
<210> SEQ ID NO 20
<211> LENGTH: 20
<212> TYPE: PRT
<213> ORGANISM: Homo sapiens

<400> SEQUENCE: 20

Gln His Arg Glu Ala Arg Pro Ala Leu Leu Thr Ser Arg Leu Arg Phe
1               5                   10                  15

Ile Pro Lys Pro
            20

<210> SEQ ID NO 21
<211> LENGTH: 21
<212> TYPE: PRT
<213> ORGANISM: Homo sapiens

<400> SEQUENCE: 21

Gln His Arg Glu Ala Arg Pro Ala Leu Leu Thr Ser Arg Leu Arg Phe
1               5                   10                  15

Ile Pro Lys Pro Asp
            20

<210> SEQ ID NO 22
<211> LENGTH: 22
<212> TYPE: PRT
<213> ORGANISM: Homo sapiens

<400> SEQUENCE: 22

Gln His Arg Glu Ala Arg Pro Ala Leu Leu Thr Ser Arg Leu Arg Phe
1               5                   10                  15

Ile Pro Lys Pro Asp Gly
            20

<210> SEQ ID NO 23
<211> LENGTH: 21
<212> TYPE: PRT
<213> ORGANISM: Homo sapiens

<400> SEQUENCE: 23

His Arg Glu Ala Arg Pro Ala Leu Leu Thr Ser Arg Leu Arg Phe Ile
1               5                   10                  15

Pro Lys Pro Asp Gly
            20

<210> SEQ ID NO 24
<211> LENGTH: 20
<212> TYPE: PRT
<213> ORGANISM: Homo sapiens

<400> SEQUENCE: 24

Arg Glu Ala Arg Pro Ala Leu Leu Thr Ser Arg Leu Arg Phe Ile Pro
1               5                   10                  15

Lys Pro Asp Gly
            20

<210> SEQ ID NO 25
<211> LENGTH: 21
<212> TYPE: PRT
<213> ORGANISM: Homo sapiens

<400> SEQUENCE: 25

Arg Gln His Arg Glu Ala Arg Pro Ala Leu Leu Thr Ser Arg Leu Arg
1               5                   10                  15
```

Phe Ile Pro Lys Pro
            20

<210> SEQ ID NO 26
<211> LENGTH: 22
<212> TYPE: PRT
<213> ORGANISM: Homo sapiens

<400> SEQUENCE: 26

Arg Gln His Arg Glu Ala Arg Pro Ala Leu Leu Thr Ser Arg Leu Arg
1               5                   10                  15

Phe Ile Pro Lys Pro Asp
            20

<210> SEQ ID NO 27
<211> LENGTH: 23
<212> TYPE: PRT
<213> ORGANISM: Homo sapiens

<400> SEQUENCE: 27

Arg Gln His Arg Glu Ala Arg Pro Ala Leu Leu Thr Ser Arg Leu Arg
1               5                   10                  15

Phe Ile Pro Lys Pro Asp Gly
            20

<210> SEQ ID NO 28
<211> LENGTH: 24
<212> TYPE: PRT
<213> ORGANISM: Homo sapiens

<400> SEQUENCE: 28

Arg Gln His Arg Glu Ala Arg Pro Ala Leu Leu Thr Ser Arg Leu Arg
1               5                   10                  15

Phe Ile Pro Lys Pro Asp Gly Leu
            20

<210> SEQ ID NO 29
<211> LENGTH: 23
<212> TYPE: PRT
<213> ORGANISM: Homo sapiens

<400> SEQUENCE: 29

Gln His Arg Glu Ala Arg Pro Ala Leu Leu Thr Ser Arg Leu Arg Phe
1               5                   10                  15

Ile Pro Lys Pro Asp Gly Leu
            20

<210> SEQ ID NO 30
<211> LENGTH: 22
<212> TYPE: PRT
<213> ORGANISM: Homo sapiens

<400> SEQUENCE: 30

His Arg Glu Ala Arg Pro Ala Leu Leu Thr Ser Arg Leu Arg Phe Ile
1               5                   10                  15

Pro Lys Pro Asp Gly Leu
            20

<210> SEQ ID NO 31
<211> LENGTH: 21
<212> TYPE: PRT
<213> ORGANISM: Homo sapiens

```
<400> SEQUENCE: 31

Arg Glu Ala Arg Pro Ala Leu Leu Thr Ser Arg Leu Arg Phe Ile Pro
1               5                   10                  15

Lys Pro Asp Gly Leu
            20

<210> SEQ ID NO 32
<211> LENGTH: 22
<212> TYPE: PRT
<213> ORGANISM: Homo sapiens

<400> SEQUENCE: 32

Val Arg Gln His Arg Glu Ala Arg Pro Ala Leu Leu Thr Ser Arg Leu
1               5                   10                  15

Arg Phe Ile Pro Lys Pro
            20

<210> SEQ ID NO 33
<211> LENGTH: 23
<212> TYPE: PRT
<213> ORGANISM: Homo sapiens

<400> SEQUENCE: 33

Val Arg Gln His Arg Glu Ala Arg Pro Ala Leu Leu Thr Ser Arg Leu
1               5                   10                  15

Arg Phe Ile Pro Lys Pro Asp
            20

<210> SEQ ID NO 34
<211> LENGTH: 24
<212> TYPE: PRT
<213> ORGANISM: Homo sapiens

<400> SEQUENCE: 34

Val Arg Gln His Arg Glu Ala Arg Pro Ala Leu Leu Thr Ser Arg Leu
1               5                   10                  15

Arg Phe Ile Pro Lys Pro Asp Gly
            20

<210> SEQ ID NO 35
<211> LENGTH: 25
<212> TYPE: PRT
<213> ORGANISM: Homo sapiens

<400> SEQUENCE: 35

Val Arg Gln His Arg Glu Ala Arg Pro Ala Leu Leu Thr Ser Arg Leu
1               5                   10                  15

Arg Phe Ile Pro Lys Pro Asp Gly Leu
            20                  25

<210> SEQ ID NO 36
<211> LENGTH: 26
<212> TYPE: PRT
<213> ORGANISM: Homo sapiens

<400> SEQUENCE: 36

Val Arg Gln His Arg Glu Ala Arg Pro Ala Leu Leu Thr Ser Arg Leu
1               5                   10                  15

Arg Phe Ile Pro Lys Pro Asp Gly Leu Arg
            20                  25
```

```
<210> SEQ ID NO 37
<211> LENGTH: 25
<212> TYPE: PRT
<213> ORGANISM: Homo sapiens

<400> SEQUENCE: 37

Arg Gln His Arg Glu Ala Arg Pro Ala Leu Leu Thr Ser Arg Leu Arg
1               5                   10                  15

Phe Ile Pro Lys Pro Asp Gly Leu Arg
            20                  25

<210> SEQ ID NO 38
<211> LENGTH: 24
<212> TYPE: PRT
<213> ORGANISM: Homo sapiens

<400> SEQUENCE: 38

Gln His Arg Glu Ala Arg Pro Ala Leu Leu Thr Ser Arg Leu Arg Phe
1               5                   10                  15

Ile Pro Lys Pro Asp Gly Leu Arg
            20

<210> SEQ ID NO 39
<211> LENGTH: 23
<212> TYPE: PRT
<213> ORGANISM: Homo sapiens

<400> SEQUENCE: 39

His Arg Glu Ala Arg Pro Ala Leu Leu Thr Ser Arg Leu Arg Phe Ile
1               5                   10                  15

Pro Lys Pro Asp Gly Leu Arg
            20

<210> SEQ ID NO 40
<211> LENGTH: 22
<212> TYPE: PRT
<213> ORGANISM: Homo sapiens

<400> SEQUENCE: 40

Arg Glu Ala Arg Pro Ala Leu Leu Thr Ser Arg Leu Arg Phe Ile Pro
1               5                   10                  15

Lys Pro Asp Gly Leu Arg
            20

<210> SEQ ID NO 41
<211> LENGTH: 23
<212> TYPE: PRT
<213> ORGANISM: Homo sapiens

<400> SEQUENCE: 41

Glu Val Arg Gln His Arg Glu Ala Arg Pro Ala Leu Leu Thr Ser Arg
1               5                   10                  15

Leu Arg Phe Ile Pro Lys Pro
            20

<210> SEQ ID NO 42
<211> LENGTH: 24
<212> TYPE: PRT
<213> ORGANISM: Homo sapiens

<400> SEQUENCE: 42

Glu Val Arg Gln His Arg Glu Ala Arg Pro Ala Leu Leu Thr Ser Arg
```

```
1               5                   10                  15
Leu Arg Phe Ile Pro Lys Pro Asp
            20

<210> SEQ ID NO 43
<211> LENGTH: 25
<212> TYPE: PRT
<213> ORGANISM: Homo sapiens

<400> SEQUENCE: 43

Glu Val Arg Gln His Arg Glu Ala Arg Pro Ala Leu Leu Thr Ser Arg
1               5                   10                  15

Leu Arg Phe Ile Pro Lys Pro Asp Gly
            20                  25

<210> SEQ ID NO 44
<211> LENGTH: 26
<212> TYPE: PRT
<213> ORGANISM: Homo sapiens

<400> SEQUENCE: 44

Glu Val Arg Gln His Arg Glu Ala Arg Pro Ala Leu Leu Thr Ser Arg
1               5                   10                  15

Leu Arg Phe Ile Pro Lys Pro Asp Gly Leu
            20                  25

<210> SEQ ID NO 45
<211> LENGTH: 27
<212> TYPE: PRT
<213> ORGANISM: Homo sapiens

<400> SEQUENCE: 45

Glu Val Arg Gln His Arg Glu Ala Arg Pro Ala Leu Leu Thr Ser Arg
1               5                   10                  15

Leu Arg Phe Ile Pro Lys Pro Asp Gly Leu Arg
            20                  25

<210> SEQ ID NO 46
<211> LENGTH: 28
<212> TYPE: PRT
<213> ORGANISM: Homo sapiens

<400> SEQUENCE: 46

Glu Val Arg Gln His Arg Glu Ala Arg Pro Ala Leu Leu Thr Ser Arg
1               5                   10                  15

Leu Arg Phe Ile Pro Lys Pro Asp Gly Leu Arg Pro
            20                  25

<210> SEQ ID NO 47
<211> LENGTH: 27
<212> TYPE: PRT
<213> ORGANISM: Homo sapiens

<400> SEQUENCE: 47

Val Arg Gln His Arg Glu Ala Arg Pro Ala Leu Leu Thr Ser Arg Leu
1               5                   10                  15

Arg Phe Ile Pro Lys Pro Asp Gly Leu Arg Pro
            20                  25

<210> SEQ ID NO 48
<211> LENGTH: 26
<212> TYPE: PRT
```

<213> ORGANISM: Homo sapiens

<400> SEQUENCE: 48

Arg Gln His Arg Glu Ala Arg Pro Ala Leu Leu Thr Ser Arg Leu Arg
1               5                   10                  15

Phe Ile Pro Lys Pro Asp Gly Leu Arg Pro
            20                  25

<210> SEQ ID NO 49
<211> LENGTH: 25
<212> TYPE: PRT
<213> ORGANISM: Homo sapiens

<400> SEQUENCE: 49

Gln His Arg Glu Ala Arg Pro Ala Leu Leu Thr Ser Arg Leu Arg Phe
1               5                   10                  15

Ile Pro Lys Pro Asp Gly Leu Arg Pro
            20                  25

<210> SEQ ID NO 50
<211> LENGTH: 24
<212> TYPE: PRT
<213> ORGANISM: Homo sapiens

<400> SEQUENCE: 50

His Arg Glu Ala Arg Pro Ala Leu Leu Thr Ser Arg Leu Arg Phe Ile
1               5                   10                  15

Pro Lys Pro Asp Gly Leu Arg Pro
            20

<210> SEQ ID NO 51
<211> LENGTH: 23
<212> TYPE: PRT
<213> ORGANISM: Homo sapiens

<400> SEQUENCE: 51

Arg Glu Ala Arg Pro Ala Leu Leu Thr Ser Arg Leu Arg Phe Ile Pro
1               5                   10                  15

Lys Pro Asp Gly Leu Arg Pro
            20

<210> SEQ ID NO 52
<211> LENGTH: 24
<212> TYPE: PRT
<213> ORGANISM: Homo sapiens

<400> SEQUENCE: 52

Ala Glu Val Arg Gln His Arg Glu Ala Arg Pro Ala Leu Leu Thr Ser
1               5                   10                  15

Arg Leu Arg Phe Ile Pro Lys Pro
            20

<210> SEQ ID NO 53
<211> LENGTH: 25
<212> TYPE: PRT
<213> ORGANISM: Homo sapiens

<400> SEQUENCE: 53

Ala Glu Val Arg Gln His Arg Glu Ala Arg Pro Ala Leu Leu Thr Ser
1               5                   10                  15

Arg Leu Arg Phe Ile Pro Lys Pro Asp
            20                  25

<210> SEQ ID NO 54
<211> LENGTH: 26
<212> TYPE: PRT
<213> ORGANISM: Homo sapiens

<400> SEQUENCE: 54

Ala Glu Val Arg Gln His Arg Glu Ala Arg Pro Ala Leu Leu Thr Ser
1               5                   10                  15

Arg Leu Arg Phe Ile Pro Lys Pro Asp Gly
            20                  25

<210> SEQ ID NO 55
<211> LENGTH: 27
<212> TYPE: PRT
<213> ORGANISM: Homo sapiens

<400> SEQUENCE: 55

Ala Glu Val Arg Gln His Arg Glu Ala Arg Pro Ala Leu Leu Thr Ser
1               5                   10                  15

Arg Leu Arg Phe Ile Pro Lys Pro Asp Gly Leu
            20                  25

<210> SEQ ID NO 56
<211> LENGTH: 28
<212> TYPE: PRT
<213> ORGANISM: Homo sapiens

<400> SEQUENCE: 56

Ala Glu Val Arg Gln His Arg Glu Ala Arg Pro Ala Leu Leu Thr Ser
1               5                   10                  15

Arg Leu Arg Phe Ile Pro Lys Pro Asp Gly Leu Arg
            20                  25

<210> SEQ ID NO 57
<211> LENGTH: 29
<212> TYPE: PRT
<213> ORGANISM: Homo sapiens

<400> SEQUENCE: 57

Ala Glu Val Arg Gln His Arg Glu Ala Arg Pro Ala Leu Leu Thr Ser
1               5                   10                  15

Arg Leu Arg Phe Ile Pro Lys Pro Asp Gly Leu Arg Pro
            20                  25

<210> SEQ ID NO 58
<211> LENGTH: 30
<212> TYPE: PRT
<213> ORGANISM: Homo sapiens

<400> SEQUENCE: 58

Ala Glu Val Arg Gln His Arg Glu Ala Arg Pro Ala Leu Leu Thr Ser
1               5                   10                  15

Arg Leu Arg Phe Ile Pro Lys Pro Asp Gly Leu Arg Pro Ile
            20                  25                  30

<210> SEQ ID NO 59
<211> LENGTH: 29
<212> TYPE: PRT
<213> ORGANISM: Homo sapiens

<400> SEQUENCE: 59

Glu Val Arg Gln His Arg Glu Ala Arg Pro Ala Leu Leu Thr Ser Arg
1               5                   10                  15

Leu Arg Phe Ile Pro Lys Pro Asp Gly Leu Arg Pro Ile
            20                  25

<210> SEQ ID NO 60
<211> LENGTH: 28
<212> TYPE: PRT
<213> ORGANISM: Homo sapiens

<400> SEQUENCE: 60

Val Arg Gln His Arg Glu Ala Arg Pro Ala Leu Leu Thr Ser Arg Leu
1               5                   10                  15

Arg Phe Ile Pro Lys Pro Asp Gly Leu Arg Pro Ile
            20                  25

<210> SEQ ID NO 61
<211> LENGTH: 27
<212> TYPE: PRT
<213> ORGANISM: Homo sapiens

<400> SEQUENCE: 61

Arg Gln His Arg Glu Ala Arg Pro Ala Leu Leu Thr Ser Arg Leu Arg
1               5                   10                  15

Phe Ile Pro Lys Pro Asp Gly Leu Arg Pro Ile
            20                  25

<210> SEQ ID NO 62
<211> LENGTH: 26
<212> TYPE: PRT
<213> ORGANISM: Homo sapiens

<400> SEQUENCE: 62

Gln His Arg Glu Ala Arg Pro Ala Leu Leu Thr Ser Arg Leu Arg Phe
1               5                   10                  15

Ile Pro Lys Pro Asp Gly Leu Arg Pro Ile
            20                  25

<210> SEQ ID NO 63
<211> LENGTH: 25
<212> TYPE: PRT
<213> ORGANISM: Homo sapiens

<400> SEQUENCE: 63

His Arg Glu Ala Arg Pro Ala Leu Leu Thr Ser Arg Leu Arg Phe Ile
1               5                   10                  15

Pro Lys Pro Asp Gly Leu Arg Pro Ile
            20                  25

<210> SEQ ID NO 64
<211> LENGTH: 24
<212> TYPE: PRT
<213> ORGANISM: Homo sapiens

<400> SEQUENCE: 64

Arg Glu Ala Arg Pro Ala Leu Leu Thr Ser Arg Leu Arg Phe Ile Pro
1               5                   10                  15

Lys Pro Asp Gly Leu Arg Pro Ile
            20

<210> SEQ ID NO 65
<211> LENGTH: 17

<212> TYPE: PRT
<213> ORGANISM: Homo sapiens

<400> SEQUENCE: 65

Glu Ala Arg Pro Ala Leu Leu Thr Ser Arg Leu Arg Phe Ile Pro Lys
1               5                   10                  15

Pro

<210> SEQ ID NO 66
<211> LENGTH: 18
<212> TYPE: PRT
<213> ORGANISM: Homo sapiens

<400> SEQUENCE: 66

Glu Ala Arg Pro Ala Leu Leu Thr Ser Arg Leu Arg Phe Ile Pro Lys
1               5                   10                  15

Pro Asp

<210> SEQ ID NO 67
<211> LENGTH: 19
<212> TYPE: PRT
<213> ORGANISM: Homo sapiens

<400> SEQUENCE: 67

Glu Ala Arg Pro Ala Leu Leu Thr Ser Arg Leu Arg Phe Ile Pro Lys
1               5                   10                  15

Pro Asp Gly

<210> SEQ ID NO 68
<211> LENGTH: 21
<212> TYPE: PRT
<213> ORGANISM: Homo sapiens

<400> SEQUENCE: 68

Glu Ala Arg Pro Ala Leu Leu Thr Ser Arg Leu Arg Phe Ile Pro Lys
1               5                   10                  15

Pro Asp Gly Leu Arg
            20

<210> SEQ ID NO 69
<211> LENGTH: 22
<212> TYPE: PRT
<213> ORGANISM: Homo sapiens

<400> SEQUENCE: 69

Glu Ala Arg Pro Ala Leu Leu Thr Ser Arg Leu Arg Phe Ile Pro Lys
1               5                   10                  15

Pro Asp Gly Leu Arg Pro
            20

<210> SEQ ID NO 70
<211> LENGTH: 23
<212> TYPE: PRT
<213> ORGANISM: Homo sapiens

<400> SEQUENCE: 70

Glu Ala Arg Pro Ala Leu Leu Thr Ser Arg Leu Arg Phe Ile Pro Lys
1               5                   10                  15

Pro Asp Gly Leu Arg Pro Ile
            20

```
<210> SEQ ID NO 71
<211> LENGTH: 24
<212> TYPE: PRT
<213> ORGANISM: Homo sapiens

<400> SEQUENCE: 71

Glu Ala Arg Pro Ala Leu Leu Thr Ser Arg Leu Arg Phe Ile Pro Lys
1               5                   10                  15

Pro Asp Gly Leu Arg Pro Ile Val
            20

<210> SEQ ID NO 72
<211> LENGTH: 25
<212> TYPE: PRT
<213> ORGANISM: Homo sapiens

<400> SEQUENCE: 72

Glu Ala Arg Pro Ala Leu Leu Thr Ser Arg Leu Arg Phe Ile Pro Lys
1               5                   10                  15

Pro Asp Gly Leu Arg Pro Ile Val Asn
            20                  25

<210> SEQ ID NO 73
<211> LENGTH: 26
<212> TYPE: PRT
<213> ORGANISM: Homo sapiens

<400> SEQUENCE: 73

Glu Ala Arg Pro Ala Leu Leu Thr Ser Arg Leu Arg Phe Ile Pro Lys
1               5                   10                  15

Pro Asp Gly Leu Arg Pro Ile Val Asn Met
            20                  25

<210> SEQ ID NO 74
<211> LENGTH: 27
<212> TYPE: PRT
<213> ORGANISM: Homo sapiens

<400> SEQUENCE: 74

Glu Ala Arg Pro Ala Leu Leu Thr Ser Arg Leu Arg Phe Ile Pro Lys
1               5                   10                  15

Pro Asp Gly Leu Arg Pro Ile Val Asn Met Asp
            20                  25

<210> SEQ ID NO 75
<211> LENGTH: 28
<212> TYPE: PRT
<213> ORGANISM: Homo sapiens

<400> SEQUENCE: 75

Glu Ala Arg Pro Ala Leu Leu Thr Ser Arg Leu Arg Phe Ile Pro Lys
1               5                   10                  15

Pro Asp Gly Leu Arg Pro Ile Val Asn Met Asp Tyr
            20                  25

<210> SEQ ID NO 76
<211> LENGTH: 29
<212> TYPE: PRT
<213> ORGANISM: Homo sapiens

<400> SEQUENCE: 76

Glu Ala Arg Pro Ala Leu Leu Thr Ser Arg Leu Arg Phe Ile Pro Lys
1               5                   10                  15
```

Pro Asp Gly Leu Arg Pro Ile Val Asn Met Asp Tyr Val
            20                  25

<210> SEQ ID NO 77
<211> LENGTH: 30
<212> TYPE: PRT
<213> ORGANISM: Homo sapiens

<400> SEQUENCE: 77

Glu Ala Arg Pro Ala Leu Leu Thr Ser Arg Leu Arg Phe Ile Pro Lys
1               5                   10                  15

Pro Asp Gly Leu Arg Pro Ile Val Asn Met Asp Tyr Val Val
            20                  25                  30

<210> SEQ ID NO 78
<211> LENGTH: 15
<212> TYPE: PRT
<213> ORGANISM: Homo sapiens

<400> SEQUENCE: 78

Glu Ala Arg Pro Ala Leu Leu Thr Ser Arg Leu Arg Phe Ile Pro
1               5                   10                  15

<210> SEQ ID NO 79
<211> LENGTH: 14
<212> TYPE: PRT
<213> ORGANISM: Homo sapiens

<400> SEQUENCE: 79

Glu Ala Arg Pro Ala Leu Leu Thr Ser Arg Leu Arg Phe Ile
1               5                   10

<210> SEQ ID NO 80
<211> LENGTH: 13
<212> TYPE: PRT
<213> ORGANISM: Homo sapiens

<400> SEQUENCE: 80

Glu Ala Arg Pro Ala Leu Leu Thr Ser Arg Leu Arg Phe
1               5                   10

<210> SEQ ID NO 81
<211> LENGTH: 12
<212> TYPE: PRT
<213> ORGANISM: Homo sapiens

<400> SEQUENCE: 81

Glu Ala Arg Pro Ala Leu Leu Thr Ser Arg Leu Arg
1               5                   10

<210> SEQ ID NO 82
<211> LENGTH: 11
<212> TYPE: PRT
<213> ORGANISM: Homo sapiens

<400> SEQUENCE: 82

Glu Ala Arg Pro Ala Leu Leu Thr Ser Arg Leu
1               5                   10

<210> SEQ ID NO 83
<211> LENGTH: 10
<212> TYPE: PRT
<213> ORGANISM: Homo sapiens

```
<400> SEQUENCE: 83

Glu Ala Arg Pro Ala Leu Leu Thr Ser Arg
1               5                   10

<210> SEQ ID NO 84
<211> LENGTH: 9
<212> TYPE: PRT
<213> ORGANISM: Homo sapiens

<400> SEQUENCE: 84

Glu Ala Arg Pro Ala Leu Leu Thr Ser
1               5

<210> SEQ ID NO 85
<211> LENGTH: 8
<212> TYPE: PRT
<213> ORGANISM: Homo sapiens

<400> SEQUENCE: 85

Glu Ala Arg Pro Ala Leu Leu Thr
1               5

<210> SEQ ID NO 86
<211> LENGTH: 7
<212> TYPE: PRT
<213> ORGANISM: Homo sapiens

<400> SEQUENCE: 86

Glu Ala Arg Pro Ala Leu Leu
1               5

<210> SEQ ID NO 87
<211> LENGTH: 6
<212> TYPE: PRT
<213> ORGANISM: Homo sapiens

<400> SEQUENCE: 87

Glu Ala Arg Pro Ala Leu
1               5

<210> SEQ ID NO 88
<211> LENGTH: 5
<212> TYPE: PRT
<213> ORGANISM: Homo sapiens

<400> SEQUENCE: 88

Glu Ala Arg Pro Ala
1               5

<210> SEQ ID NO 89
<211> LENGTH: 4
<212> TYPE: PRT
<213> ORGANISM: Homo sapiens

<400> SEQUENCE: 89

Glu Ala Arg Pro
1

<210> SEQ ID NO 90
<211> LENGTH: 3
<212> TYPE: PRT
<213> ORGANISM: Homo sapiens

<400> SEQUENCE: 90
```

Glu Ala Arg
1

<210> SEQ ID NO 91
<211> LENGTH: 15
<212> TYPE: PRT
<213> ORGANISM: Homo sapiens

<400> SEQUENCE: 91

Ala Arg Pro Ala Leu Leu Thr Ser Arg Leu Arg Phe Ile Pro Lys
1               5                   10                  15

<210> SEQ ID NO 92
<211> LENGTH: 14
<212> TYPE: PRT
<213> ORGANISM: Homo sapiens

<400> SEQUENCE: 92

Arg Pro Ala Leu Leu Thr Ser Arg Leu Arg Phe Ile Pro Lys
1               5                   10

<210> SEQ ID NO 93
<211> LENGTH: 13
<212> TYPE: PRT
<213> ORGANISM: Homo sapiens

<400> SEQUENCE: 93

Pro Ala Leu Leu Thr Ser Arg Leu Arg Phe Ile Pro Lys
1               5                   10

<210> SEQ ID NO 94
<211> LENGTH: 12
<212> TYPE: PRT
<213> ORGANISM: Homo sapiens

<400> SEQUENCE: 94

Ala Leu Leu Thr Ser Arg Leu Arg Phe Ile Pro Lys
1               5                   10

<210> SEQ ID NO 95
<211> LENGTH: 11
<212> TYPE: PRT
<213> ORGANISM: Homo sapiens

<400> SEQUENCE: 95

Leu Leu Thr Ser Arg Leu Arg Phe Ile Pro Lys
1               5                   10

<210> SEQ ID NO 96
<211> LENGTH: 10
<212> TYPE: PRT
<213> ORGANISM: Homo sapiens

<400> SEQUENCE: 96

Leu Thr Ser Arg Leu Arg Phe Ile Pro Lys
1               5                   10

<210> SEQ ID NO 97
<211> LENGTH: 9
<212> TYPE: PRT
<213> ORGANISM: Homo sapiens

<400> SEQUENCE: 97

Thr Ser Arg Leu Arg Phe Ile Pro Lys
1               5

```
<210> SEQ ID NO 98
<211> LENGTH: 8
<212> TYPE: PRT
<213> ORGANISM: Homo sapiens

<400> SEQUENCE: 98

Ser Arg Leu Arg Phe Ile Pro Lys
1               5

<210> SEQ ID NO 99
<211> LENGTH: 7
<212> TYPE: PRT
<213> ORGANISM: Homo sapiens

<400> SEQUENCE: 99

Arg Leu Arg Phe Ile Pro Lys
1               5

<210> SEQ ID NO 100
<211> LENGTH: 6
<212> TYPE: PRT
<213> ORGANISM: Homo sapiens

<400> SEQUENCE: 100

Leu Arg Phe Ile Pro Lys
1               5

<210> SEQ ID NO 101
<211> LENGTH: 5
<212> TYPE: PRT
<213> ORGANISM: Homo sapiens

<400> SEQUENCE: 101

Arg Phe Ile Pro Lys
1               5

<210> SEQ ID NO 102
<211> LENGTH: 4
<212> TYPE: PRT
<213> ORGANISM: Homo sapiens

<400> SEQUENCE: 102

Phe Ile Pro Lys
1

<210> SEQ ID NO 103
<211> LENGTH: 3
<212> TYPE: PRT
<213> ORGANISM: Homo sapiens

<400> SEQUENCE: 103

Ile Pro Lys
1

<210> SEQ ID NO 104
<211> LENGTH: 14
<212> TYPE: PRT
<213> ORGANISM: Homo sapiens

<400> SEQUENCE: 104

Ala Arg Pro Ala Leu Leu Thr Ser Arg Leu Arg Phe Ile Pro
1               5                   10
```

```
<210> SEQ ID NO 105
<211> LENGTH: 12
<212> TYPE: PRT
<213> ORGANISM: Homo sapiens

<400> SEQUENCE: 105

Arg Pro Ala Leu Leu Thr Ser Arg Leu Arg Phe Ile
1               5                   10

<210> SEQ ID NO 106
<211> LENGTH: 10
<212> TYPE: PRT
<213> ORGANISM: Homo sapiens

<400> SEQUENCE: 106

Pro Ala Leu Leu Thr Ser Arg Leu Arg Phe
1               5                   10

<210> SEQ ID NO 107
<211> LENGTH: 8
<212> TYPE: PRT
<213> ORGANISM: Homo sapiens

<400> SEQUENCE: 107

Ala Leu Leu Thr Ser Arg Leu Arg
1               5

<210> SEQ ID NO 108
<211> LENGTH: 6
<212> TYPE: PRT
<213> ORGANISM: Homo sapiens

<400> SEQUENCE: 108

Leu Leu Thr Ser Arg Leu
1               5

<210> SEQ ID NO 109
<211> LENGTH: 4
<212> TYPE: PRT
<213> ORGANISM: Homo sapiens

<400> SEQUENCE: 109

Leu Thr Ser Arg
1

<210> SEQ ID NO 110
<211> LENGTH: 13
<212> TYPE: PRT
<213> ORGANISM: Homo sapiens

<400> SEQUENCE: 110

Ala Arg Pro Ala Leu Leu Thr Ser Arg Leu Arg Phe Ile
1               5                   10

<210> SEQ ID NO 111
<211> LENGTH: 12
<212> TYPE: PRT
<213> ORGANISM: Homo sapiens

<400> SEQUENCE: 111

Ala Arg Pro Ala Leu Leu Thr Ser Arg Leu Arg Phe
1               5                   10

<210> SEQ ID NO 112
<211> LENGTH: 11
```

<212> TYPE: PRT
<213> ORGANISM: Homo sapiens

<400> SEQUENCE: 112

Ala Arg Pro Ala Leu Leu Thr Ser Arg Leu Arg
1               5                   10

<210> SEQ ID NO 113
<211> LENGTH: 10
<212> TYPE: PRT
<213> ORGANISM: Homo sapiens

<400> SEQUENCE: 113

Ala Arg Pro Ala Leu Leu Thr Ser Arg Leu
1               5                   10

<210> SEQ ID NO 114
<211> LENGTH: 9
<212> TYPE: PRT
<213> ORGANISM: Homo sapiens

<400> SEQUENCE: 114

Ala Arg Pro Ala Leu Leu Thr Ser Arg
1               5

<210> SEQ ID NO 115
<211> LENGTH: 8
<212> TYPE: PRT
<213> ORGANISM: Homo sapiens

<400> SEQUENCE: 115

Ala Arg Pro Ala Leu Leu Thr Ser
1               5

<210> SEQ ID NO 116
<211> LENGTH: 7
<212> TYPE: PRT
<213> ORGANISM: Homo sapiens

<400> SEQUENCE: 116

Ala Arg Pro Ala Leu Leu Thr
1               5

<210> SEQ ID NO 117
<211> LENGTH: 6
<212> TYPE: PRT
<213> ORGANISM: Homo sapiens

<400> SEQUENCE: 117

Ala Arg Pro Ala Leu Leu
1               5

<210> SEQ ID NO 118
<211> LENGTH: 5
<212> TYPE: PRT
<213> ORGANISM: Homo sapiens

<400> SEQUENCE: 118

Ala Arg Pro Ala Leu
1               5

<210> SEQ ID NO 119
<211> LENGTH: 4
<212> TYPE: PRT
<213> ORGANISM: Homo sapiens

<400> SEQUENCE: 119

Ala Arg Pro Ala
1

<210> SEQ ID NO 120
<211> LENGTH: 3
<212> TYPE: PRT
<213> ORGANISM: Homo sapiens

<400> SEQUENCE: 120

Ala Arg Pro
1

<210> SEQ ID NO 121
<211> LENGTH: 13
<212> TYPE: PRT
<213> ORGANISM: Homo sapiens

<400> SEQUENCE: 121

Arg Pro Ala Leu Leu Thr Ser Arg Leu Arg Phe Ile Pro
1               5                   10

<210> SEQ ID NO 122
<211> LENGTH: 11
<212> TYPE: PRT
<213> ORGANISM: Homo sapiens

<400> SEQUENCE: 122

Arg Pro Ala Leu Leu Thr Ser Arg Leu Arg Phe
1               5                   10

<210> SEQ ID NO 123
<211> LENGTH: 10
<212> TYPE: PRT
<213> ORGANISM: Homo sapiens

<400> SEQUENCE: 123

Arg Pro Ala Leu Leu Thr Ser Arg Leu Arg
1               5                   10

<210> SEQ ID NO 124
<211> LENGTH: 8
<212> TYPE: PRT
<213> ORGANISM: Homo sapiens

<400> SEQUENCE: 124

Arg Pro Ala Leu Leu Thr Ser Arg
1               5

<210> SEQ ID NO 125
<211> LENGTH: 7
<212> TYPE: PRT
<213> ORGANISM: Homo sapiens

<400> SEQUENCE: 125

Arg Pro Ala Leu Leu Thr Ser
1               5

<210> SEQ ID NO 126
<211> LENGTH: 6
<212> TYPE: PRT
<213> ORGANISM: Homo sapiens

<400> SEQUENCE: 126

Arg Pro Ala Leu Leu Thr
1               5

<210> SEQ ID NO 127
<211> LENGTH: 5
<212> TYPE: PRT
<213> ORGANISM: Homo sapiens

<400> SEQUENCE: 127

Arg Pro Ala Leu Leu
1               5

<210> SEQ ID NO 128
<211> LENGTH: 4
<212> TYPE: PRT
<213> ORGANISM: Homo sapiens

<400> SEQUENCE: 128

Arg Pro Ala Leu
1

<210> SEQ ID NO 129
<211> LENGTH: 3
<212> TYPE: PRT
<213> ORGANISM: Homo sapiens

<400> SEQUENCE: 129

Arg Pro Ala
1

<210> SEQ ID NO 130
<211> LENGTH: 12
<212> TYPE: PRT
<213> ORGANISM: Homo sapiens

<400> SEQUENCE: 130

Pro Ala Leu Leu Thr Ser Arg Leu Arg Phe Ile Pro
1               5                   10

<210> SEQ ID NO 131
<211> LENGTH: 11
<212> TYPE: PRT
<213> ORGANISM: Homo sapiens

<400> SEQUENCE: 131

Pro Ala Leu Leu Thr Ser Arg Leu Arg Phe Ile
1               5                   10

<210> SEQ ID NO 132
<211> LENGTH: 9
<212> TYPE: PRT
<213> ORGANISM: Homo sapiens

<400> SEQUENCE: 132

Pro Ala Leu Leu Thr Ser Arg Leu Arg
1               5

<210> SEQ ID NO 133
<211> LENGTH: 8
<212> TYPE: PRT
<213> ORGANISM: Homo sapiens

<400> SEQUENCE: 133

Pro Ala Leu Leu Thr Ser Arg Leu

```
1               5
```

<210> SEQ ID NO 134
<211> LENGTH: 7
<212> TYPE: PRT
<213> ORGANISM: Homo sapiens

<400> SEQUENCE: 134

```
Pro Ala Leu Leu Thr Ser Arg
1               5
```

<210> SEQ ID NO 135
<211> LENGTH: 6
<212> TYPE: PRT
<213> ORGANISM: Homo sapiens

<400> SEQUENCE: 135

```
Pro Ala Leu Leu Thr Ser
1               5
```

<210> SEQ ID NO 136
<211> LENGTH: 5
<212> TYPE: PRT
<213> ORGANISM: Homo sapiens

<400> SEQUENCE: 136

```
Pro Ala Leu Leu Thr
1               5
```

<210> SEQ ID NO 137
<211> LENGTH: 4
<212> TYPE: PRT
<213> ORGANISM: Homo sapiens

<400> SEQUENCE: 137

```
Pro Ala Leu Leu
1
```

<210> SEQ ID NO 138
<211> LENGTH: 3
<212> TYPE: PRT
<213> ORGANISM: Homo sapiens

<400> SEQUENCE: 138

```
Pro Ala Leu
1
```

<210> SEQ ID NO 139
<211> LENGTH: 11
<212> TYPE: PRT
<213> ORGANISM: Homo sapiens

<400> SEQUENCE: 139

```
Ala Leu Leu Thr Ser Arg Leu Arg Phe Ile Pro
1               5                   10
```

<210> SEQ ID NO 140
<211> LENGTH: 9
<212> TYPE: PRT
<213> ORGANISM: Homo sapiens

<400> SEQUENCE: 140

```
Ala Leu Leu Thr Ser Arg Leu Arg Phe
1               5
```

```
<210> SEQ ID NO 141
<211> LENGTH: 7
<212> TYPE: PRT
<213> ORGANISM: Homo sapiens

<400> SEQUENCE: 141

Ala Leu Leu Thr Ser Arg Leu
1               5

<210> SEQ ID NO 142
<211> LENGTH: 6
<212> TYPE: PRT
<213> ORGANISM: Homo sapiens

<400> SEQUENCE: 142

Ala Leu Leu Thr Ser Arg
1               5

<210> SEQ ID NO 143
<211> LENGTH: 5
<212> TYPE: PRT
<213> ORGANISM: Homo sapiens

<400> SEQUENCE: 143

Ala Leu Leu Thr Ser
1               5

<210> SEQ ID NO 144
<211> LENGTH: 4
<212> TYPE: PRT
<213> ORGANISM: Homo sapiens

<400> SEQUENCE: 144

Ala Leu Leu Thr
1

<210> SEQ ID NO 145
<211> LENGTH: 3
<212> TYPE: PRT
<213> ORGANISM: Homo sapiens

<400> SEQUENCE: 145

Ala Leu Leu
1

<210> SEQ ID NO 146
<211> LENGTH: 10
<212> TYPE: PRT
<213> ORGANISM: Homo sapiens

<400> SEQUENCE: 146

Leu Leu Thr Ser Arg Leu Arg Phe Ile Pro
1               5                   10

<210> SEQ ID NO 147
<211> LENGTH: 9
<212> TYPE: PRT
<213> ORGANISM: Homo sapiens

<400> SEQUENCE: 147

Leu Leu Thr Ser Arg Leu Arg Phe Ile
1               5

<210> SEQ ID NO 148
```

```
<211> LENGTH: 8
<212> TYPE: PRT
<213> ORGANISM: Homo sapiens

<400> SEQUENCE: 148

Leu Leu Thr Ser Arg Leu Arg Phe
1               5

<210> SEQ ID NO 149
<211> LENGTH: 7
<212> TYPE: PRT
<213> ORGANISM: Homo sapiens

<400> SEQUENCE: 149

Leu Leu Thr Ser Arg Leu Arg
1               5

<210> SEQ ID NO 150
<211> LENGTH: 5
<212> TYPE: PRT
<213> ORGANISM: Homo sapiens

<400> SEQUENCE: 150

Leu Leu Thr Ser Arg
1               5

<210> SEQ ID NO 151
<211> LENGTH: 4
<212> TYPE: PRT
<213> ORGANISM: Homo sapiens

<400> SEQUENCE: 151

Leu Leu Thr Ser
1

<210> SEQ ID NO 152
<211> LENGTH: 3
<212> TYPE: PRT
<213> ORGANISM: Homo sapiens

<400> SEQUENCE: 152

Leu Leu Thr
1

<210> SEQ ID NO 153
<211> LENGTH: 9
<212> TYPE: PRT
<213> ORGANISM: Homo sapiens

<400> SEQUENCE: 153

Leu Thr Ser Arg Leu Arg Phe Ile Pro
1               5

<210> SEQ ID NO 154
<211> LENGTH: 8
<212> TYPE: PRT
<213> ORGANISM: Homo sapiens

<400> SEQUENCE: 154

Leu Thr Ser Arg Leu Arg Phe Ile
1               5

<210> SEQ ID NO 155
<211> LENGTH: 7
<212> TYPE: PRT
```

<213> ORGANISM: Homo sapiens

<400> SEQUENCE: 155

Leu Thr Ser Arg Leu Arg Phe
1               5

<210> SEQ ID NO 156
<211> LENGTH: 6
<212> TYPE: PRT
<213> ORGANISM: Homo sapiens

<400> SEQUENCE: 156

Leu Thr Ser Arg Leu Arg
1               5

<210> SEQ ID NO 157
<211> LENGTH: 5
<212> TYPE: PRT
<213> ORGANISM: Homo sapiens

<400> SEQUENCE: 157

Leu Thr Ser Arg Leu
1               5

<210> SEQ ID NO 158
<211> LENGTH: 3
<212> TYPE: PRT
<213> ORGANISM: Homo sapiens

<400> SEQUENCE: 158

Leu Thr Ser
1

<210> SEQ ID NO 159
<211> LENGTH: 8
<212> TYPE: PRT
<213> ORGANISM: Homo sapiens

<400> SEQUENCE: 159

Thr Ser Arg Leu Arg Phe Ile Pro
1               5

<210> SEQ ID NO 160
<211> LENGTH: 7
<212> TYPE: PRT
<213> ORGANISM: Homo sapiens

<400> SEQUENCE: 160

Thr Ser Arg Leu Arg Phe Ile
1               5

<210> SEQ ID NO 161
<211> LENGTH: 6
<212> TYPE: PRT
<213> ORGANISM: Homo sapiens

<400> SEQUENCE: 161

Thr Ser Arg Leu Arg Phe
1               5

<210> SEQ ID NO 162
<211> LENGTH: 5
<212> TYPE: PRT
<213> ORGANISM: Homo sapiens

```
<400> SEQUENCE: 162

Thr Ser Arg Leu Arg
1               5

<210> SEQ ID NO 163
<211> LENGTH: 4
<212> TYPE: PRT
<213> ORGANISM: Homo sapiens

<400> SEQUENCE: 163

Thr Ser Arg Leu
1

<210> SEQ ID NO 164
<211> LENGTH: 3
<212> TYPE: PRT
<213> ORGANISM: Homo sapiens

<400> SEQUENCE: 164

Thr Ser Arg
1

<210> SEQ ID NO 165
<211> LENGTH: 7
<212> TYPE: PRT
<213> ORGANISM: Homo sapiens

<400> SEQUENCE: 165

Ser Arg Leu Arg Phe Ile Pro
1               5

<210> SEQ ID NO 166
<211> LENGTH: 6
<212> TYPE: PRT
<213> ORGANISM: Homo sapiens

<400> SEQUENCE: 166

Ser Arg Leu Arg Phe Ile
1               5

<210> SEQ ID NO 167
<211> LENGTH: 5
<212> TYPE: PRT
<213> ORGANISM: Homo sapiens

<400> SEQUENCE: 167

Ser Arg Leu Arg Phe
1               5

<210> SEQ ID NO 168
<211> LENGTH: 4
<212> TYPE: PRT
<213> ORGANISM: Homo sapiens

<400> SEQUENCE: 168

Ser Arg Leu Arg
1

<210> SEQ ID NO 169
<211> LENGTH: 3
<212> TYPE: PRT
<213> ORGANISM: Homo sapiens

<400> SEQUENCE: 169
```

Ser Arg Leu
1

<210> SEQ ID NO 170
<211> LENGTH: 6
<212> TYPE: PRT
<213> ORGANISM: Homo sapiens

<400> SEQUENCE: 170

Arg Leu Arg Phe Ile Pro
1               5

<210> SEQ ID NO 171
<211> LENGTH: 5
<212> TYPE: PRT
<213> ORGANISM: Homo sapiens

<400> SEQUENCE: 171

Arg Leu Arg Phe Ile
1               5

<210> SEQ ID NO 172
<211> LENGTH: 4
<212> TYPE: PRT
<213> ORGANISM: Homo sapiens

<400> SEQUENCE: 172

Arg Leu Arg Phe
1

<210> SEQ ID NO 173
<211> LENGTH: 3
<212> TYPE: PRT
<213> ORGANISM: Homo sapiens

<400> SEQUENCE: 173

Arg Leu Arg
1

<210> SEQ ID NO 174
<211> LENGTH: 5
<212> TYPE: PRT
<213> ORGANISM: Homo sapiens

<400> SEQUENCE: 174

Leu Arg Phe Ile Pro
1               5

<210> SEQ ID NO 175
<211> LENGTH: 4
<212> TYPE: PRT
<213> ORGANISM: Homo sapiens

<400> SEQUENCE: 175

Leu Arg Phe Ile
1

<210> SEQ ID NO 176
<211> LENGTH: 3
<212> TYPE: PRT
<213> ORGANISM: Homo sapiens

<400> SEQUENCE: 176

Leu Arg Phe
1

<210> SEQ ID NO 177
<211> LENGTH: 4
<212> TYPE: PRT
<213> ORGANISM: Homo sapiens

<400> SEQUENCE: 177

Arg Phe Ile Pro
1

<210> SEQ ID NO 178
<211> LENGTH: 3
<212> TYPE: PRT
<213> ORGANISM: Homo sapiens

<400> SEQUENCE: 178

Arg Phe Ile
1

<210> SEQ ID NO 179
<211> LENGTH: 3
<212> TYPE: PRT
<213> ORGANISM: Homo sapiens

<400> SEQUENCE: 179

Phe Ile Pro
1

<210> SEQ ID NO 180
<211> LENGTH: 1132
<212> TYPE: PRT
<213> ORGANISM: Homo sapiens

<400> SEQUENCE: 180

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg

```
            195                 200                 205
Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu
        435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
610                 615                 620
```

-continued

```
Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
            645                 650                 655

Arg Val Lys Ala Leu Phe Ser Val Leu Asn Tyr Glu Arg Ala Arg Arg
        660                 665                 670

Pro Gly Leu Leu Gly Ala Ser Val Gly Leu Asp Asp Ile His Arg
    675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035
```

-continued

```
Thr Ala  Ser Leu Cys Tyr Ser  Ile Leu Lys Ala Lys  Asn Ala Gly
    1040             1045             1050

Met Ser  Leu Gly Ala Lys Gly  Ala Ala Gly Pro Leu  Pro Ser Glu
    1055             1060             1065

Ala Val  Gln Trp Leu Cys His  Gln Ala Phe Leu Leu  Lys Leu Thr
    1070             1075             1080

Arg His  Arg Val Thr Tyr Val  Pro Leu Leu Gly Ser  Leu Arg Thr
    1085             1090             1095

Ala Gln  Thr Gln Leu Ser Arg  Lys Leu Pro Gly Thr  Thr Leu Thr
    1100             1105             1110

Ala Leu  Glu Ala Ala Ala Asn  Pro Ala Leu Pro Ser  Asp Phe Lys
    1115             1120             1125

Thr Ile  Leu Asp
    1130
```

ANTI-INFLAMMATORY PEPTIDES AND COMPOSITION COMPRISING THE SAME

PRIORITY

This application is a divisional patent application of U.S. application Ser. No. 16/230,732, filed on Dec. 21, 2018, which is a divisional of U.S. application Ser. No. 15/354, 139, filed on Nov. 17, 2016, now U.S. Pat. No. 10,206,981 B2, which is a divisional application of U.S. application Ser. No. 14/400,321, filed on Mar. 2, 2015 under 35 U.S.C. § 371, now U.S. Pat. No. 9,527,888 B2, which is based on International PCT Application PCT/EP2013/055327, filed on Mar. 15, 2013, which claims priority to Korean Patent Application Nos. 10-2012-0050529, filed May 11, 2012; 10-2012-0050533, filed May 11, 2012; 10-2012-0071989, filed Jul. 2, 2012; 10-2012-0104144, filed Sep. 19, 2012; and 10-2012-0104207, filed Sep. 19, 2012, the disclosures of which are herein incorporated by reference in their entireties.

REFERENCE TO SEQUENCE LISTING SUBMITTED ELECTRONICALLY VIA EFS-WEB

The instant application contains a sequence listing which has been submitted electronically in ASCII format and is hereby incorporated by reference in its entirety (said ASCII copy, created on Dec. 3, 2020, is named 2473_0750009_SeqListing_ST25.txt and is 45,733 bytes in size).

FIELD OF THE INVENTION

The present invention relates to anti-inflammatory peptides and compositions comprising the same.

BACKGROUND OF THE INVENTION

Inflammation is a type of biological defense as a means of protecting the body from damage of biological tissues that could be caused by external physical stimuli, chemical stimuli such as exposure to various allergens, or invasion of microorganisms including bacteria, fungi and viruses.

The Cyclooxygenase (COX) pathway or Lipoxygenase (LOX) Pathway can used for signaling inflammation, which produce prostaglandin, thromboxane, etc. Once the Inflammatory signal is delivered, one of many changes that happen in the body is the expansion of the blood vessel for increased blood supply around the inflammation to concentrate blood cells such as neutrophils required for the Inflammatory response. However, inflammatory diseases can result if an abnormal biological defense response occurs excessively. To prevent from this, drugs that suppress excessive inflammatory response by repressing enzymes used in inflammatory signaling pathway (for example, COX-1, COX-2, 5-LOX, 12-LOX etc.) are under development.

According to response time, inflammation is categorized as acute inflammation (immediate response, non-specific response, several days to several weeks), chronic inflammation (delayed response, specific response, several weeks or more), subacute inflammation (a middle stage in between acute inflammation and chronic inflammation, characteristics of mixed product of mononuclear and polymorphounuclear).

Also, aside from peptide factors, factors such as prostaglandin, leukotriene, lipid factors including platelet activating factor (PAF), synthetic enzyme of inflammation factor, free radical such as NO (nitric oxide), many kinds of cell adhesion molecule, immune system, and coagulation factors can cause inflammation.

Once a cell is damaged due to the known causative agents of Inflammation such as external biological factors (microbes, viruses, parasites), physical factors (mechanical stimuli, heat, radiation, electricity), and chemical factors, histamine and kinin are released. The released histamine and kinin will result in anglectasis, increased capillary permeability and concentration of macrophages at the inflammation site, and it causes increased blood flow rate, edema, immunocyte and antibody migration, pain and heat generation.

Currently used treatments for inflammation are synthetic drugs such as ibuprofen, antihistamines, steroids, cortisone, immunosuppressive agents, and immune agonist; those which only temporarily alleviate inflammation. These drugs do not fundamentally cure inflammation, and they have side effects such as hypersensitivity reaction, and deterioration of immune system, Therefore, for effective alleviation of inflammation, research is carried out to develop a substance that inhibits expression of the above mentioned Inflammatory proteins. However, problems have arisen in anti-inflammation substances that had been developed previously. Diverse categories of anti-Inflammatory drugs Including Non-steroidal Anti-inflammatory Drugs (NSAIDs) and Steroidal Anti-Inflammatory Drugs (SAIDs) have been developed; but not only do these drugs often bear side effects upon use, they also do not fundamentally cure the inflammation. Thus, there is a current need for anti-inflammatory drugs that both physically and economically feasible. As one example, in acute or chronic inflammations such as chronic rheumatoid arthritis, not only do non-steroidal anti-inflammatory drugs suppress COX-2 enzyme activity, they are also known to suppress COX-1 activity, causing side effects such as gastrointestinal disorders.

The present invention was completed as the present inventors have found that peptides derived from telomerase can have anti-inflammatory properties.

Therefore the objective of this invention is to provide a novel peptide.

Another objective of present invention is to provide the polynucleotide that codes the novel peptide.

Another objective of present invention is to provide a peptide that has anti-inflammatory activity.

Another objective of present invention is to provide an anti-inflammatory composition that uses this peptide as an active ingredient.

Another objective of present invention is to provide a cosmetic composition that uses this peptide as an active ingredient.

Another objective of present invention is to provide a pharmaceutical composition that uses this peptide as an active Ingredient.

SUMMARY OF THE INVENTION

In one embodiment of the present invention, a peptide with anti-inflammatory activity, wherein the peptide comprises at least one amino acid sequence of SEQ ID NO: 2 to SEQ ID NO: 179, or where the peptide has at least 80% sequence identity with the above-mentioned sequences, or the peptide is a fragment of the above-mentioned peptides, is provided.

In another embodiment, the above-mentioned fragment consists of 3 or more amino acids. For Instance, the fragment may consist of 4, 5, 6, 7, 8, 9, 10, 11, 12, 13, 14, 15, 16, 17, 18, 19, 20, 21, 22, 23, 24, 25, or 26 amino acid residues.

In another embodiment, the above-mentioned peptide is made of 30 or less amino acids. For instance, the peptide may consist of 29, 28, 27, 26, 25, 24, 23, 22, 21, 20, 19, 18, 17, 16, 15, 14, 13, 12, 11, 10, 9, or 8 amino acid residues.

In another embodiment, the above-mentioned peptide consists of any one amino acid sequence of SEQ ID NO: 2 to SEQ ID NO: 179.

In another embodiment, the above-mentioned peptide comprises any one amino acid sequence selected from the group consisting of: SEQ ID NO: 9, SEQ ID NO:10, SEQ ID NO: 11, SEQ ID NO: 12, SEQ ID NO: 13, SEQ ID NO: 17, SEQ ID NO: 18, SEQ ID NO: 19, SEQ ID NO: 20, SEQ ID NO: 21, SEQ ID NO: 25, SEQ ID NO: 26, SEQ ID NO: 27, SEQ ID NO: 28, SEQ ID NO: 33, SEQ ID NO: 34, SEQ ID NO: 35, SEQ ID NO: 36, SEQ ID NO: 38, SEQ ID NO: 42, SEQ ID NO: 43, SEQ ID NO: 44, SEQ ID NO: 45, SEQ ID NO: 46, SEQ ID NO: 54, SEQ ID NO: 55, SEQ ID NO: 56, SEQ ID NO: 57, SEQ ID NO: 58, SEQ ID NO: 62, SEQ ID NO: 63, SEQ ID NO: 64, SEQ ID NO: 65, SEQ ID NO: 66, SEQ ID NO: 70, SEQ ID NO: 71, SEQ ID NO: 72, SEQ ID NO: 73, SEQ ID NO: 74, SEQ ID NO: 80, SEQ ID NO: 81, SEQ ID NO: 82, SEQ ID NO: 83, SEQ ID NO: 84, SEQ ID NO: 88, SEQ ID NO: 89, SEQ ID NO: 90, SEQ ID NO: 91, SEQ ID NO: 92, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 108, SEQ ID NO: 109, SEQ ID NO: 110, SEQ ID NO: 111, SEQ ID NO: 112, SEQ ID NO: 113, SEQ ID NO: 116, SEQ ID NO: 117, SEQ ID NO: 118, SEQ ID NO: 119, SEQ ID NO: 124, SEQ ID NO: 131, SEQ ID NO: 140, SEQ ID NO: 141, SEQ ID NO: 142, SEQ 10 NO: 148, SEQ ID NO: 149, SEQ ID NO: 150, SEQ ID NO: 156, SEQ ID NO: 157, SEQ ID NO: 158, SEQ ID NO: 159, SEQ ID NO: 164, SEQ ID NO: 165, SEQ ID NO: 166, SEQ ID NO: 167, SEQ ID NO: 168, SEQ ID NO: 172, SEQ ID NO: 173, SEQ ID NO: 174, SEQ ID NO: 175, SEQ ID NO: 176, SEQ ID NO: 177, and SEQ ID NO: 178.

In another embodiment, the above-mentioned peptide comprises any one amino acid sequence selected from the group consisting of: SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 25, SEQ ID NO: 26, SEQ ID NO: 27, SEQ ID NO: 33, SEQ ID NO: 34, SEQ ID NO: 42, SEQ ID NO: 43, SEQ ID NO: 44, SEQ ID NO: 54, SEQ ID NO: 55, SEQ ID NO: 56, SEQ ID NO: 62, SEQ ID NO: 63, SEQ ID NO: 64, SEQ ID NO: 65, SEQ ID NO: 70, SEQ ID NO: 71, SEQ ID NO: 72, SEQ ID NO: 73, SEQ ID NO: 80, SEQ ID NO: 81, SEQ ID NO: 82, SEQ ID NO: 83, SEQ ID NO: 88, SEQ ID NO: 89, SEQ ID NO: 90, SEQ ID NO: 91, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 102, SEQ ID NO: 103, SEQ ID NO: 108, SEQ ID NO: 109, SEQ ID NO: 110, SEQ ID NO: 116, SEQ ID NO: 117, SEQ ID NO: 140, SEQ ID NO: 148, SEQ ID NO: 149, SEQ ID NO: 156, SEQ ID NO: 157, SEQ ID NO: 164, SEQ ID NO: 165, SEQ ID NO: 166, SEQ ID NO: 167, SEQ ID NO: 172, SEQ ID NO: 173, and SEQ ID NO: 174.

In another embodiment, the above-mentioned peptide comprises any one amino acid sequence selected from the group consisting of: SEQ ID NO: 2 to SEQ ID NO: 5, SEQ ID NO: 7 to SEQ ID NO: 36, SEQ ID NO: 38 to SEQ ID NO: 73, SEQ ID NO: 75, SEQ ID NO: 78 to SEQ ID NO: 107, and SEQ ID NO: 109 to SEQ ID NO: 179.

In another embodiment, the above-mentioned peptide comprises any one amino acid sequence selected from group consisting of: SEQ ID NO: 2, SEQ ID NO: 2, SEQ ID NO: 3, SEQ ID NO: 30, SEQ ID NO: 41, SEQ ID NO: 112 and SEQ ID NO: 113.

In another embodiment, the above-mentioned peptide comprises any one amino acid sequence selected from the group consisting of: SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 22, SEQ ID NO: 23, SEQ ID NO: 24, SEQ ID NO: 26, SEQ ID NO: 27, SEQ ID NO: 28, SEQ ID NO: 29, SEQ ID NO: 30, SEQ ID NO: 35, SEQ ID NO: 36, SEQ ID NO: 37, SEQ ID NO: 38, SEQ ID NO: 40, SEQ ID NO: 43, SEQ ID NO: 45, SEQ ID NO: 46, SEQ ID NO: 47, SEQ ID NO: 48, SEQ ID NO: 57, SEQ ID NO: 58, SEQ ID NO: 61, SEQ ID NO: 64, SEQ ID NO: 65, SEQ ID NO: 66, SEQ ID NO: 68, SEQ ID NO: 70, SEQ ID NO: 73, SEQ ID NO: 74, SEQ ID NO: 75, SEQ ID NO: 82, SEQ ID NO: 83, SEQ ID NO: 87, SEQ ID NO: 88, SEQ ID NO: 89, SEQ ID NO: 91, SEQ ID NO: 93, SEQ ID NO: 95, SEQ ID NO: 96, SEQ ID NO: 98, SEQ ID NO: 102, SEQ ID NO: 109, SEQ ID NO: 110, SEQ ID NO: 111, SEQ ID NO: 112, SEQ ID NO: 113, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 123, SEQ ID NO: 127, SEQ ID NO: 128, SEQ ID NO: 130, SEQ ID NO: 132, SEQ ID NO: 133, SEQ ID NO: 134, SEQ ID NO: 135, SEQ ID NO: 136, SEQ ID NO: 142, SEQ ID NO: 143, SEQ ID NO: 144, SEQ ID NO: 145, SEQ ID NO: 147, SEQ ID NO: 148, SEQ ID NO: 149, SEQ ID NO: 153, SEQ ID NO: 154, SEQ ID NO: 155, SEQ ID NO: 157, SEQ ID NO: 158, SEQ ID NO: 164, SEQ ID NO: 165, SEQ ID NO: 166, SEQ ID NO: 167, SEQ ID NO: 170, SEQ ID NO: 171, SEQ ID NO: 172, SEQ ID NO: 173, SEQ ID NO: 175, SEQ ID NO: 176, SEQ ID NO: 177, SEQ ID NO: 178, and SEQ ID NO: 179.

In another embodiment, the above-mentioned peptide originates from human telomerase.

In one embodiment of the present invention, a polynucleotide encoding a peptide with anti-inflammatory activity, wherein the peptide comprises at least one amino acid sequence of SEQ ID NO: 2 to SEQ ID NO: 179, or the peptide has at least 80% sequence identity with the above-mentioned sequences, or the peptide is a fragment of the above-mentioned peptides, is provided.

In another embodiment of the polynucleotide, the above-mentioned peptide consists of 30 or less amino acids. For Instance, the peptide may consist of 29, 28, 27, 26, 25, 24, 23, 22, 21, 20, 19, 18, 17, 16, 15, 14, 13, 12, 11, 10, 9, or 8 amino acid residues. In another embodiment of the polynucleotide, the above-mentioned peptide consists of any one amino acid sequence of SEQ ID NO: 2 to SEQ ID NO: 179.

In another embodiment of the polynucleotide, the above-mentioned peptide originates from human telomerase.

In one embodiment of the present invention, anti-inflammatory composition comprising a peptide as active Ingredient, wherein the peptide comprises at least amino acid sequence of SEQ ID NO: 2 to SEQ ID NO: 179, the peptide has above 80% homology of amino acid sequence with above-mentioned sequences, or the peptide is a fragment of the above-mentioned peptides, is provided.

In another embodiment of the composition, the above-mentioned peptide consists of 30 or less amino acids, cf. above.

In another embodiment of the composition, the above-mentioned peptide consists of any one amino acid sequence from SEQ ID NO: 2 to SEQ ID NO: 179.

In another embodiment of the composition, the above-mentioned peptide originates from human telomerase.

In another embodiment of the composition, the above-mentioned composition is for treatment or prophylaxis of inflammatory disease.

In another embodiment of the composition, the above-mentioned composition is a cosmetic composition for improving or preventing skin inflammation.

In another embodiment of the composition, the above-mentioned composition is a pharmaceutical composition for treatment or prophylaxis of inflammatory diseases.

In another embodiment of the composition, the above-mentioned composition is a food composition for treatment or prophylaxis of inflammation.

In another embodiment of the composition, the above-mentioned inflammatory disease is characterized by selecting from the group consisting of (1) general or localized inflammatory disease (for example, allergies; immune-complex disease; hayfever; hypersensitive shock; endotoxin shock; cachexia, hyperthermia; granulomatosis; or sarcoidosis); (2) gastro-intestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, anglitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophillc granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease).

In one embodiment of the present invention, a method for treating or preventing inflammatory diseases by administering the anti-inflammatory composition is provided.

In one embodiment of the present invention, a kit for prophylaxis or treatment of inflammatory diseases comprising: a peptide with anti-inflammatory activity or a composition comprising of the peptide, wherein the peptide comprises at least one amino acid sequence of SEQ ID NO: 2 to SEQ ID NO: 179, the peptide has above 80% homology with above-mentioned sequences, or the peptide is a fragment of the above-mentioned peptides; and instructions including at least one of administration dose, administration route, administration frequency, and Indication of the peptide or composition, is provided.

INDUSTRIAL APPLICABILITY

According to the present invention, a peptide that has a sequence of SEQ ID NO: 2 to SEQ ID NO: 179 has outstanding efficacy in both suppressing inflammation and in prophylactic means. Therefore, the composition comprising the peptides of this invention can be used as anti-inflammatory pharmaceutical composition or as cosmetic composition, in turn, treating and preventing a variety of different types of inflammatory diseases.

REFERENCES

KR2012-0130996A
KR2012-0133661A
KR2011-0060940A
US2011-0150873A1
Bonaidi T et al., EMBO J, (22)5551-60, 2003
Yankner B A et al, Science (New York, N.Y.) [1990, 250 (4978):279-282]
Dahlgren K N et al. J. Biol. Chem. 277:32046-32053, 2002.

DETAILED DESCRIPTION OF THE INVENTION

Figure 1:
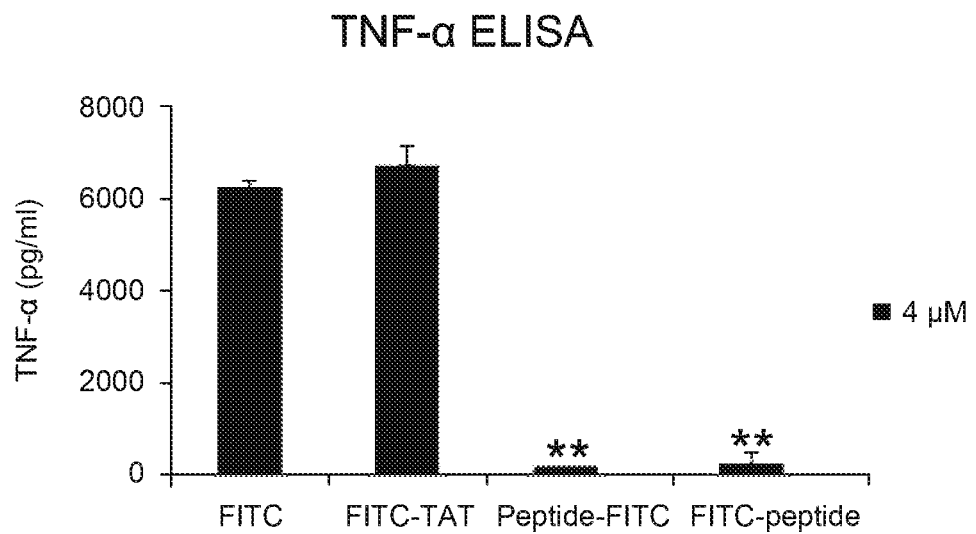
FIG. 1 is a graph which shows the results of performing TNF-α ELISA with the culture of monocytes derived from PBMC. The monocytes were stimulated with LPS (10 ng/ml) for two hours, then reacted with each peptide, FITC, FITC-TAT, PEP 1-FITC and FITC-peptide for two hours. (** P<0.01. Compared with the negative control (FITC and FITC-TAT).

Since the present invention can have adaptability for diverse transformation and examples of practical application, below Is a more detailed description of the present invention. Nevertheless, this is no means to limit the form of practical application; It should be understood that the Intention is to include the concept and the extent of technology in all of the transformation, equivalents to alternatives. In describing the present invention, if any detailed description about the prior art is considered to deteriorate the fundamental principles of the present Invention, the description will be omitted.

A telomere is known as a repetitive sequence of genetic material at the ends of chromosomes that prevent chromosomes from damage or merging of other chromosomes. The length of a telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells. The present invention was accomplished upon the discovery of telomerase-derived peptides with anti-inflammatory effects.

In one embodiment of the present invention, a peptide with anti-inflammatory activities is provided. The peptide comprises at least one amino acid sequence of SEQ ID NO: 2 to SEQ ID NO: 179, the peptide has above 80% homology with above-mentioned sequences, or the peptide is a fragment of the above-mentioned peptides.

The peptides described in SEQ ID NO: 2 to SEQ ID NO: 179 are as the following table 1. SEQ ID NO: 180 lists the order of full length of human telomerase protein. SEQ ID NO: 1 lists the telomerase-derived peptide that consists of 16 amino acid sequence. The peptides that are mentioned in SEQ ID NO: 2 to SEQ ID NO: 179 are as the following table 1. SEQ ID NO: 180 lists the order of full length of human telomerase protein. SEQ ID NO: 1 lists the telomerase-derived peptide that consists of 16 amino acid sequence. Peptides in SEQ ID NO: 2 to SEQ ID NO: 77 are peptide including SEQ ID NO: 1. Peptides in SEQ ID NO: 78 to SEQ ID NO: 179 are fragments of peptide of SEQ ID NO: 1.

The "name" in Table 1 below was used for distinction of peptides. In a different specific embodiment of the present Invention, more than one peptide of the mentioned peptides in SEQ ID NO: 2 to SEQ ID NO: 179 comprise a "synthetic peptide", a synthesized peptide of selected areas of the telomerase. In the present specification, the term "pep" herein relates to a peptide that has any one of the SEQ ID NO: 2 to SEQ ID NO: 179, or, a peptide comprising of amino acid sequence above 80% homology with above-mentioned sequences, or a peptide fragment of above-mentioned peptides.

TABLE 1

| SEQ ID NO | NAME | POSITION IN TELOMERASE | SEQUENCE | LENGTH |
|---|---|---|---|---|
| 1. | pep1 | [611-626] | EARPALLTSRLRFIPK | 16 aa |
| 2. | pep-RIA-1 | [610-626] | REARPALLTSRLRFIPK | 17 aa |
| 3. | pep-RIA-2 | [609-626] | HREARPALLTSRLRFIPK | 18 aa |

TABLE 1-continued

| SEQ ID NO | NAME | POSITION IN TELOMERASE SEQUENCE | | LENGTH |
|---|---|---|---|---|
| 4. | pep-RIA-3 | [608-626] | QHREARPALLTSRLRFIPK | 19 aa |
| 5. | pep-RIA-4 | [607-626] | RQHREARPALLTSRLRFIPK | 20 aa |
| 6. | pep-RIA-5 | [606-626] | VRQHREARPALLTSRLRFIPK | 21 aa |
| 7. | pep-RIA-6 | [605-626] | EVRQHREARPALLTSRLRFIPK | 22 aa |
| 8. | pep-RIA-7 | [604-626] | 1AEVR.QHREARPALLTSRLRFIPK | 23 aa |
| 9. | pep-RIA-8 | [603-626] | EAEVRQHREARPALLTSRLRFIPK | 24 aa |
| 10. | pep-RIA-9 | [602-626] | pEAEVRQHREARPALLTSRLRFIPK | 25 aa |
| 11. | pep-RIA-10 | [601-626] | LSEAEVRQHREARPALLTSRLR.FIPK | 26 aa |
| 12. | pep-RIA-11 | [600-626] | ELSEAEVRQHREARPALLTSRLRFIPK | 27 aa |
| 13. | pep-RIA-12 | [599-626] | RELSEAEVRQHREARPALLTSRLRFIPK | 28 aa |
| 14. | pep-RIA-13 | [598-626] | LRELSEAEVRQHREARPALLTSRLRFIPK | 29 aa |
| 15. | pep-RIA-14 | [597-626] | QLRELSEAEVRQHREARPALLTSRLRFIPK | 30 aa |
| 16. | pep-RIA-15 | [610-627] | REARPALITSRIRFIPKP | 18 aa |
| 17. | pep-RIA-16 | [609-627] | HREARPALLTSRLRFIPKP | 19 aa |
| 18. | pep-RIA-17 | [609-628] | HREARPALLTSRLRFIPKPD | 20 aa |
| 19. | pep-RIA-18 | [610-628] | REARPALITSRIRFIPKPD | 19 aa |
| 20. | pep-RIA-19 | [608-627] | QHREARPALLT5RLRFIPKP | 20 aa |
| 21. | pep-RIA-20 | [608-628] | QHREARPALLTSRLRFIPKPD | 21 aa |
| 22. | pep-RIA-21 | [608-629] | PHREARPALLTSRLREIPKPDG | 22 aa |
| 23. | pep-RIA-22 | [609-629] | HREARPALLTSRLRFIPKPDG | 21 aa |
| 24. | pep-RIA-23 | [610-629] | REARPALLTSRLRFIPKPDG | 20 aa |
| 25. | pep-RIA-24 | [607-627] | RQHREARPALLTSRLRFIPKP | 21 aa |
| 26. | pep-RIA-25 | [607-628] | RQHREARPALLTSRLRFIPKPD | 22 aa |
| 27. | pep-RIA-26 | [607-629] | RQHREARPALLTSRLRFIPKPDG | 23 aa |
| 28. | pep-RIA-27 | [607-630] | RQHREARPALLTSRLRFIPKPDGL | 24 aa |
| 29. | pep-RIA-28 | [608-630] | QHREARPALLTSRLRFIPKPDGL | 23 aa |
| 30. | pep-RIA-29 | [609-630] | HREARPALLTSRLRFIPKPDGL | 22 aa |
| 31. | pep-RIA-30 | [610-630] | REARPALLTSRLRFIPKPDGL | 21 aa |
| 32. | pep-RIA-31 | [606-627] | VRQHREARPALLTSRLRFIPKP | 22 aa |
| 33. | pep-RIA-32 | [606-628] | VRQHREARPALLTSRLRFIPKPD | 23 aa |
| 34. | pep-RIA-33 | [606-629] | VRQHREARPALLTSRLRFIPKPDG | 24 aa |
| 35. | pep-RIA-34 | [606-630] | VRQHREARPALLTSRLRFIPKPDGL | 25 aa |
| 36. | pep-RIA-35 | [606-631] | VRQHREARPALITSRIRFIPKPDGLR | 26 aa |
| 37. | pep-RIA-36 | [607-631] | RQHREARPALLTSRLRFIPKPDGLR | 25 aa |
| 38. | pep-RIA-37 | [608-631] | QHREARPALLTSRLRFIPKPDGLR | 24 aa |
| 39. | pep-RIA-38 | [609-631] | HREARPALLTSRLRFIPKPDGLR | 23 aa |
| 40. | pep-RIA-39 | [610-631] | REARPALLTSRLRFIPKPDGLR | 22 aa |
| 41. | pep-RIA-40 | [605-627] | EVRQHREARPALITSRIRFIPKP | 23 aa |

TABLE 1-continued

| SEQ ID NO | NAME | POSITION IN TELOMERASE | SEQUENCE | LENGTH |
|---|---|---|---|---|
| 42. | pep-RIA-41 | [605-628] | EVRQHREARPALLTSRLRFIPKPD | 24 aa |
| 43. | pep-RIA-42 | [605-629] | EVRQHREARPALLTSRLRFIPKPDG | 25 aa |
| 44. | pep-RIA-43 | [605-630] | EVRQHREARPALLTSRLRFIPKPDGL | 26 aa |
| 45. | pep-RIA-44 | [605-631] | EVRQHREARPALLTSRLRFIPKPDGLR | 27 aa |
| 46. | pep-RIA-45 | [605-632] | EVRQHREARPALLTSRLRFIPKPDGLRP | 28 aa |
| 47. | pep-RIA-46 | [606-632] | VRQHREARPALLTSRLRFIPKPDGLRP | 27 aa |
| 48. | pep-RIA-47 | [607-632] | RQHREARPALLTSRLRFIPKPDGLRP | 26 aa |
| 49. | pep-RIA-48 | [608-632] | QHREARPALLTSRLRFIPKPDGLRP | 25 aa |
| 50. | pep-RIA-49 | [609-632] | HREARPALLTSRLRFIPKPDGLRP | 24 aa |
| 51. | pep-RIA-50 | [610-632] | REARPALLTSRLRFIPKPDGLRP | 23 aa |
| 52. | pep-RIA--51 | [604-627] | AEVRQHREARPALLTSRLRFIPKP | 24 aa |
| 53. | pep-RIA-52 | [604-628] | AEVRQHREARPALLTSRLRFIPKPD | 25 aa |
| 54. | pep-RIA-53 | [604-629] | 1AEVRQHREARPALLTSRLRFIPKPDG | 26 aa |
| 55. | pep-RIA-54 | [604-630] | AEVRQHREARPALLTSRLRFIPKPDGL | 27 aa |
| 56. | pep-RIA-55 | [604-631] | AEVRQHREARPALLTSRLRFIPKPDGLR | 28 aa |
| 57. | pep-RIA-56 | [604-632] | AEVRQHREARPALLTSRLRFIPKPDGLRP | 29 aa |
| 58. | pep-RIA-57 | [604-633] | AEVRQHREARPALITSRLRFIPKPDGLRPT | 30 aa |
| 59. | pep-RIA-58 | [605-633] | EVRQHREARPALLTSRLRFIPKPDGLRPI | 29 aa |
| 60. | pep-RIA-59 | [606-633] | VRQHSREARPALLTSRLREIPKPDGLRPI | 28 aa |
| 61. | pep-RIA-60 | [607-633] | RQHREARPALLTSRLRFIPKPDGLRPI | 27 aa |
| 62. | pep-RIA-61 | [608-633] | QHREARPALLTSRLRF1PKPDGLRPI | 26 aa |
| 63. | pep-RIA-62 | [609-633] | HREARPALLTSRLRFIPKPDGLRPI | 25 aa |
| 64. | pep-RIA-63 | [610-633] | REARPALLTSRLRFIPKPDGLRPI | 24 aa |
| 65. | pep-RIA-64 | [611-627] | EARPALLTSRLRFIPKP | 17 aa |
| 66. | pep-RIA-65 | [611-628] | EARPALLTSRLRFIPKPD | 18 aa |
| 67. | pep-RIA-66 | [611-629] | EARPALLTSRLRF1PKPDG | 19 aa |
| 68. | pep-RIA-68 | [611-631] | EARPALLTSRLRFIPKPDGLR | 21 aa |
| 69. | pep-RIA-69 | [611-632] | EARPALLTSRLRFIPKPDGLRP | 22 aa |
| 70. | pep-RIA-70 | [611-633] | EARPALLTSRLRFIPKPDGLRPI | 23 aa |
| 71. | pep-RIA-71 | [611-634] | EARPALLTSRLRFIPKPDGLRPIV | 24 aa |
| 72. | pep-RIA-72 | [611-635] | EARPALLTSRLRFIPKPDGLRPIVN | 25 aa |
| 73. | pep-RIA-73 | [611-636] | EARPALLTSRLRFIPKPDGLRPIVNM | 26 aa |
| 74. | pep-RIA-74 | [611-637] | EARPALLTSRLRFIPKPDGLRPIVNMD | 27 aa |
| 75. | pep-RIA-75 | [611-638] | EARPALLTSRLRFIPKPDGLRPIVNMDY | 28 aa |
| 76. | pep-RIA-76 | [611-639] | EARPALLTSRLRFIPKPDGLRPIVNMDYV | 29 aa |
| 77. | pep-RIA-77 | [611-640] | EARPALLTSRLRFIPKPDGLRPIVNMDYVV | 30 aa |
| 78. | pep-RIA-78 | [611-625] | EARPALLTSRLRFIP | 15 aa |
| 79. | pep-RIA-79 | [611-624] | EARPALLTSRLRFI | 14 aa |

TABLE 1-continued

| SEQ ID NO | NAME | POSITION IN TELOMERASE | SEQUENCE | LENGTH |
|---|---|---|---|---|
| 80 | pep-RIA-80 | [611-623] | EARPALLTSRLRF | 13 aa |
| 81 | pep-RIA-81 | [611-622] | EARPALLTSRLR | 12 aa |
| 82 | pep-RIA-82 | [611-621] | EARPALLTSRL | 11 aa |
| 83 | pep-RIA-83 | [611-620] | EARPALLTSR | 10 aa |
| 84 | pep-RIA-84 | [611-619] | EARPALLTS | 9 aa |
| 85 | pep-RIA-85 | [611-618] | EARPALLT | 8 aa |
| 86 | pep-RIA-86 | [611-617] | EARPALL | 7 aa |
| 87 | pep-RIA-87 | [611-616] | EARPAL. | 6 aa |
| 88 | pep-RIA-88 | [611-615] | EARPA | 5 aa |
| 89 | pep-RIA-89 | [611-614] | EARP | 4 aa |
| 90 | pep-RIA-90 | [611-613] | EAR | 3 aa |
| 91 | pep-RIA-91 | [612-626] | ARPALLTSRLRFIPK | 15 aa |
| 92 | pep-RIA-92 | [613-626] | RPALLTSRLRFIPK | 14 aa |
| 93 | pep-RIA-93 | [614-626] | PALITSRIRFIPK | 13 aa |
| 94 | pep-RIA-94 | [615-626] | ALLTSRLRFIPK | 12 aa |
| 95 | pep-RIA-9 | [616-626] | LLTSRLRFI PK | 11 aa |
| 96 | pep-RIA-96 | [617-626] | LTSRLRFIPK | 10 aa |
| 97 | pep-RIA-97 | [618-626] | TSRLRFIPK | 9 aa |
| 98 | pep-RIA-98 | [619-626] | SRLRFIPK | 8 aa |
| 99 | pep-RIA-99 | [620-626] | RLRFIPK | 7 aa |
| 100 | pep-RIA-100 | [621-626] | LRFIPK | 6 aa |
| 101 | pep-RIA-101 | [622-626] | RFIPK | 5 aa |
| 102 | pep-RIA-102 | [623-626] | FIPK | 4 aa |
| 103 | pep-RIA-103 | [624-626] | IPK | 3 aa |
| 104 | pep-RIA-104 | [612-625] | ARPALLTSRLRFIP | 14 aa |
| 105 | pep-RIA-105 | [613-624] | RPALLTSRLRFI | 12 aa |
| 106 | pep-RIA-106 | [614-623] | PALLTSRLRF | 10 aa |
| 107 | pep-RIA-107 | [615-622] | ALLTSRLR | 8 aa |
| 108 | pep-RIA-108 | [616-621] | LLTSRL | 6 aa |
| 109 | pep-RIA-109 | [617-620] | LTSR | 4 aa |
| 110 | pep-RIA-110 | [612-624] | ARPALLTSRLRFI | 13 aa |
| 111 | pep-RIA-111 | [612-623] | ARPALLTSRLRF | 12 aa |
| 112 | pep-RIA-112 | [612-622] | ARPALLTSRLR | 11 aa |
| 113 | pep-RIA-113 | [612-621] | IARPALLTSRL | 10 aa |
| 114 | pep-RIA-114 | [612-620] | ARPALLTSR | 9 aa |
| 115 | pep-RIA-115 | [612-619] | ARPALLTS | 8 aa |
| 116 | pep-RIA-116 | [612-618] | 1ARPALLT | 7 aa |
| 117 | pep-RIA-117 | [612-617] | ARPALL | 6 aa |

TABLE 1-continued

| SEQ ID NO | NAME | POSITION IN TELOMERASE | SEQUENCE | LENGTH |
|---|---|---|---|---|
| 118. | pep-RIA-118 | [612-616] | ARPAL | 5 aa |
| 119. | pep-RIA-119 | [612-615] | ARPA | 4 aa |
| 120. | pep-RIA-120 | [612-614] | ARP | 3 aa |
| 121. | pep-RIA-121 | [613-625] | RPALLTSRLRFIP | 13 aa |
| 122. | pep-RIA-122 | [613-623] | RPALITSRIRF | 11 aa |
| 123. | pep-RIA-123 | [613-622] | RPALLTSRLR | 10 aa |
| 124. | pep-RIA-124 | [613-620] | RPALLTSR | 8 aa |
| 125. | pep-RIA-125 | [613-619] | RPALLTS | 7 aa |
| 126. | pep-RIA-126 | [613-618] | RPALLT | 6 aa |
| 127. | pep-RIA-127 | [613-617] | RPALL | 5 aa |
| 128. | pep-RIA-128 | [613-616] | RPAL | 4 aa |
| 129. | pep-RIA-129 | [613-615] | RPA | 3 aa |
| 130. | pep-RIA-130 | [614-625] | PALLTSRLRFIP | 12 aa |
| 131. | pep-RIA-131 | [614-624] | PALLTSRLRFI | 11 aa |
| 132. | pep-RIA-132 | [614-622] | PALLTSRLR | 9 aa |
| 133. | pep-RIA-133 | [614-621] | PALLTSRL | 8 aa |
| 134. | pep-RIA-134 | [614-620] | PALLTSR | 7 aa |
| 135. | pep-RIA-135 | [614-619] | PALLTS | 6 aa |
| 136. | pep-RIA-136 | [614-618] | PALLT | 5 aa |
| 137. | pep-RIA-137 | [614-617] | PALL | 4 aa |
| 138. | pep-RIA-138 | [614-616] | PAL | 3 aa |
| 139. | pep-RIA-139 | [615-625] | ALLTSRLRFIP | 11 aa |
| 140. | pep-RIA-140 | [615-623] | ALLTSRLRF | 9 aa |
| 141. | pep-RIA-141 | [615-621] | ALLTSRL | 7 aa |
| 142. | pep-RIA-142 | [615-620] | ALLTSR | 6 aa |
| 143. | pep-RIA-143 | [615-619] | ALLTS | 5 aa |
| 144. | pep-RIA-144 | [615-618] | ALLT | 4 aa |
| 145. | pep-RIA-145 | [615-617] | ALL | 3 aa |
| 146. | pep-RIA-146 | [616-625] | ILTSRLRFIP | 10 aa |
| 147. | pep-RIA-147 | [616-624] | LLTSRLRFI | 9 aa |
| 148. | pep-RIA-148 | [616-623] | LLTSRLRF | 8 aa |
| 149. | pep-RIA-149 | [616-622] | LLTSRLR | 7 aa |
| 150. | pep-RIA-150 | [616-620] | LLTSR | 5 aa |
| 151. | pep-RIA-151 | [616-619] | LLTS | 4 aa |
| 152. | pep-RIA-152 | [616-618] | LLT | 3 aa |
| 153. | pep-RIA-153 | [617-625] | LTSRLREIP | 9 aa |
| 154. | pep-RIA-154 | [617-624] | LTSRLRFI | 8 aa |
| 155. | pep-RIA-155 | [617-623] | LTSRLRF | 7 aa |

TABLE 1-continued

| SEQ ID NO | NAME | POSITION IN TELOMERASE | SEQUENCE | LENGTH |
|---|---|---|---|---|
| 156. | pep-RIA-156 | [617-622] | LTSRLR | 6 aa |
| 157. | pep-RIA-157 | [617-621] | ITSRL | 5 aa |
| 158. | pep-RIA-158 | [617-619] | LTS | 3 aa |
| 159. | pep-R1A-159 | [618-6251] | TSRLRFIP | 8 aa |
| 160. | pep-RIA-160 | [618-624] | TSRIRFI | 7 aa |
| 161. | pep-RIA-161 | [618-623] | TSRLRF | 6 aa |
| 162. | pep-RIA-162 | [618-622] | TSRLR | 5 aa |
| 163. | pep-RIA-163 | [618-621] | TSRL | 4 aa |
| 164. | pep-RIA-164 | [618-620] | TSR | 3 aa |
| 165. | pep-RIA-165 | [619-625] | SRLREIP | 7 aa |
| 166. | pep-RIA-166 | [619-624] | SRLRFI | 6 aa |
| 167. | pep-RIA-167 | [619-623] | SRLRF | 5 aa |
| 168. | pep-RIA-168 | [619-622] | SRLR | 4 aa |
| 169. | pep-RIA-169 | [619-621] | SRL | 3 aa |
| 170. | pep-RIA-170 | [620-625] | RLRFIP | 6 aa |
| 171. | pep-RIA-171 | [620-624] | RLRFI | 5 aa |
| 172. | pep-RIA-172 | [620-623] | RLRF | 4 aa |
| 173. | pep-RIA-173 | [620-622] | RLR | 3 aa |
| 174. | pep-RIA-174 | [621-625] | LRFIP | 5 aa |
| 175. | pep-RIA-175 | [621-624] | LRFI | 4 aa |
| 176. | pep-RIA-176 | [621-623] | IRE | 3 aa |
| 177. | pep-RIA-177 | [622-625] | RFIP | 4 aa |
| 178. | pep-RIA-178 | [622-624] | RFI | 3 aa |
| 179. | pep-RIA-179 | [623-625] | FIP | 3 aa |
| 180. | Telomerase | [1-1132] | MPRAPRCRAVRSLLRSHYREVLPLATFVR RLGPQGWRLVQRGDPAAFRALVAQCLVCV PWDARPPPAAPSFRQVSCLKELVARVIQR LCERGAKNVLAFGFALLDGARGGPPEAFT TSVRSYLPNTVTDALRGSGAWGLLLRRVG DDVLVFILLARCALFVLVAPSCAYQVCGP PLYQLGAATQARPPPHASGPRRRLGCERA WNHSVREAGVPLGLPAPGARRRGGSASRS LPLPKRPRRGAAPEPERTPVGQGSWAHPG RTRGPSDRGFCVVSPARPAEEATSLEGAL SGTRHSHPSVGRQHHAGPPSTSRPPRPWD TPCPPVYAETKHFLYSSGDKEQLRPSFLL SSLRPSLTGARRLVETIFLGSRPWMPGTP RRLPRLPQRYWQMRPLFLELLGNHAQCPY GVLLKTHCPLRAAVTPAAGVCAREKPQGS VAAPEEEDTDPRRLVQLLRQHSSPWQVYG FVRACLRRLVPPGLWGSRHNERRFLRNTK KFISLGKHAKLSLQELIWKMSVRDCAWLR RSPGVGCVPAAEHRLREEILAKFLHWLMS VYVVELLRSFFYVTETTFQKNRLFFYRKS VWSKLQSIGIRQHLKRVQLRELSEAEVRQ HREARPALLTSRLRFIPKPDGLRPIVNMD YVVGARTERREKRAERLTSRVKALFSVLN YERARRPGLLGASVLGLDDIHRAVVRTFV LRVRAQOPPPELYFVKVDVTGAYDTIPQD RLTEVIASIIKPQNTYCVRRYAVVQKAAH GHVRKAFKSHVSTLTDLQPYMRQFVAHLQ | 1132 aa |

TABLE 1-continued

| SEQ ID NO | NAME | POSITION IN TELOMERASE SEQUENCE | LENGTH |
|---|---|---|---|
| | | ETSPLRDAVVIEQSSSLNEASSGLFDVFL<br>RFMCHHAVRIRGKSYVQCQGIPOGSILST<br>LLCSLCYGDMENKLFAGIRRIDGLLLRLY<br>DDFLIVIPHLTHAKTFLRTLVRGVPEYGC<br>VVNLRKTVVNFPVEDEALGGTAFVQMPAH<br>GLFPWCGLLLDTRTLEVQSDYSSYARTSI<br>RASLTFNRGFKAGRNMRRKLFGVLRLKCH<br>SLFLDLQVNSLQTVCTNIYKILLLQAYRF<br>HACVLQLPFHQQVWKNPTFFLRVISDTAS<br>LCYSILKAKNAGMSLGAKGAAGPLPSEAV<br>QWLCHQAFLLKLTRHRVTYVPLLGSLRTA<br>QTQLSRKLPGTTLTALEAAANPALPSDFK<br>TILD | |

In one embodiment of the present invention, a polynucleotide that codes a peptide with anti-Inflammatory activities is provided. The polynucleotide codes a peptide comprising at least one amino acid sequence of SEQ ID NO: 2 to SEQ ID NO: 179, a peptide having above 80% homology with above-mentioned sequences, or a peptide being a fragment of the above-mentioned peptides. The polynucleotide mentioned above enables production of the peptides in large quantities. For example, cultivation of vectors that include polynucleotides encoding peptides allows production of peptides in large quantities.

The peptides disclosed herein can include a peptide comprising amino acid sequence above 80%, above 85%, above 90%, above 95%, above 96%, above 97%, above 98%, or above 99% homology. Moreover, the peptides disclosed in the present invention can include a peptide comprising SEQ ID NO: 1 or its fragments, and a peptide with more than 1 transformed amino acid, more than 2 transformed amino acid, more than 3 transformed amino acid, more than 4 transformed amino acid, more than 5 transformed amino acid, more than 6 transformed amino acid, or more than 7 transformed amino acid.

In the present specification and claims, the terms "homology" and "sequence identity" are used interchangeably to indicate the degree of sequence overlap between two amino acid (or if relevant: nucleic acid) sequences.

Unless otherwise stated the term "Sequence identity" for peptides as used herein refers to the sequence identity calculated as $(n_{ref}-n_{dif}) \cdot 100/n_{ref}$, wherein $n_{dif}$ is the total number of non-identical residues in the two sequences when aligned so that a maximum number of amino acids are identical and wherein $n_{ref}$ is the number of residues in the shortest of the sequences. Hence, the DNA sequence agtcagtc will have a sequence identity of 75% with the sequence aatcaatc ($n_{dif}=2$ and $n_{ref}=8$).

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

In one embodiment of the present invention, changes in amino acid sequence belong to the modification of peptide's physical and chemical characteristics. For example, amino acid transformation can be performed by improving thermal stability of the peptide, altering substrate specificity, and changing the optimal pH.

In one embodiment of the present invention, a peptide comprising amino acid sequence of at least one of SEQ ID NO: 2 to SEQ ID NO: 179, a peptide comprising of amino acid sequence above 80% homology with above-mentioned sequences, or a peptide fragment of above-mentioned peptides is preferably made of 30 or less amino acids.

In one embodiment of the present invention, a peptide comprising amino acid sequence of at least one of SEQ ID NO: 2 to SEQ ID NO: 179, a peptide comprising of amino acid sequence above 80% homology with above-mentioned sequences, or a peptide fragment of above-mentioned peptides comprises a peptide originages from telomerase, more specifically, telomerase of Homo sapiens.

The term "amino acid" herein Includes not only the 22 standard amino acids that are naturally Integrated into peptide but also the D-Isomers and transformed amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, transformation in chemical properties (e.g. A-removing deimidation, deamidation) and structural transformation (e.g. formation of disulfide bridge). Also, changes of amino acids are included and the changes of amino acids occur due to chemical reaction during the combination process with crosslinkers for formation of a peptide conjugate.

A peptide disclosed herein may be a wild-type peptide that has been identified and isolated from natural sources. On the other hand, when compared to peptide fragments of SEQ ID NO: 1, the peptides disclosed herein may be artificial mutants that comprise one or more substituted, deleted and/or inserted amino acids. Amino acid alteration in wild-type polypeptide—not only in artificial mutants—comprises conservative substitution of amino acids that do not influence protein folding and or activation. Examples of conservative substitution belong to the group consisting of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activity are known in the art of the present Invention. Most common occurred alteration are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ie, Leu/Val, Ala/Glu, Asp/Gly, and the opposite alterations. Another example of conservative substitutions are shown in the following table 2.

TABLE 2

| Original amino acid | Examples of residue substitution | Preferable residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

The substantial transformation of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:

(1) hydrophobicity: Norleucine, met, ala, val, leu, Iie;
(2) neutral hydrophilicity: cys, ser, thr;
(3) acidity: asp, glu;
(4) basicity: asn, gln, his, lys arg;
(5) residue that affects chain orientation: gly, pro; and
(6) aromaticity: trp, tyr, phe.

Non-conservative substitutions may be performed by exchanging a member of the above classes to that of a different class. Any cysteine residues that are not related in maintaining the proper three-dimensional structure of the peptide can typically be substituted into serine, thus Increasing the oxidative stability of the molecule and preventing Improper crosslinkage. Conversely, improvement of stability can be achieved by adding cysteine bond(s) to the peptide.

Altered types of amino acids variants of peptides are those that antibody glycosylation pattern changed. The term "change" herein relates to deletion of carbohydrate residues and/or addition of at least one glycosylated residues that do not exist within a peptide.

Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequence for attaching carbohydrate residue enzymatically to the side chain of asparagine. Therefore, with the presence of one of these tripeptide sequences in a polypeptide, the potential glycosylation sites are created. "O-connected glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing amino acid sequence to contain tripeptide sequence mentioned above (for N-linked glycosylation sites). These changes may be made by addition of at least one serine or theronine residues to the first antibody sequence, or by substitution with those residues (for O-linked glycosylation sites).

In one embodiment of the present invention, a polynucleotide is a nucleic acid molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those.

A HMGB1 protein is known as a cytokine. It first undergoes acetylation and translocation to cytoplasm by external stimulation. Then it Is secreted out of the cell, therefore serving the role of inflammation-causing cytokine. Because when one has an inflammation due to such activity, HMGB1 protein is secreted out of the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it is suggestive of the fact that HMGB1 is not being secreted out of the cell, which means inflammation is being suppressed.

In one embodiment of the present invention, when treated a cell with a peptide comprising any one amino acid sequence among SEQ ID NO: 2 to SEQ ID NO: 179, a peptide having above 80% homology of amino acid sequence with above-mentioned sequences, or a fragment of the above-mentioned peptides, amount of HMGB1 within the nucleus increases. This represents that the peptides mentioned above have excellent inflammation preventive or suppressive effects.

Also, in specific embodiments of the present invention, a peptide comprising any one amino acid sequence among SEQ ID NO: 2 to SEQ ID NO: 179, a peptide having above 80% homology of amino acid sequence with above-mentioned sequences, or a fragment of the above-mentioned peptides, has an advantage in that it has high feasibility due to its low toxicity within a cell.

In the present invention, an "inflammatory disease" is a broad indication that refers to any disease that designates inflammation as a main cause or inflammation caused by disease. Specifically, an inflammatory disease includes (1) general or localized inflammatory disease (for example, allergies; immune-complex disease; hayfever; hypersensitive shock; endotoxin shock; cachexia, hyperthermia; granulomatosis; or sarcoidosis); (2) gastro-intestinal related diseases (for example, appendicitis; gastric ulcer; duodenal ulcer; peritonitis; pancreatitis; ulcerative, acute, or ischemic colitis; cholangitis; cholecystitis, steatorrhea, hepatitis, Crone's disease; or Whipple's Disease); (3) dermal related diseases (for example, psoriasis; burns; sunburns; dermatitis; Urticarial warts or wheal); (4) vascular related diseases (for example, angiitis; vasculitis; endocarditis; arteritis; atherosclerosis; thrombophlebitis; pericarditis; congestive heart failure; myocarditis; myocardial ischemia; periarteritis nodosa; recurrent stenosis; Buerger's disease; or rheumatic fever); (5) respiratory diseases (for example, asthma; epiglottitis; bronchitis; emphysema; rhinitis; cystic fibrosis; Interstitial pneumonitis; COPD (chronic obstructive pulmonary disease); adult respiratory distress syndrome; coniosis; alveolitis; bronchiolitis; pharyngitis; pleurisy; or sinusitis); (6) bone, joint, muscle and connective tissue related diseases (for example, eosinophilic granuloma; arthritis; arthralgia; osteomyelitis; dermatomyositis; fasciitis; Paget's disease; gout; periodontal disease; rheumatoid arthritis; myasthenia gravis; ankylosing spondylitis; or synovitis); (7) urogenital disorders (for example, epididymitis; vaginitis; prostatitis; or urethritis); (8) central or peripheral nervous system related diseases (for example, Alzheimer's disease; meningitis; encephalitis; multiple sclerosis; cerebral infarction; cerebral embolism; Guillain-Barre syndrome; neuritis; neuralgia; spinal cord injury; paralysis; or uveitis); (9) virus (for example, influenza; respiratory syncytial virus; HIV; hepatitis B; hepatitis C; or herpes virus), infectious disease (for example, Dengue fever; or septicemia), fungal infection (for example, candidiasis); or bacterial, parasitic, and similar microbial infection (for example, disseminated bacteremia; malaria; onchocerciasis; or amebiasis); (10) autoimmune disease (for example, thyroiditis; lupus; Goodpasture's syndrome; allograft rejection; graft versus host disease; or diabetes); and (11) cancer or tumor disease (for example, Hodgkin's disease), but not limited to those.

Treating the inflammatory component of such diseases has been a major goal of the global pharmaceutical industry for a number of decades, and a wide variety of useful treatments have been developed. Examples include the corticosteroids (a range of natural, semisynthetic and synthetic agents designed to mimic the effect of cortisol, including prednisolone, methylprednisolone, dexamethasone, betamethasone, fluticasone and so forth), cyclooxygenase inhibitors (both non-selective or cox-1 selective, such as indomethacin, sulfasalzine and aspirin, and more recently cox-2 selective, such as celecoxib), leukotriene blockers (such as monteleukast) and anti-TNFs (such as modified monoclonal neutralising antibodies, including infliximab (Remicade™) and adalimumab (Humira™), TNF receptor fusion proteins, such as etanercept (Enbrel™), as well as small molecule TNF-α synthesis inhibitors like thalidomide).

In one embodiment of the present invention, an anti-inflammatory composition comprising a peptide as an active Ingredient is provided. The peptide comprises at least one amino acid sequence of SEQ ID NO: 2 to SEQ ID NO: 179, the peptide has above 80% homology with above-mentioned sequences, or the peptide is a fragment of the above-mentioned peptides.

In one embodiment of the present invention, the anti-inflammatory composition may contain 0.1 µg/mg to 1 mg/mg, specifically 1 µg/mg to 0.5 mg/mg, more specifically 10 µg/mg to 0.1 mg/mg of a peptide comprising of amino acid sequence of at least one of SEQ ID NO: 2 to SEQ ID NO: 179, a peptide comprising of amino acid sequence above 80% homology with above-mentioned sequences, or peptide fragment of above-mentioned peptides. When the peptide is contained in the above mentioned range, all the safety and stability of the composition may be satisfied and appropriate in terms of cost-effectiveness.

In one embodiment of the present invention, the composition may have application with all animals including human, dog, chicken, pig, cow, sheep, guinea pig, and monkey.

In one embodiment of the present invention, the medical composition for the use of treatment or prophylaxis of inflammatory disease with an active ingredient that is comprised of a peptide consisting of an amino acid sequence from SEQ ID NO: 2 to SEQ ID NO: 179, a peptide comprising of amino acid sequence above 80% homology with above-mentioned sequences, or peptide fragment of SEQ ID NO:1, is provided. In one embodiment of the present Invention, the pharmaceutical composition may be administered through oral, rectal, transdermal, Intravenous, intramuscular, intraperitoneal, in the bone marrow, epidural or subcutaneous means.

Forms of oral administration may be, but not limited to, tablets, pills, soft or hard capsules, granules, powders, solution, or emulsion. Forms of non-oral administration may be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition can be manufactured by conventional methods of the industry in the art.

In one embodiment of the present invention, the active ingredient of the medical composition may vary according to the patient's age, sex, weight, pathology and state, administration route, or prescriber's judgment. Dosage based on these factors is determined within levels of those skilled in the art, and the dally dose for example may be, but not limited to, 0.1 µg/kg/day to 1 g/kg/day, specifically 1 µg/kg/day to 10 mg/kg/day, more specifically the 10 µg/kg/day to 1 mg/kg/day, more specifically the 50 µg/kg/day to 100 µg/kg/day. In one embodiment of the present invention, the pharmaceutical composition may be administered, but not limited to, 1 to 3 times a day.

In one embodiment of the present invention, a skin external composition for improvement or prevention of skin inflammation is provided. The skin external composition may contain an active ingredient that is a peptide comprising of an amino acid sequence from SEQ ID NO: 2 to SEQ ID NO: 179, a peptide comprising of amino acid sequence above 80% homology with above-mentioned sequences, or peptide fragment of above-mentioned peptides.

In another embodiment of the present invention, a cosmetic composition for improvement or prevention of skin inflammation is provided. The cosmetic composition may contain an active Ingredient that Is a peptide comprising of an amino acid sequence from SEQ ID NO: 2 to SEQ ID NO: 179, a peptide comprising of amino acid sequence above 80% homology with above-mentioned sequences, or peptide fragment of above-mentioned peptides.

In one embodiment of the present invention, external application composition or cosmetic composition may be provided in all forms appropriate for topical applications. For example, forms can be provided as solutions, emulsions obtained by dispersion of oil phase in water, emulsion obtained by dispersion of water in oil phase, suspension, solid, gel, powder, paste, foam or aerosol. These forms can be manufactured by conventional methods of the industry in the art.

In one embodiment of the present invention, the cosmetic composition may include, within levels that will not harm the main effect, other ingredients that can desirably increase the main effect. In one embodiment of the present Invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients can be decided by those skilled in the art within levels that will not harm the purpose and the effects of the present Invention, and the formulation ratio based on total weight of the cosmetic composition can be 0.01 to 5% by weight, specifically 0.01 to 3% by weight.

In one embodiment of the present invention, a food composition for inflammation prevention or suppression is provided. The food composition may contain with an active ingredient that is a peptide comprising of an amino acid sequence from SEQ ID NO: 2 to SEQ ID NO: 179, a peptide comprising of amino acid sequence above 80% homology with above-mentioned sequences, or peptide fragment of above-mentioned peptides.

In one embodiment of the present invention, food composition is not limited to forms, but for example may be granules, powder, liquid, and solid forms. Each form can be formed with Ingredients commonly used in the industry appropriately chosen by those skilled in the art, in addition to the active ingredient, and can increase the effect with other Ingredients.

Decision for dosage on the above-mentioned active ingredient is within the level of those skilled in the art, and daily dosage for example may be 1 μg/kg/day to 10 mg/kg/day, more specifically the 10 μg/kg/day to 1 mg/kg/day, more specifically the 50 μg/kg/day to 100 μg/kg/day, but not limited to these numbers and can vary according to age, health status, complications and other various factors.

In one embodiment of the present invention, a use of prevention or treatment of inflammatory disease with a peptide comprising of an amino acid sequence from SEQ ID NO: 2 to SEQ ID NO: 179, a peptide comprising of amino acid sequence above 80% homology with above-mentioned sequences, or peptide fragment of above-mentioned peptides, is provided.

In one embodiment of the present invention, the method of prevention or treatment of inflammatory disease with applying peptides mentioned above in patients is provided.

In one embodiment of the present invention, a kit for prophylaxis or treatment of inflammatory diseases is provided. The kit may contain: a peptide with anti-inflammatory activity or a composition comprising of the peptide, wherein the peptide comprises any one amino acid sequence of SEQ ID NO: 2 to SEQ ID NO: 179, the peptide has above 80% homology with above-mentioned sequences, or the peptide is a fragment of the above-mentioned peptides; and Instructions including at least one of administration dose, administration route, administration frequency, and indication of the peptide or composition.

The terms used herein is Intended to be used to describe the embodiments, not to limit the present invention. Terms without numbers in front are not to limit the quantity but to show that there may be more than one thing of the term used. The term "Including", "having", "consisting", and "comprising" shall be Interpreted openly (i.e. "including but not limited to").

Mention of range of numbers is used instead of stating separate numbers within the range, so unless it is explicitly stated, each number can be read as separate numbers integrated herein. The end values of all ranges are included in the range and can be combined independently.

Unless otherwise noted or clearly contradicting in context, all methods mentioned herein can be performed in the proper order. The use of any one embodiment and all embodiment, or exemplary language (e.g., that use "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meaning normally understood by a person skilled in the art that the present invention belongs to.

The preferred embodiments of the present invention are the best mode known to the inventors to perform the present invention. It may become clear to those skilled in the art after reading the statements ahead of the variations in the preferred embodiments. The present inventors hope that those skilled in the art can use the variations adequately and present invention be conducted in other ways than listed herein. Thus, the present invention, as allowed by the patent law, includes equivalents, and variations thereof, of the key points of the invention stated in the appended claims. In addition, all possible variations within any combination of the above-mentioned components are included in the present Invention, unless explicitly stated otherwise or contradicting in context. Although the present Invention is described and shown by exemplary embodiments, those skilled in the art will understand well that there can be various changes in the form and details without departing from the spirit of the Invention and range, defined by the claims below.

Tumor necrosis factor (TNF), particularly TNF-α, is known to be released from inflammatory cells and cause various cytotoxic reactions, Immunological reactions and inflammatory reactions. TNF-α is known to be involved in the occurrence and prolongation of many inflammatory and autoimmune diseases and further cause serious septicemia and septic shock when it is released into the blood and acts systemically. Because TNF-α is a factor associated widely with the immune system of a living body, the development of agents inhibiting TNF-α is actively carried out. TNF-α is biosynthesized in an inactive form and becomes an active form by being cleaved by protease; the enzyme responsible for the activation is called a tumor necrosis factor-converting enzyme (TACE). Thus, a substance inhibiting this TACE can treat, improve, or prevent diseases, pathologic conditions, abnormal conditions, troubles, adverse symptoms and the like ascribed to TNF-α (KR2011-0060940A).

High-mobility group box 1 (HMGB1) protein exists in high concentrations in thymus, lymph nodes, testes, and in fetal liver, and with exception to liver and brain cells, usually exists inside of the nucleus. The said HMGB1 protein has 3 domains consisting of A-box, B-box, and C-terminal.

It was reported by Tracey et al., 1999 that HMGB1 protein has a role as a cytokine which induces inflammation, and the mechanism of said HMGB1's inflammation induction is by an external stimulus causing acetylation of HMGB1 which then moves from the nucleus into the cytoplasm. Afterward, it is known to be secreted out of the cell, or secreted out from the cell in necrosis. (Bonaldi T et al., EMBO J, (22)5551-60, 2003).

The invention is further described by the figures, the following examples and experiments, which are solely for the purpose of Illustrating specific embodiments of this Invention, and are not to be construed as limiting the scope of the Invention in any way.

Example 1

Synthesis of PEP-1 and Measurement of Anti-Inflammatory Activities of PEP-1 (SEQ ID NO: 1)

Experiment 1. Synthesis of PEP-1 (SEQ ID NO: 1)

A peptide comprised of 16 aminoacids with the chemical structure 1 as below having the sequence SEQ ID: 1 (PEP-1) derived from human telomerase was synthesized:

<Chemical Structure 1>

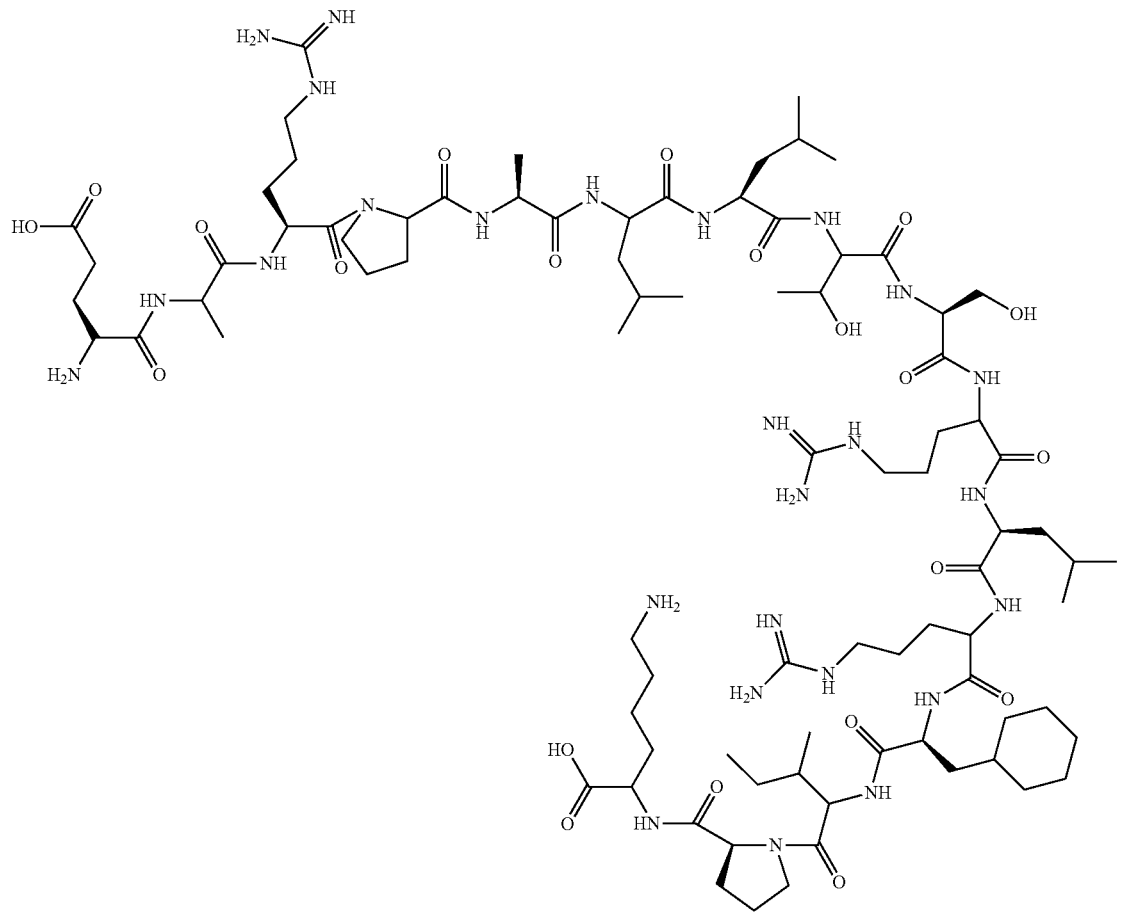

SEQ ID NO: 1 (PEP-1) was synthesized according to the existing method of solid phase peptide synthesis. In detail, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to resin were used as follows:

NH$_2$-Lys(Boc)-2-chloro-Trityl Resin
NH$_2$-Ala-2-chloro-Trityl Resin
NH$_2$-Arg(Pbf)-2-chloro-Trityl Resin All the amino acid materials to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in acid. Such as:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetamethylaminium hexafluorophosphate]/HOBt [N-Hydroxybenzotriazole]/NMM [4-Methylmorpholine] were used as the coupling reagents. In 20% of DMF, piperidine was used to remove Fmoc. In order to remove the protection from residue or to separate the synthesized peptide from Resin, cleavage cocktail [TFA (trifluoroacetic acid)/TIS (trisopropylsilane)/EDT (ethanedithiol)/H$_2$O=92.5/2.5/2.5/2.5] was used.

Synthesized the peptide by using the solid phase scaffold combined to starting amino acid with the amino acid protection, reacting the corresponding amino acids separately, washing with solvent and deprotected, and repeating the process. After cutting off the synthesized peptide from the resin, it was purified by HPLC and verify for synthesis by MS, and then freeze-dried.

Specific synthesis process of PEP 1 is described by the following.

1) Coupling

Melted the amino acid (8 equivalent) protected with NH$_2$-Lys(Boc)-2-chloro-Trityl Resin, and coupling agent HBTU (8 equiv.)/HOBt (8 equiv.)/NMM (16 equiv.) and added to DMF, then let react in room temperature for 2 hours, then washed with DMF, MeOH, and DMF In that order.

2) Fmoc Deprotection

Added 20% piperidine in DMF and reacted in room temperature for 5 minutes 2 times, then washed with DMF, MeOH, and DMF in that order.

3) Make the basic framework of peptide by repeating reactions 1 and 2 repeatedly.

4) Cleavage: Add Cleavage Cocktail to the completely synthesized peptide and separated the peptide from the resin.

5) Add cooling diethyl ether into obtained mixture, and then centrifugation is used to precipitate gathered peptide.

6) After purification by Prep-HPLC, check the molecular weight by LC/MS and lyophilize to produce in powder form.

Experiment 2: Anti-Inflammatory Activity Measurement of PEP 1

Cell Lines Culture

Raw 264.7 macrophage cell (KCBL, 40071) from Korea Cell Bank was maintained in Dulbecco's modified Eagle's medium (DMEM; PAA, Austria) containing 10% fetal bovine serum (FBS; Gibco Laboratories), 100 unit/mL of streptomycin, and penicillin (Gibco Laboratories) at 37° C. with 5% $CO_2$. Raw 264.7 cells were seeded into a 96-well plate at a density of $1\times10^6$ cells/mL and incubated overnight.

On the following day, the medium was replaced with fresh medium and 5 μg/mL of peptide (obtained as described in Experiment example 1) was added to the cells. After 30 min incubation of cells with the peptide 50 μl of LPS (to a final concentration of 1 μg/mL) was added, and cells were Incubated for additional 24 hr. The experimental sample with the Induction of Inflammatory response was treated with 1 μg/mL mL lipopolysaccharide (LPS; Sigma, USA) and control sample was treated with phosphate buffered saline (PBS; pH 7.2). The supernatant samples from each condition was collected in eppendorf tubes and subjected to further analysis.

Experiment 2-1, NO Level Analysis

The level of nitric oxide (NO) was measured in Raw 264.7 cell ($1\times10^4$ cell/m) using Griess reagent system (Promega, USA). Culture medium of 50 μl was added to a 96-well plate and Griess reagent I (NED) solution and Griess reagent II (Sulfaniliamide solution) are added in the same amount. After 10 min incubation of cells with the reagents, the optical density at 540 nm was measured within 30 min using a microplate reader (Molecular Devices, USA). The concentration of NO was calculated by using a standard curve (0-100 μM) of sodium nitrite.

As shown in Table 3 below, stimulation of cells with LPS Increased the expression of NO, but in co-treatment with LPS and Pep1, the expression level of NO mentioned above decreased. NO is produced during Inflammation, and the result showing Pep1 reduced NO level to 65% of the control strongly support the anti-Inflammatory effect of Pep1.

TABLE 3

The measurement of anti-inflammatory effect of human telomerase derived PEP 1

| Test sample | | NO Expression Level of control (%) | Decreased NO Expression Level (%) |
|---|---|---|---|
| | PBS | 0 | — |
| LPS 1 μg/mL | PBS | 100 | 0 |
| | PEP 1 (0.5 μg/mL) | 35 | 65 |

Experiment 2-2, Analysis of Cytokine Inhibitory Effect

To Investigate the effect of PEP1 on inhibiting proinflammatory cytokine production RAW 264.7 cell were pre-treated with PEP 1 at a concentration of 5 μg/mL challenged with LPS at a concentration of 1 μg/mL, and cells were further incubated for 24 hr. The supernatant samples containing cell culture medium was collected and analyzed for the cytokine levels using ELISA kits (eBioscience, San Diego).

96 wells plates were coated with 100 μL of capture antibodies (diluted in coating buffer to the concentration recommended by manufacturer's protocol) overnight at 4° C. Then, after washing the plates 5 times, 200 μl of assay diluents was added to each well and incubated for 1 hr at room temperature for blocking. After washing each well with wash buffer five times, cell culture sample or each cytokine standard protein sample was diluted and 100 μl of each added into each well. The plate containing samples were Incubated overnight at 4° C. Then, after washing the plate five times with the wash buffer, 100 μl of secondary antibody conjugated to avidin was added and incubated for 1 hr at room temperature.

Following incubation with the secondary antibody, the plate was washed five times and incubated with 100 μl of avidin-HRP (BD Bioscience) for 30 min at room temperature. After washing the plate seven times, 100 μl of TMB solution (Pierce) was added and Incubated for 15 min at room temperature. The reaction was stopped by adding 50 μl of 2N $H_2SO_4$ in each well The optical density at 450 nm was measured using a microplate reader. Statistical analysis was performed by variance analysis using ANOVA procedure of SPSS program, and verified the significance between analyses using Duncan's multiple range test.

Experiment 2-3. IL-6 Secretion Measurement

As shown in Table 4 below, treatment with LPS alone increased the cytokine IL-6 (interleukin-6) secretion. However, co-treatment with LPS and PEP-1 showed a decrease in the level of the proinflammatory cytokine IL-6 secretion. More Importantly, after the treatment with PEP-1, the level of proinflammatory cytokine secretion decreased by more than 70%, which indicates a robust anti-inflammatory effect of Pep1.

TABLE 4

Cytokine IL-6 production inhibition by PEP-1

|  | Test sample | cytokine IL-6 production | |
|---|---|---|---|
|  |  | % of control | inhibition % |
| LPS 1 µg/ml | PBS | 0 | — |
|  | PBS | 100 | 0 |
|  | PEP 1 (5 µg/ml) | 28 | 72 |

Experiment 2-4. HMGB1. TNF-α, COX-2 Expression Inhibition

Protein expression level was determined by Western blot analysis. Cells grown in PEP-1 containing medium were washed with PBS, treated with 0.05% trypsin-EDTA, and collected by centrifugation. The collected cells were dissolved in an appropriate volume of lysis buffer. Intracellular debris was pelleted by centrifugation, and equal amount of protein from each sample was separated by SDS-polyacrylamide gel electrophoresis. The separated protein was transferred to nitrocellulose membrane (Schleicherand Schuell, Keene, N.H., USA), then was tested for the antibody specific for each protein. The membrane was incubated with ECL (enhanced chemiluminoesence) solution (Amersham Life Science Corp., Arlington Heights, Ill., USA), exposed to X-ray, and the level of protein expression was analyzed according to the exposure level shown on the X-ray film.

Western blot analysis was performed to determine the inhibitory effect of Ppep1 on the cytokine protein expression. As shown in Table 5 below, stimulation of cells with LPS increased the expression of cytokines; HMGB1, TNF-α and COX. However, if cells were treated with both LPS and Pep1, the expression level of pro-inflammatory cytokines mentioned above decreased. The result showing the treatment with Pep1 decreased pro-Inflammatory cytokine levels by more than 70% provide strong evidence supporting the anti-inflammatory effect of Pep1.

TABLE 5

The measurement of inhibitory effect of PEP-1 on pro-inflammatory cytokine expression level.

|  | Test sample | Cytokine Expression Level (band intensity) % of control | | |
|---|---|---|---|---|
|  |  | HMGB1 | TNF-α | COX-2 |
| LPS 1 µg/ml | PBS | — | — | — |
|  | PBS | 100 | 100 | 100 |
|  | PEP 1 (5 µg/ml) | 30 | 25 | 22 |

Experiment 3: Investigation of the Inhibitory Effect of Pep1 on TNF-α Level in HepG2 Cells Experiment 3-1: Cell Culture PBMC (peripheral blood mononuclear cell) was separated from the blood samples (50 ml) collected from healthy subjects using Ficoll-Paque™ PLUS (GE Healthcare Life Sciences, Piscataway, N.J., USA). PBMCs were then enriched in complete RPMI 1640 medium containing 20% of human serum, followed by transferring to 100 mm polystyrene cell culture plate coated with human serum for 30 mins. After 2 hr incubation at 37° C. and 5% $CO_2$, the monocytes were detached from the bottom of cell culture plate using cold PBS (Phosphate Buffered Saline) (Gibco/Life Technologies, Carlsbad, Calif., USA), and $1 \times 10^5$ cells were cultured in each well of 96-well plate in RPMI 1640 medium (supplemented with penicillin-streptomycin; 100 mg/ml, human serum; 20%) over night.

For Luciferase Analysis, HEK293/null (human embryonic kidney) cells and HEK293/TRL stably expressing TLR2 (toll-like receptor 2) obtained from Seoul National University School of Dental Medicine were used. One day before the luciferase experiment, $2.5 \times 10^5$ cells were seeded into each well of 12-well plate and cultured overnight in DMEM (Dulbecco's modified Eagle's medium) medium (supplemented with blasticidin; 10 µg/ml, fetal bovine serum; 10%)(Invitrogen/Life Technologies, Carlsbad, Calif., USA)

Experiment 3-2: Cytokine Assay

To see the effect of PEP-1 on TNF-α level in terms of protein expression level, ELISA (enzyme linked immunosorbent assay) was performed. $1 \times 10^5$ PBMC-derived monocytes were cultured in 96-well plate over night. After then, LPS (lipopolysaccharide; 10 ng/mi, Sigma) was treated for 2 hours, followed by 3 times washes with PBS. OPTI-MEM medium (Invitrogen/Life Technologies, Carlsbad, Calif., USA) was then treated for an hour to induce the starvation, and 4 µM of FITC (Fluorescein Isothiocyanate), FITC-TAT, PEP-1-FITC, and FITC-PEP-1 were treated for 2 hours before measuring the TNF-α level. After culturing, cell soup was collected, and the amount of TNF-α was measured using ELISA kit (R&D, Minneapolis, Minn., USA) as follows:

TNF measurement uses sandwich ELISA method. 100 µl of TNF-α primary antibody was added into each well of pre-coated 96-well plate, and the plate was incubated at 4° C. overnight. On next day, the plate was washed 3 times with 0.5% Tween20 wash solution for 5 min each, and then 100 µl of each sample and standard solution was added and left at room temperature for 2 hrs. After washing the plate like above, 100 µl of HRP-conjugated secondary antibody was added into each well and left at room temperature for 2 hrs. Again, plate was washed, and avidin/biotin was added for measuring the absorbance. TNF-α level of each sample was quantified using the standard graph calculated from the absorbance of standard solution.

PBMC-derived monocytes were stimulated with endotoxin LPS (10 ng/ml) for 2 hrs, starved for 1 hr using OPTI-MEM, and then 4 µM of FITC, FITC-TAT, PEP 1-FITC and FITC-PEP 1 were treated for 2 hrs. After Incubation, TNF-α level was measured with cell culture medium using ELISA. As a result, in case of FITC and FITC-TAT, TNF-α level Increased due to LPS (6.2 and 6.7 ng/ml, respectively), but TNF-α level significantly decreased in case of PEP-1-FITC and FITC-PEP-1 (0.17 and 0.25 ng/ml, respectively) and the difference was statistically significant ($P<0.01$) (FIG. 1).

Experiment 3-3: Luciferase Assay

To investigate the role of PEP 1 in inflammatory response, we evaluated NF-kB expression patterns through luciferase analysis. First, we incubated HEK293/null and HEK293/TLR2 (Graduate School of Dentistry, Seoul National University) in a 12-well plate for 24 hours, so that we would get $2.5 \times 10^5$ cells/well. After washing three times with PBS, medium was replaced with OPTI-MEM (Invitrogen/Life Technologies, Carlsbad, Calif., USA) and incubated for 4 hours, and then a mixture of 3 µl lipofectamine (Invitrogen/Life Technologies), 1 µg NF-kB luciferase and 10 ng *renilla* luciferase (Promega, Madison, Wis., USA) was added into each well and again Incubated for 4 hours. Lipoprotein pam3cys (10 ng/mi, Sigma-Aldrich, St. Louis, Mo., USA) was put into all of the wells except for those of negative control, and FITC (4 µM) and FITC-PEP 1 (4 µM) were treated for 18 hours before it was washed with PBS for three times. We confirmed the activation of NF-kB through TD-20/20 luminometer (Turner designs, Sunnyvale, Calif., USA) after dissolving (lysis) of cells by putting 50 µl of passive lysis buffer-provided by dual-luciferase reporter assay system (Promega)—into each well. Transfection efficacy was confirmed by cotransfection of pCMV-*renilla* luciferase(Promega), and we analyzed results by calibrating the luciferase values.

Figure 2:
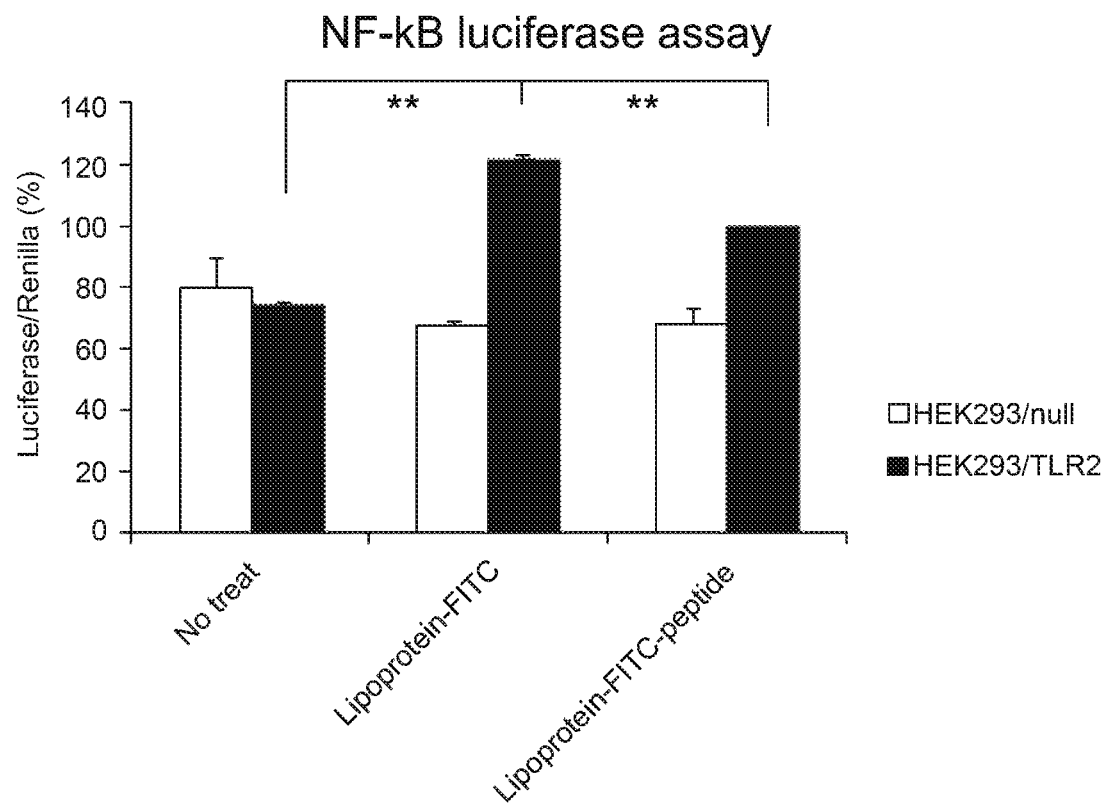
FIG. 2 is a graph which shows the results of performing luciferase analysis from transfecting HEK293/null and HEK293/TLR2 cell lines with NF-kB luciferase, then reacting with lipoprotein (10 ng/ml) and FITC and FITC-PEP1 (4 μM), and incubating for 18 hours. Results of luciferase were obtained by correction using *renilla*. (** P<0.01, compared to the negative control (No treat) and compared with lipoprotein treated sample.)
Figure 3:
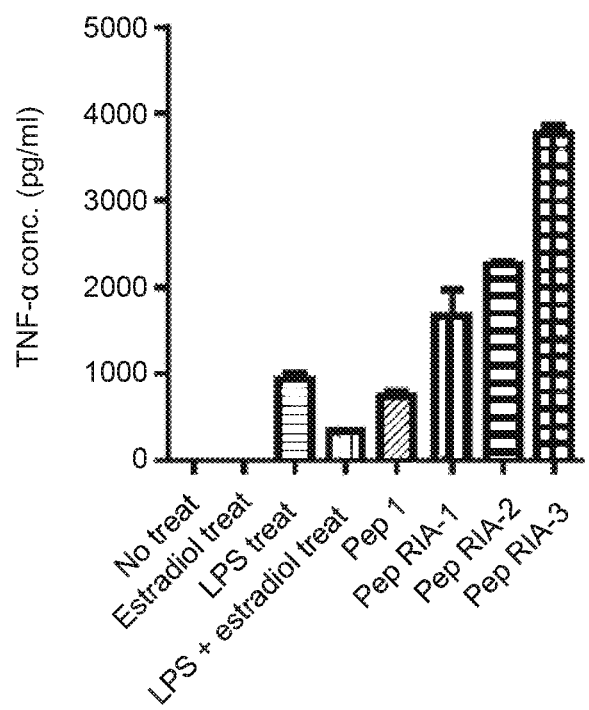
FIG. 3 to FIG. 23 are results from screening TNF-α inhibition effects on monocytes.
Figure 4:
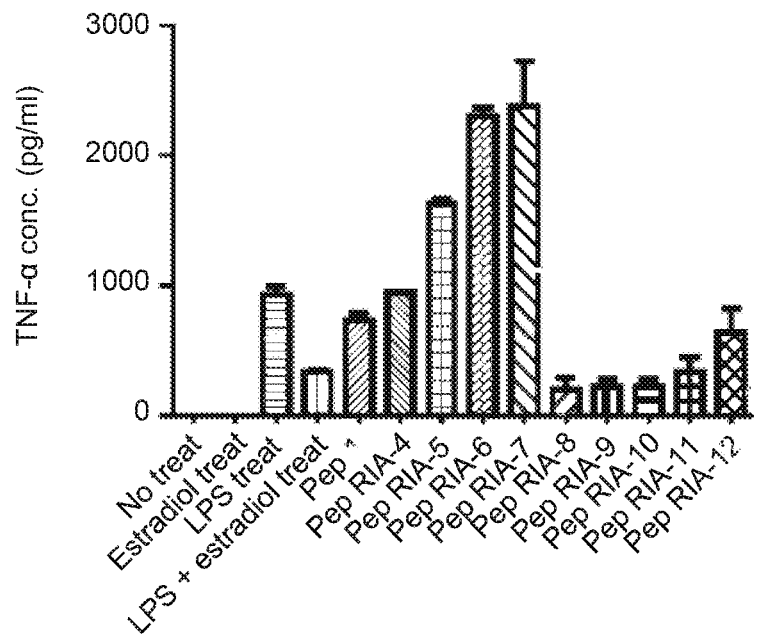
Figure 5:
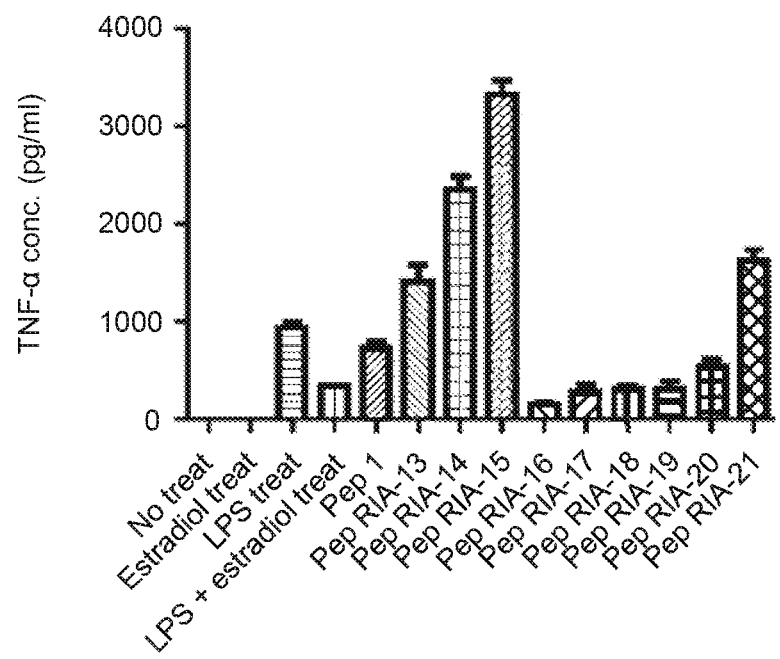
Figure 6:
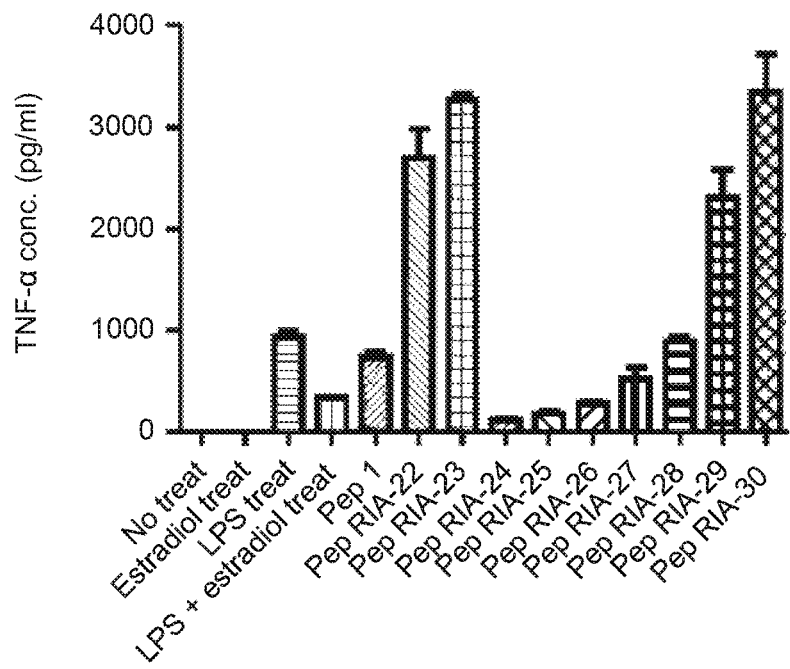
Figure 7:
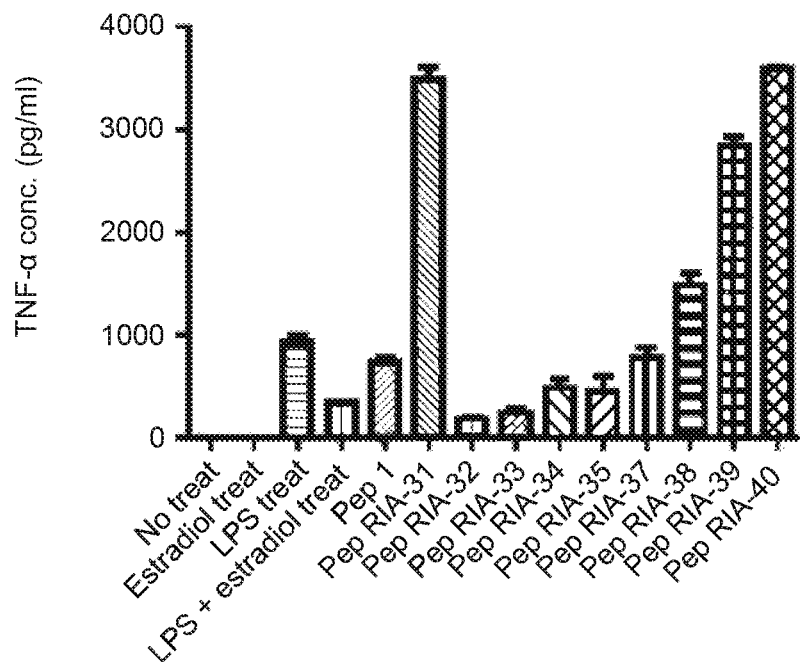
Figure 8:
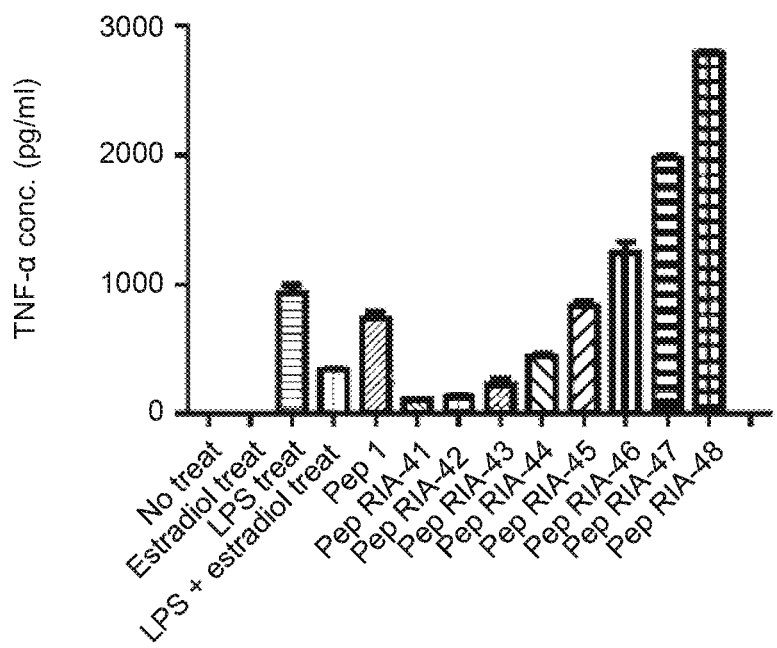
Figure 9:
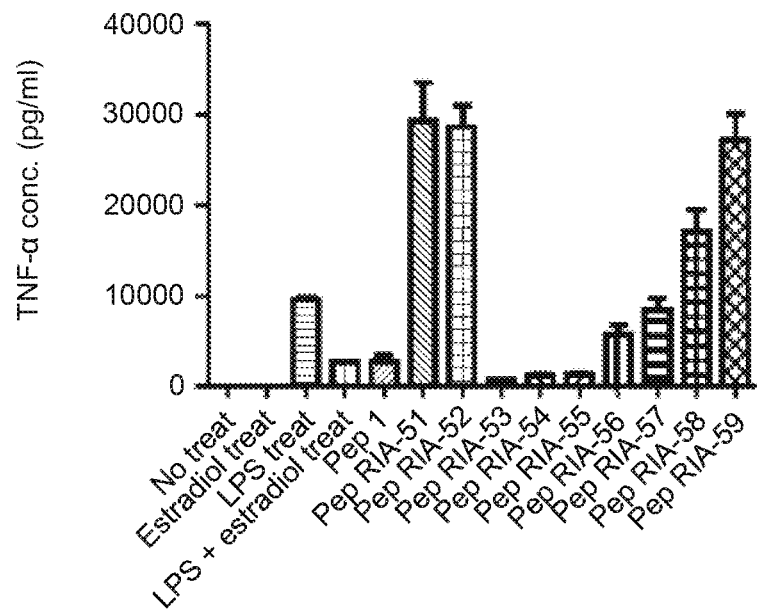
Figure 10:
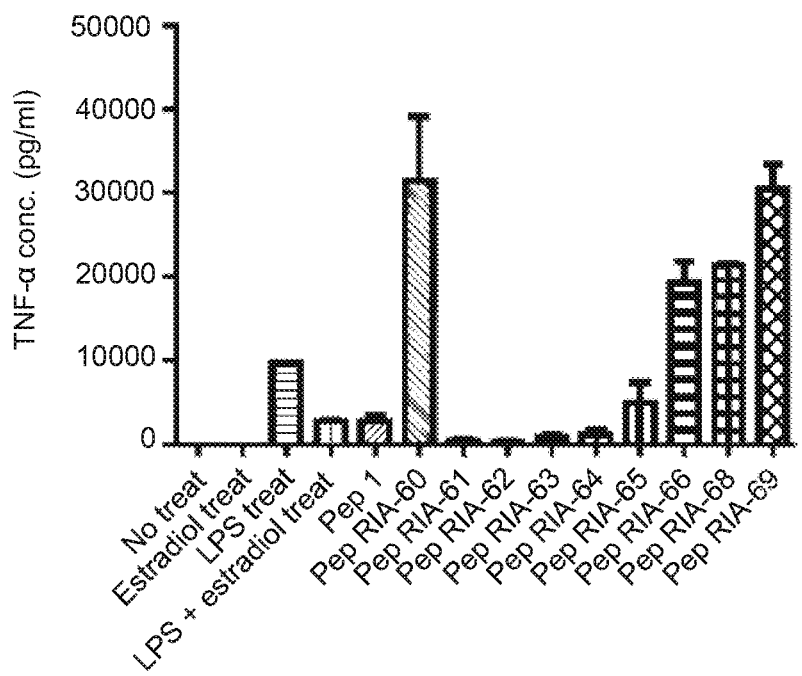
Figure 11:
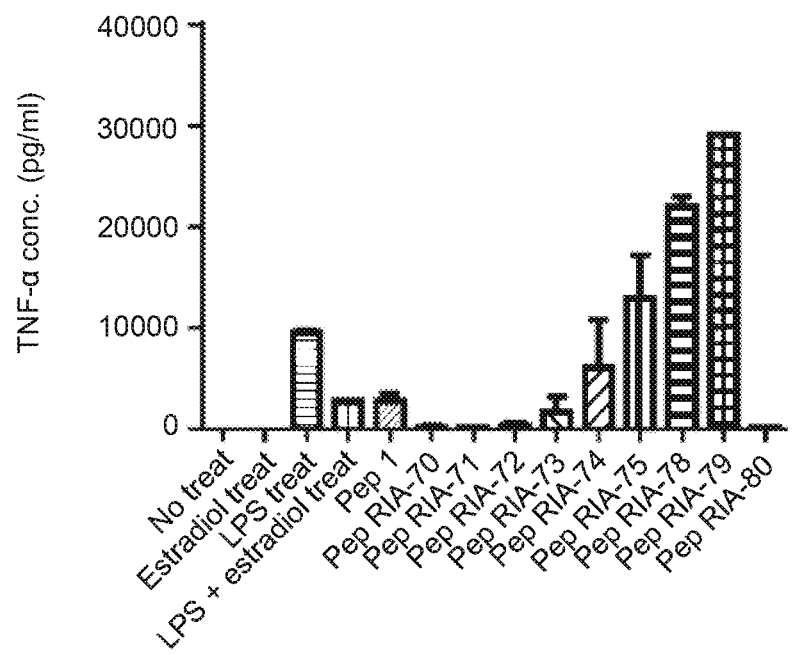
Figure 12:
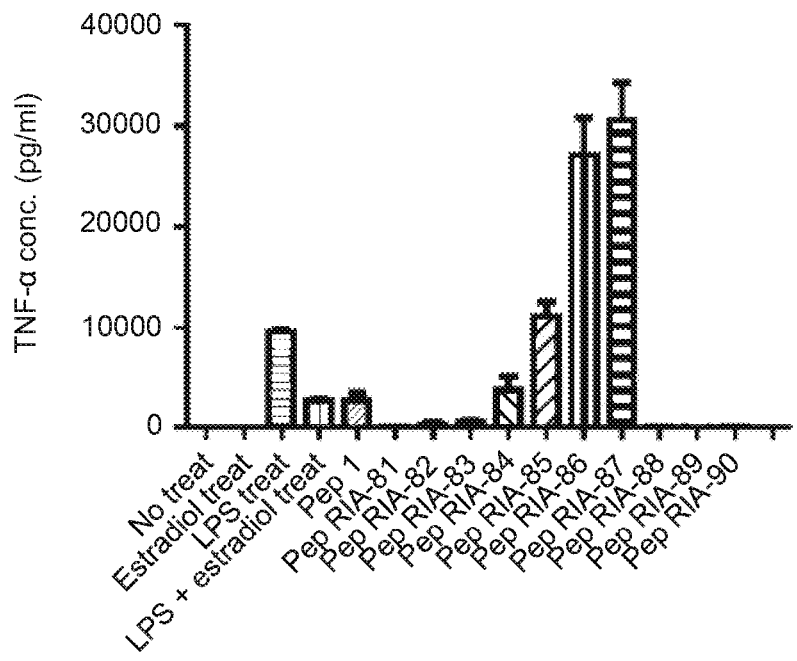
Figure 13:
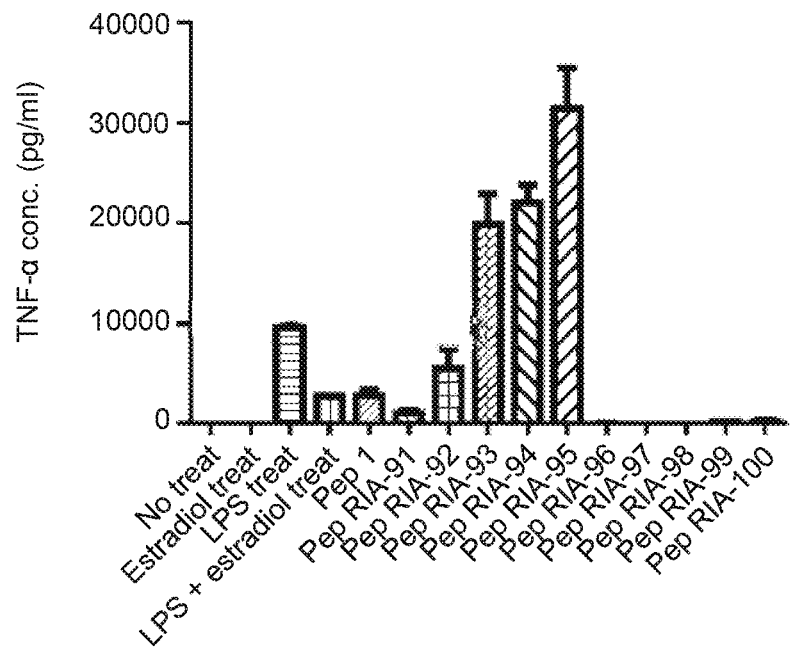
Figure 14:
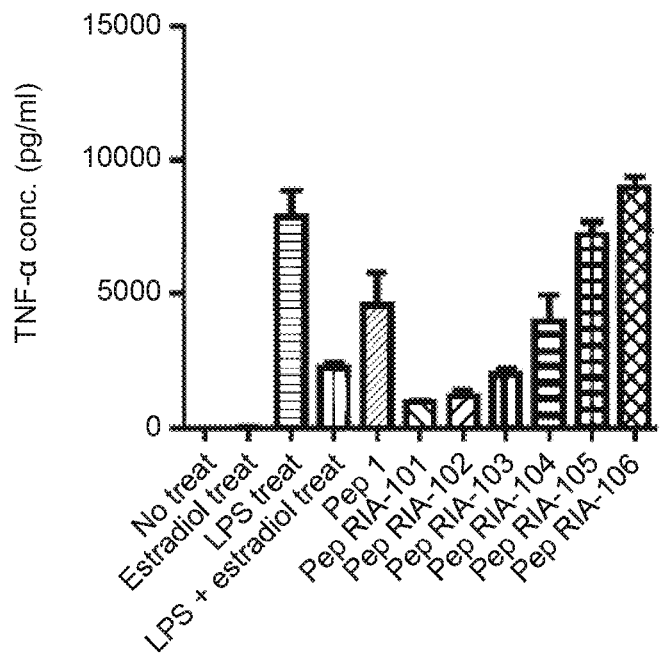
Figure 15:
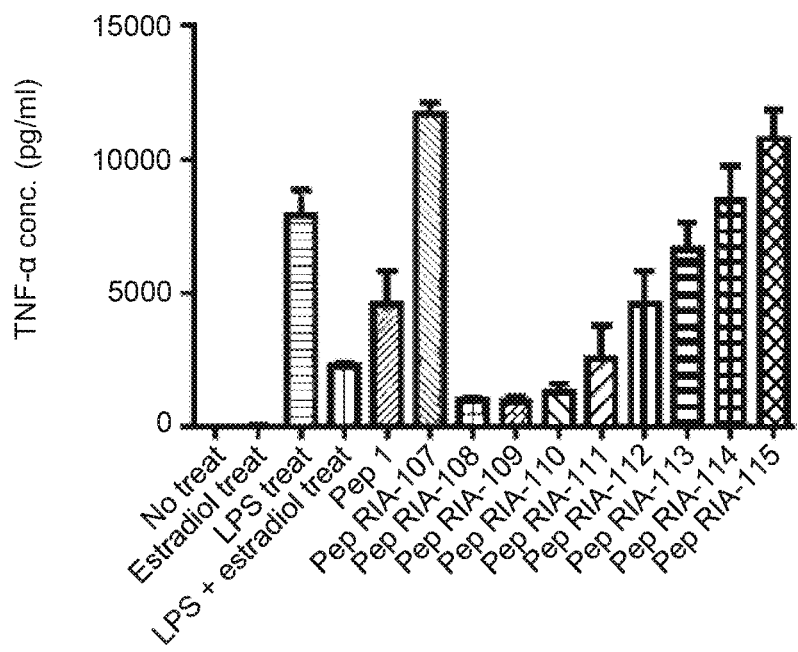
Figure 16:
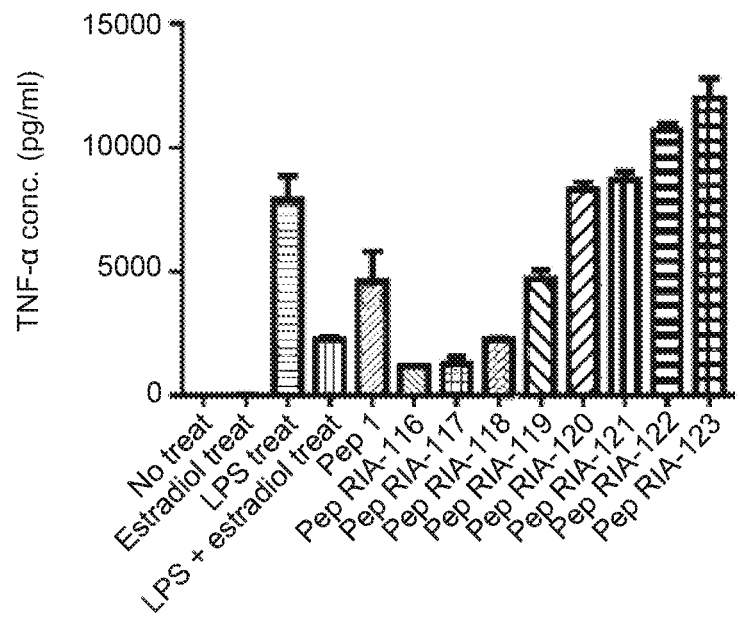
Figure 17:
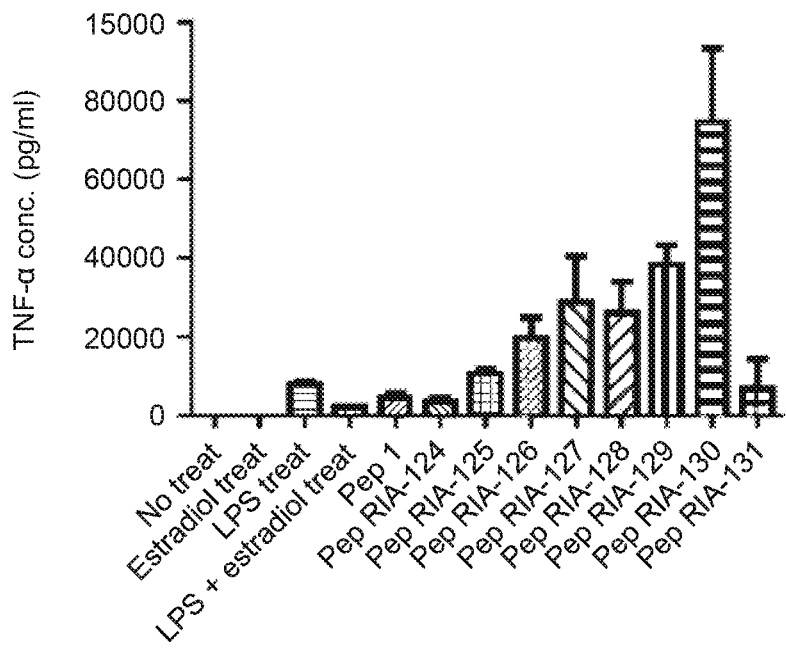
Figure 18:
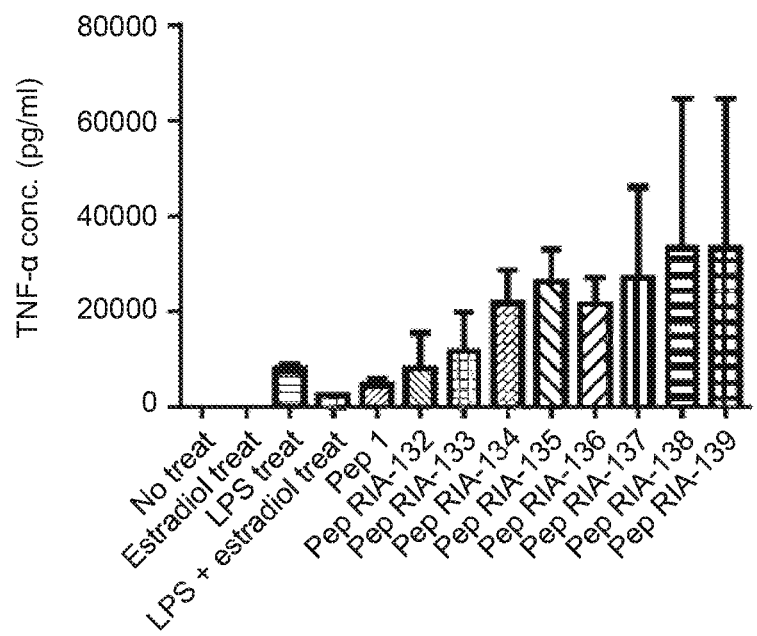
Figure 19:
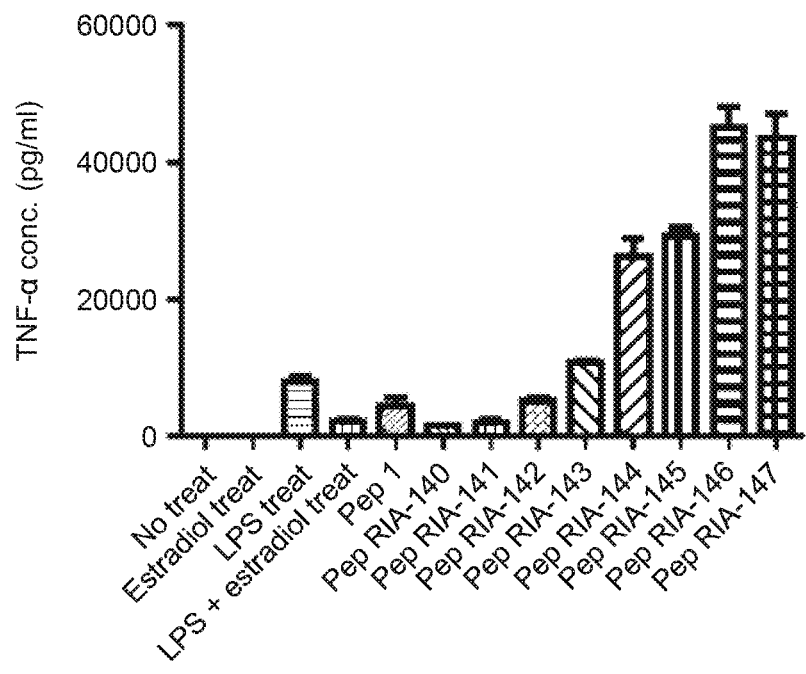
Figure 20:
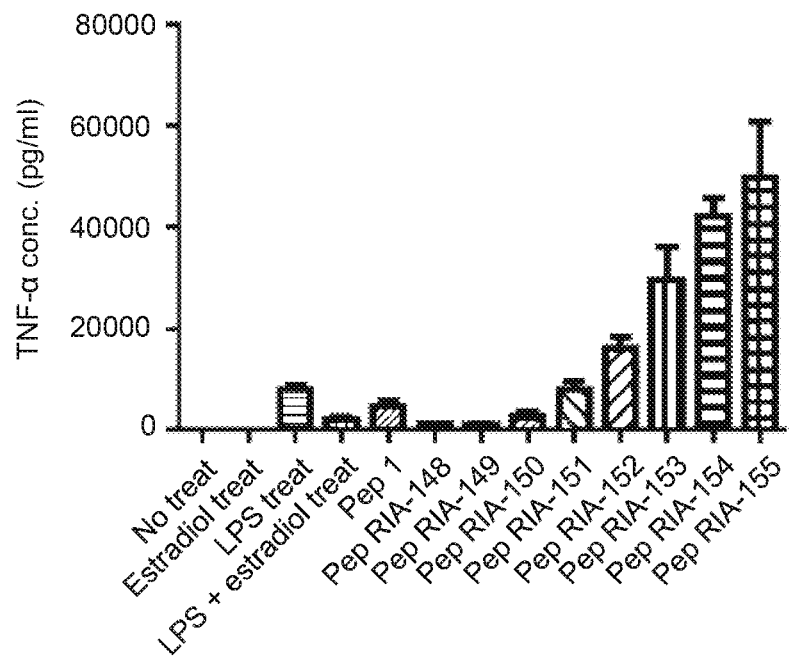
Figure 21:
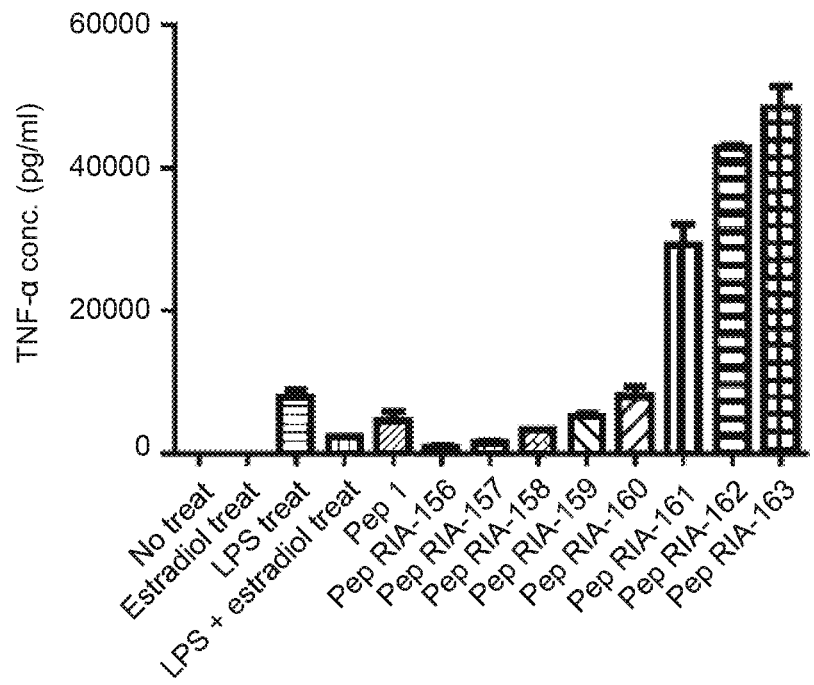
Figure 22:
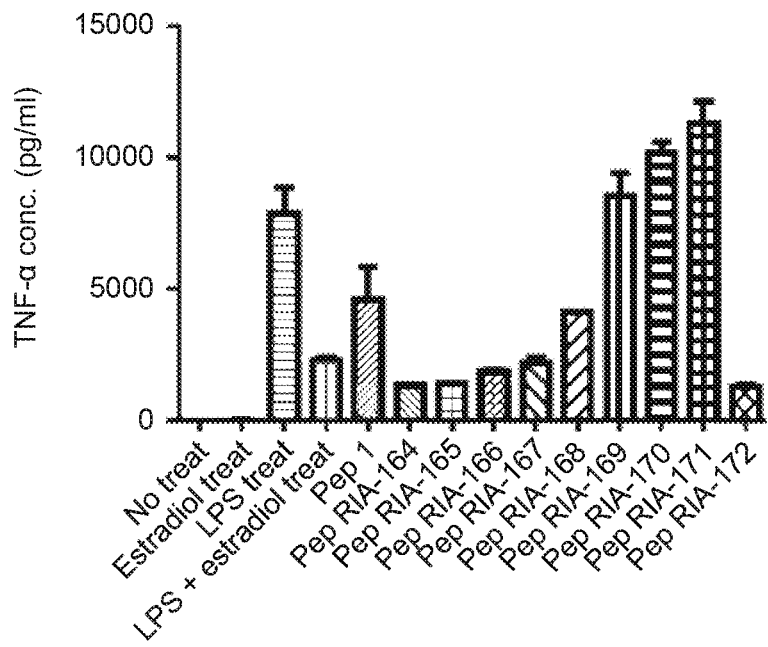
Figure 23:
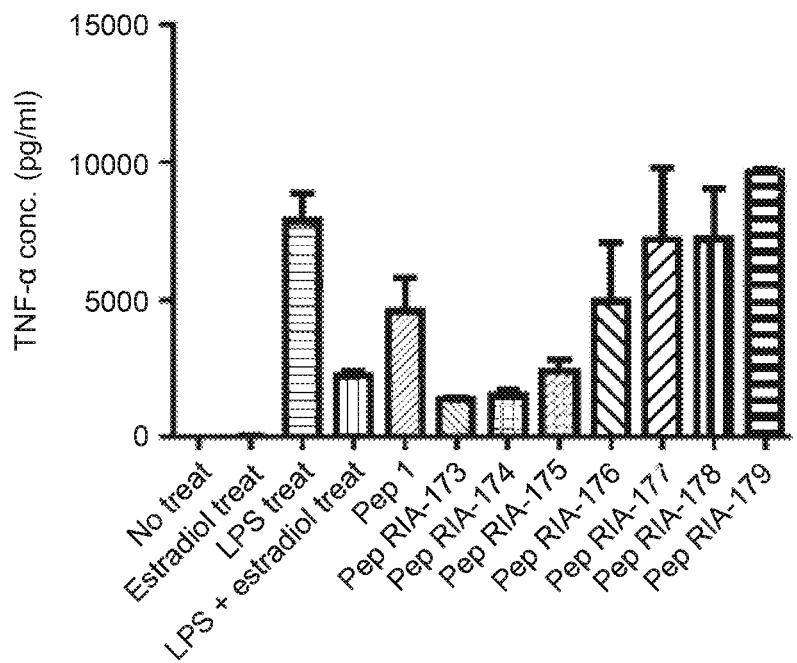
Figure 24:
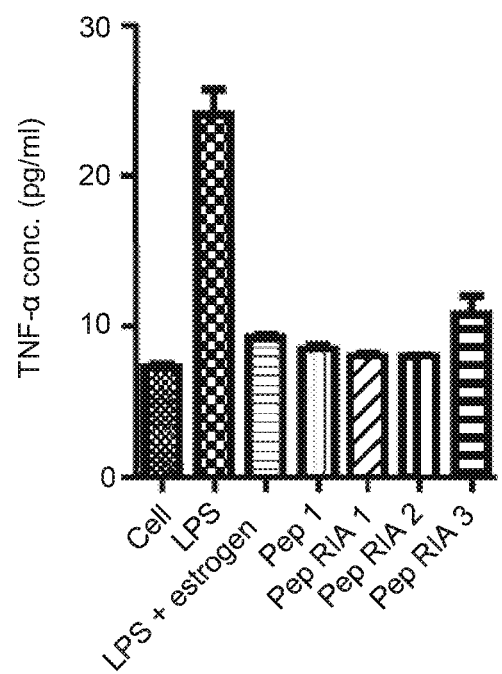
FIG. 24 to FIG. 46 are results from screening TNF-α inhibition effects on cell line THP-1.
Figure 25:
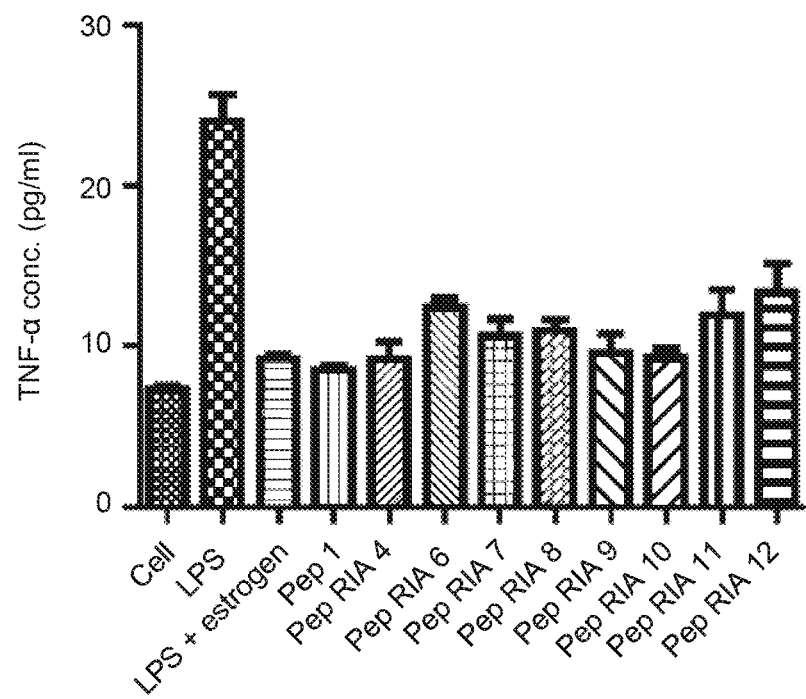
Figure 26:
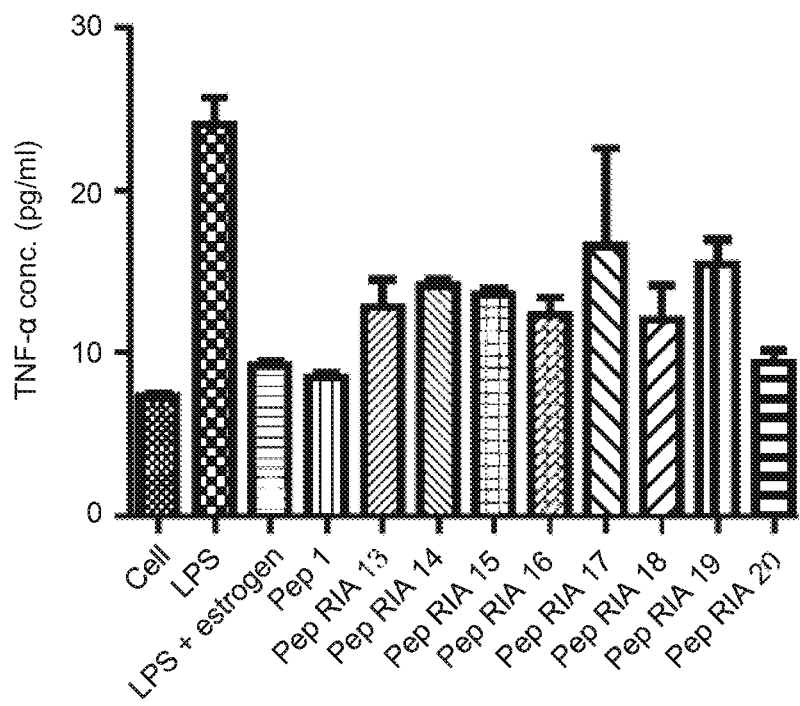
Figure 27:
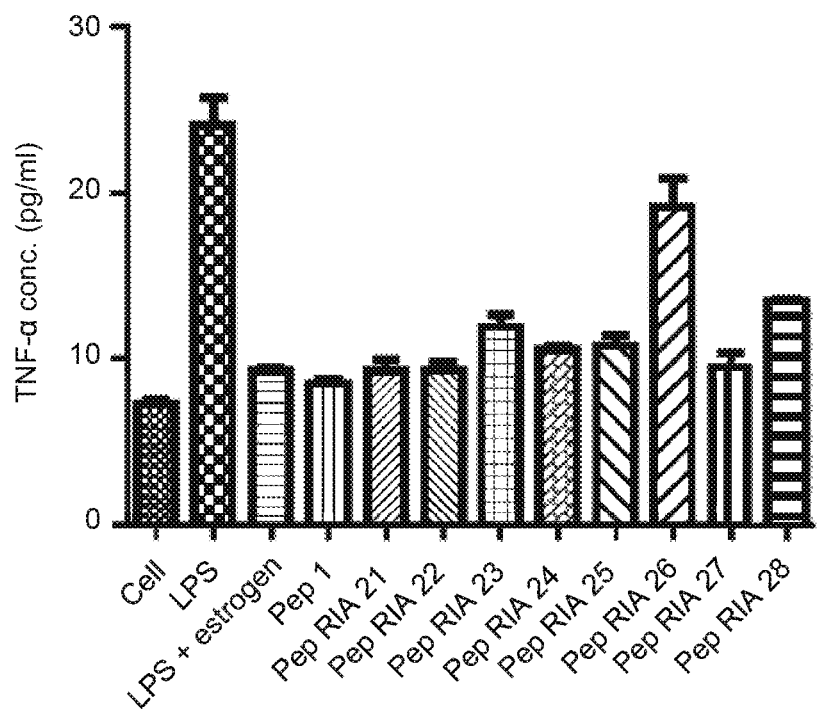
Figure 28:
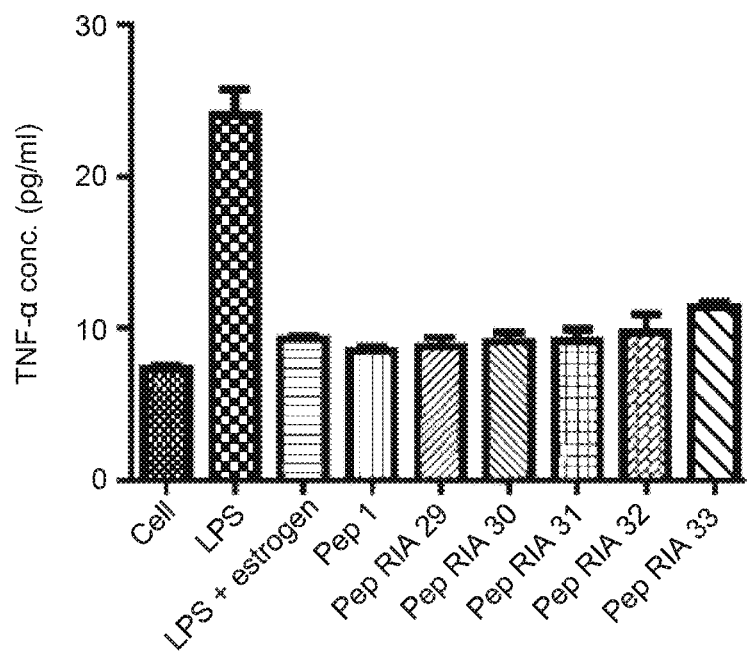
Figure 29:
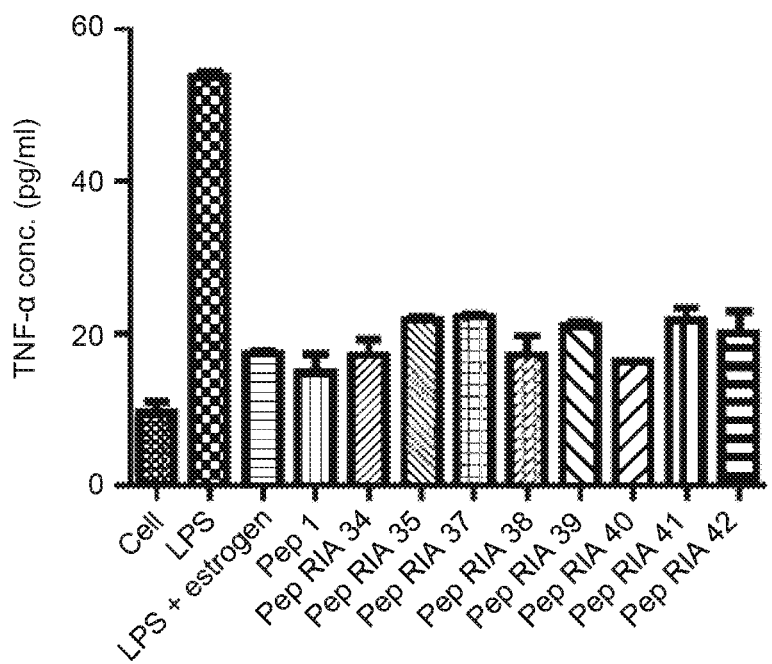
Figure 30:
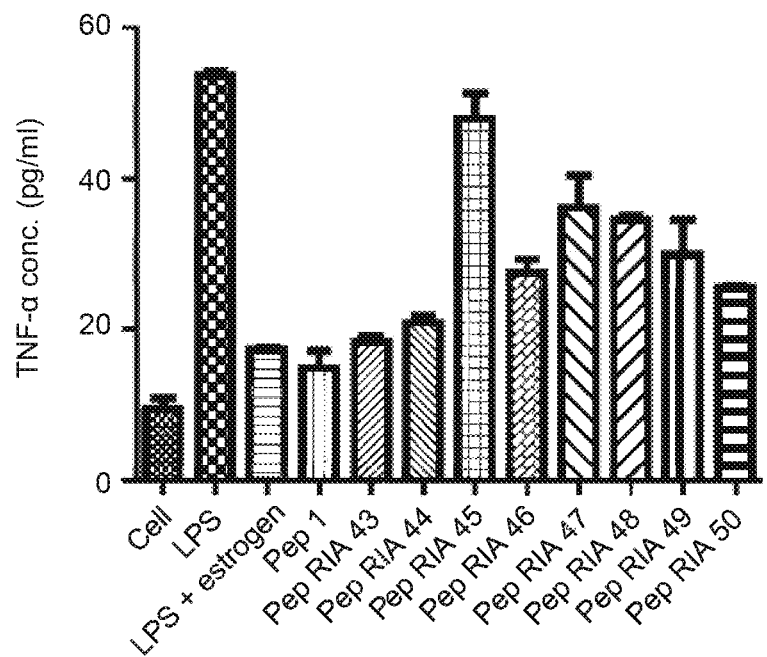
Figure 31:
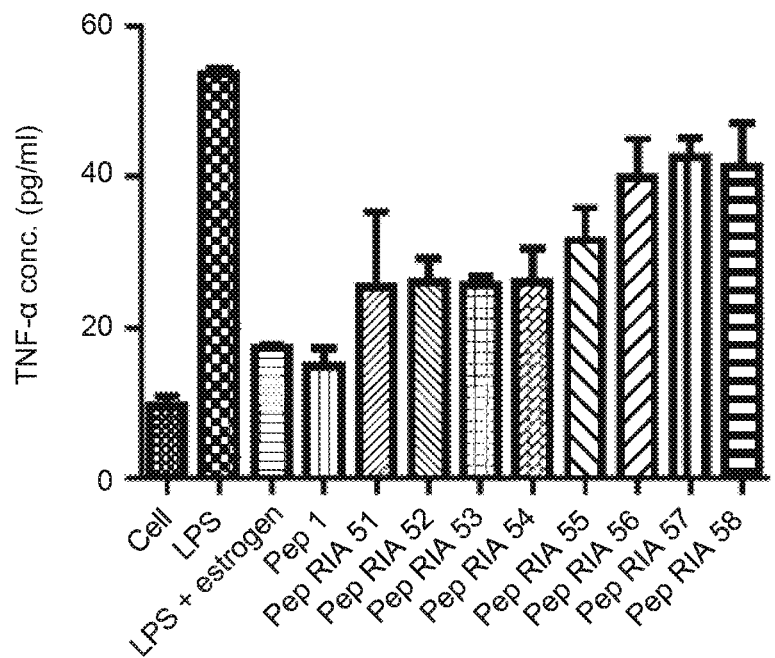
Figure 32:
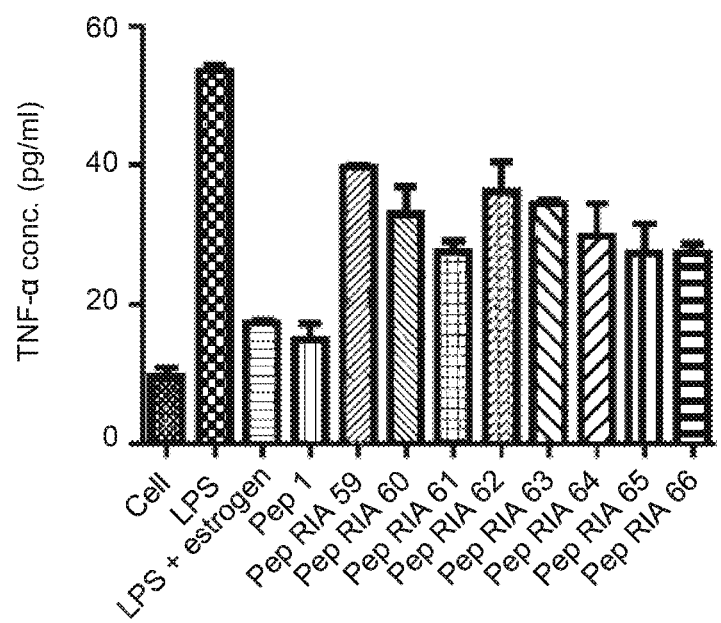
Figure 33:
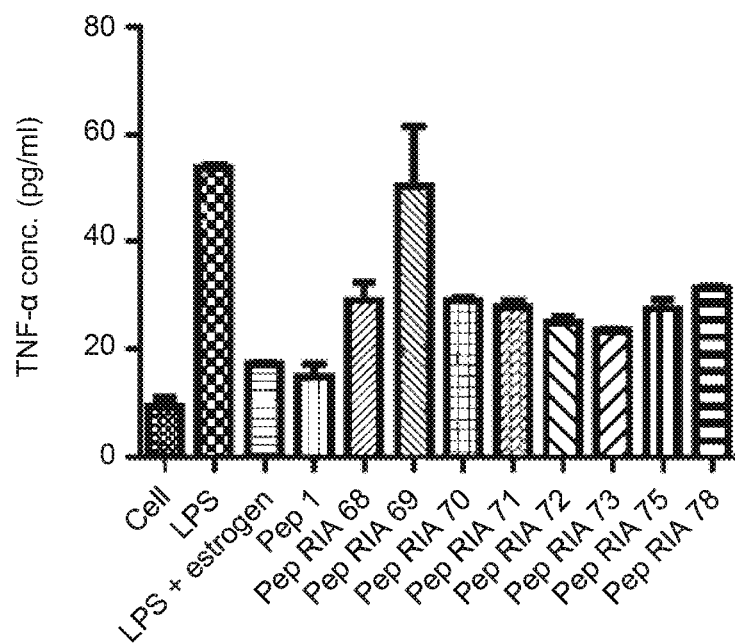
Figure 34:
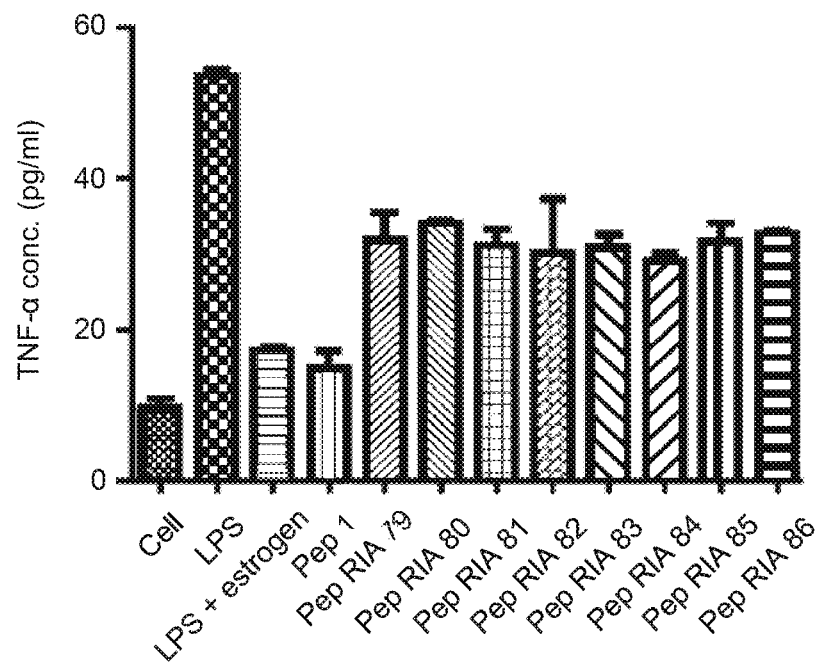
Figure 35:
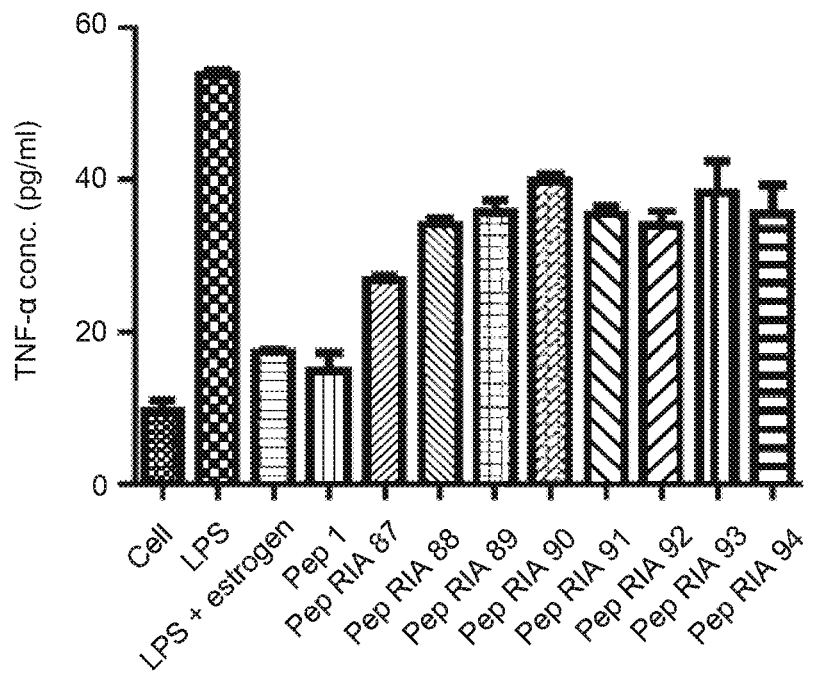
Figure 36:
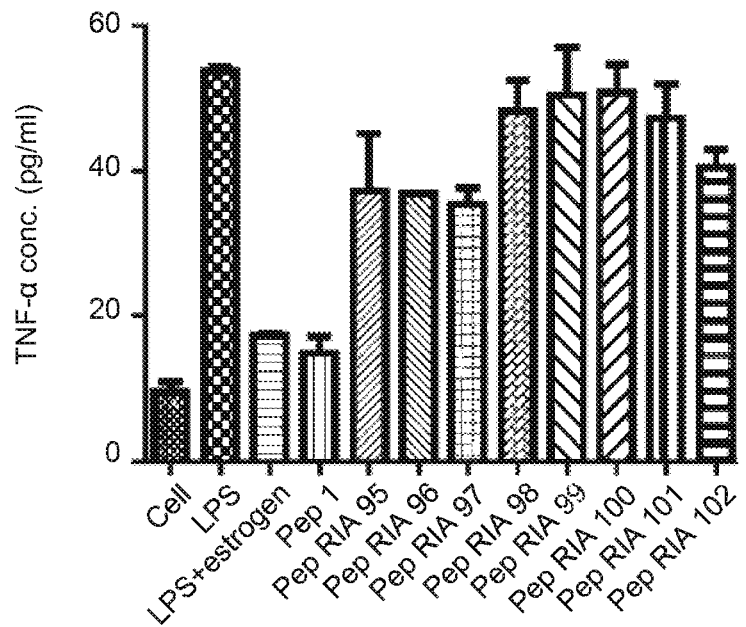
Figure 37:
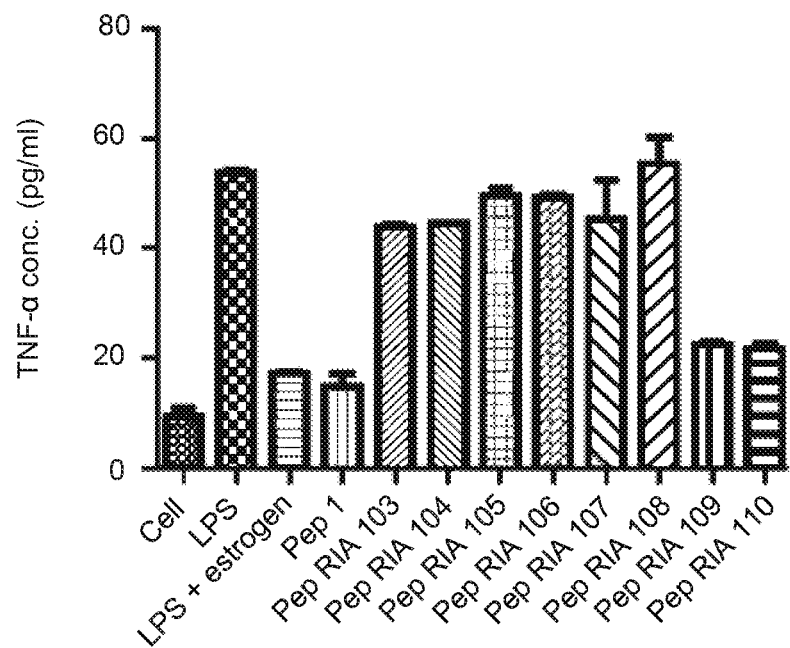
Figure 38:
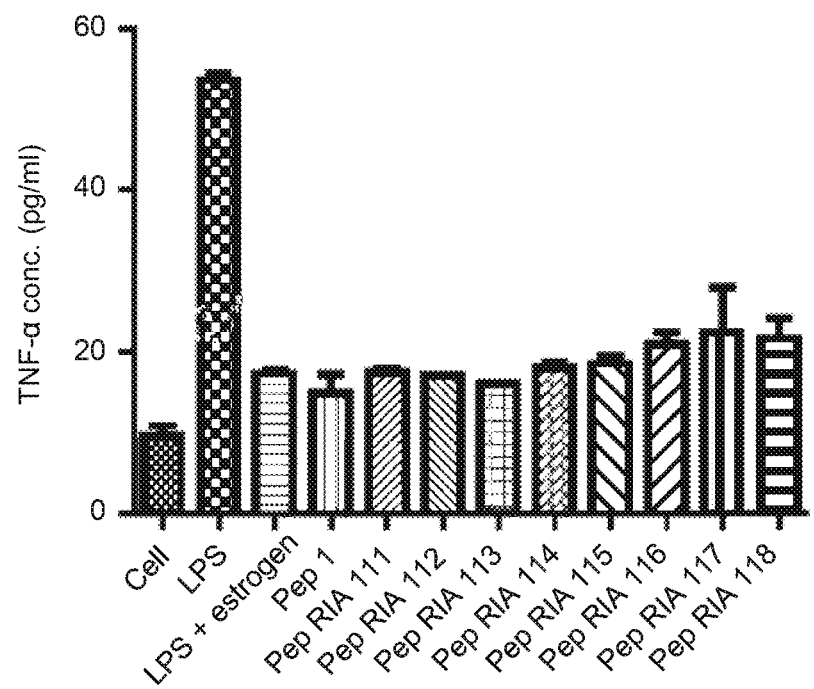
Figure 39:
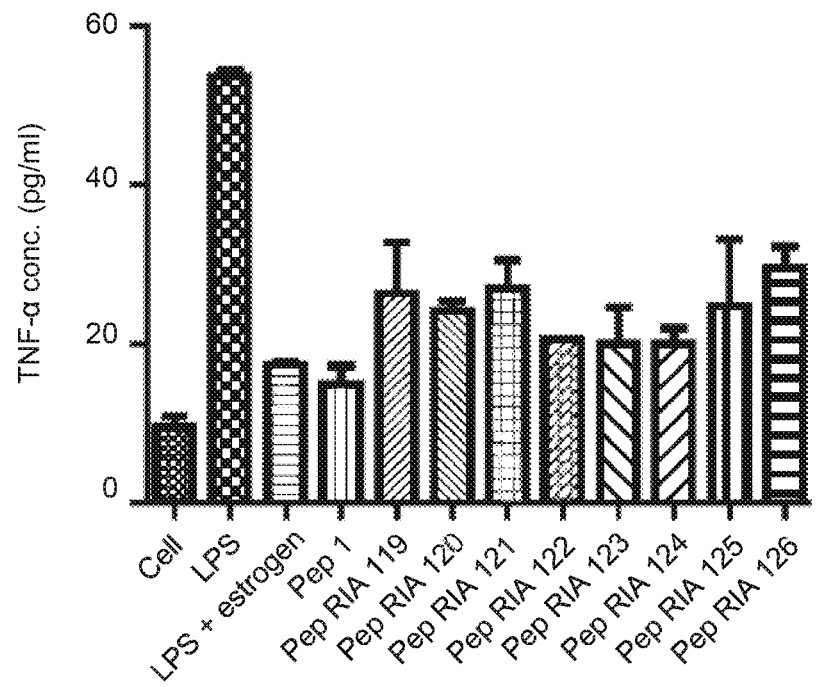
Figure 40:
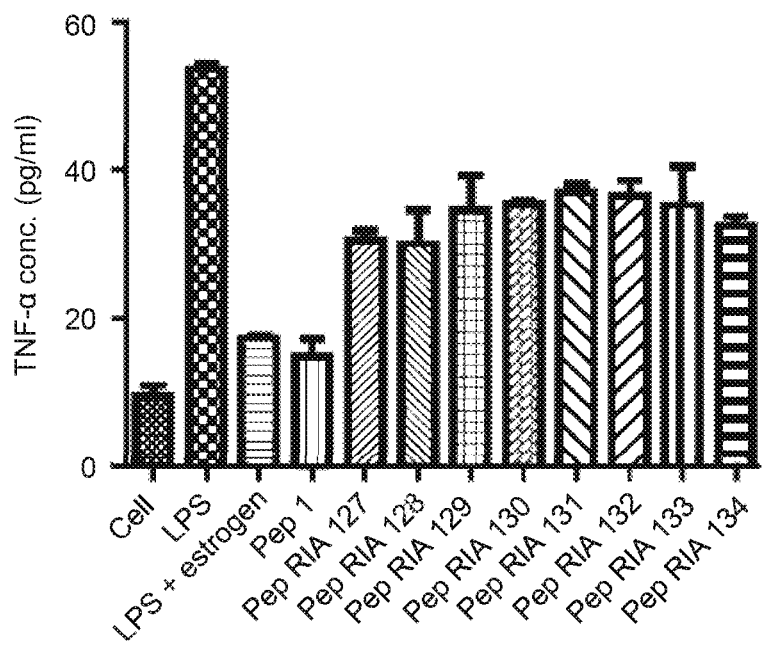
Figure 41:
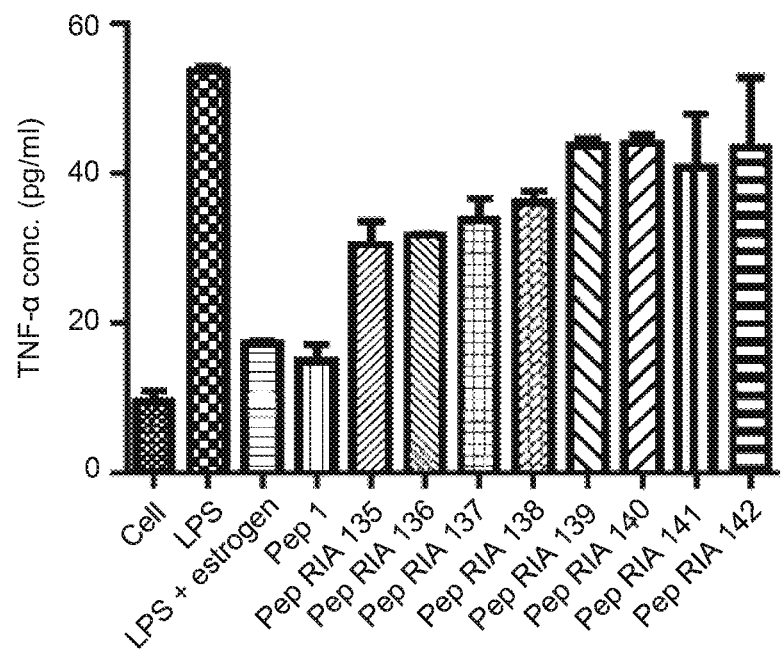
Figure 42:
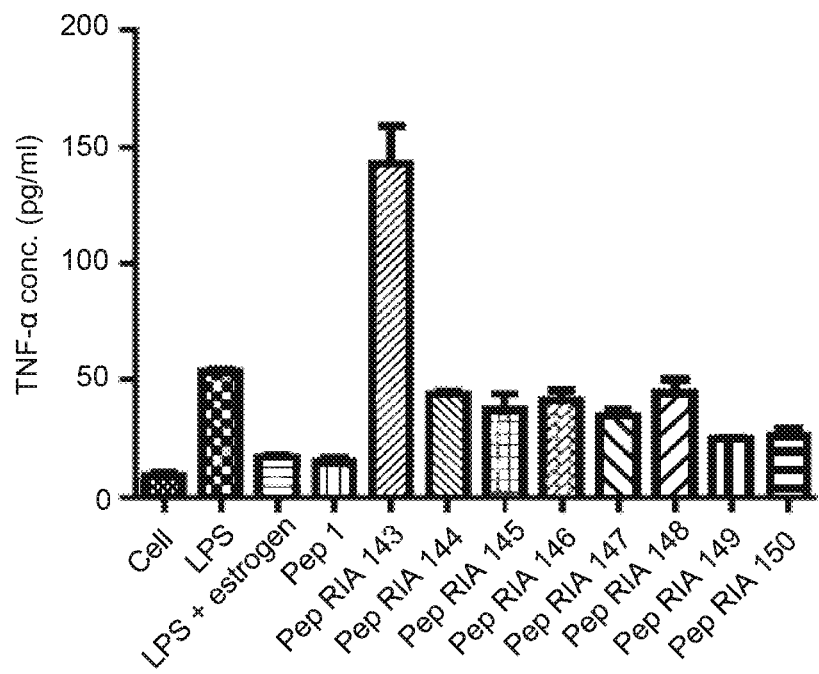
Figure 43:
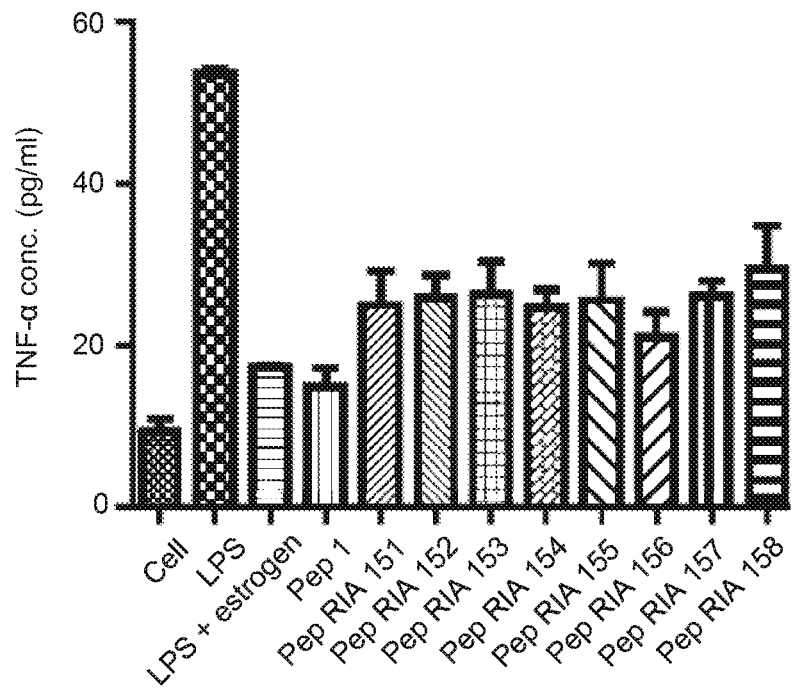
Figure 44:
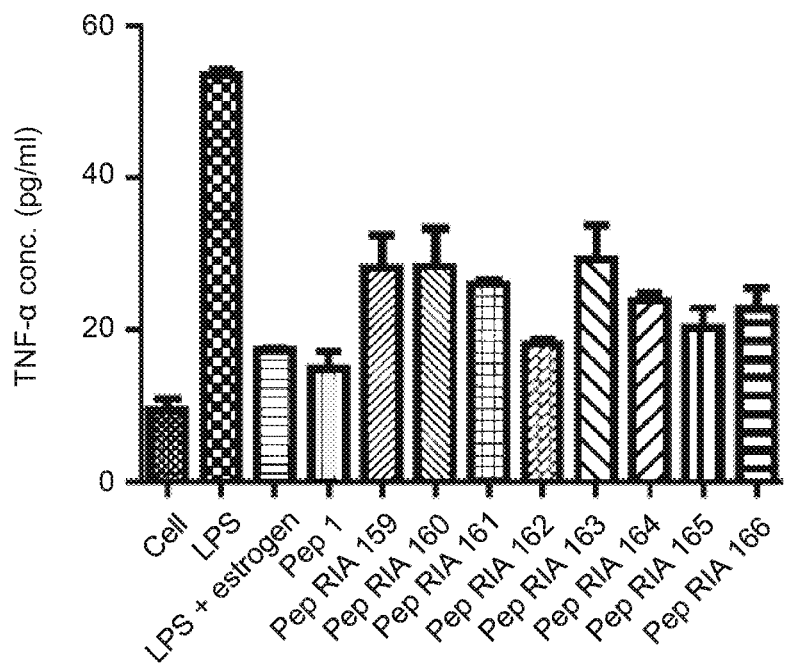
Figure 45:
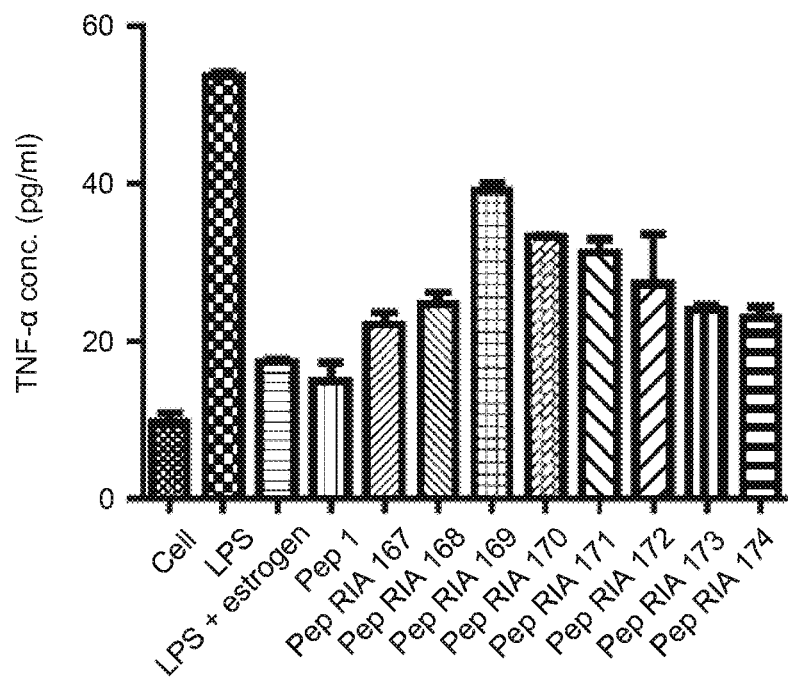
Figure 46:
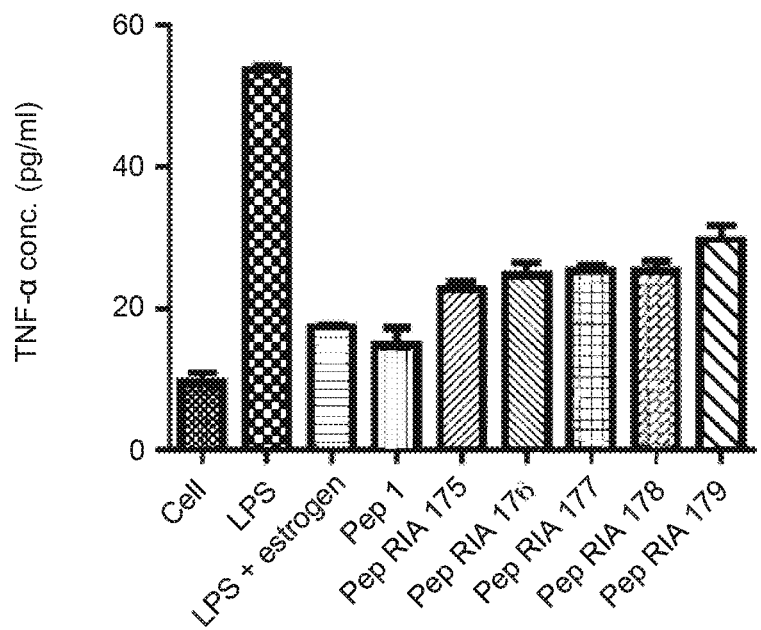

After transfecting NF-kB luciferase to HEK293/null and HEK293/TLR2 cell lines, pam3cys, a synthetic lipoprotein, and FITC (4 µM), a negative control were treated together, and pam3cys with FITC-PEP 1 (4 NM) were again treated together to be cultured for 18 hours. The measurement of NF-kB expression patterns by luciferase strength through lysis of cells with passive lysis buffer—provided by dual-luciferase reporter assay system (Promega)-showed that there was no difference in lipoprotein or FITC-PEP1 treated or non-treated HEK293/null. However, when lipoprotein, an agonist of TLR2, was treated to HEK293/TLR2 cell line, NF-kB expression increased (P<0.01) compared to that in untreated, confirming occurrence of inflammatory responses. Also, NF-kB expression increased when FITC-PEP 1 was treated together compared to that in untreated; and expression decreased compared to the negative control in which lipoprotein and FITC were treated together (P<0.01) (FIG. 2). Ultimately, we were able to confirm that inflammatory response that can be caused by TLR 2 is reduced when PEP 1 is treated together.

Example 2

TNF-α Inhibitory Effect of PEP RIA Series (SEQ ID NO: 2 to 179) Peptides

Based on the results from Example 1 in which the SEQ ID NO: 1 (PEP1) has the TNF-α inhibitory effect, experiment using peptides SEQ ID NO: 2 to 179 were carried out to confirm their TNF-α inhibitory effect. The synthesis of peptides SEQ ID NO: 2 to 179 used the same method mentioned above in Example 1 (method used for synthesis of PEP1), but the amino acids added were different.

Experiment 1: Cell Culture

PBMC (peripheral blood mononuclear cells) layer was separated from blood samples (50 ml) collected in healthy subjects using Biocoll Separating Solution (Biochrom AG, Berlin, Germany). The collected PBMC were enriched in RPMI 1640 medium containing 20% human serum for 30 mins, and then transferred to 100-mm polystyeren cell culture plate coated with human serum for incubation for 2 hrs at 37° C., 5% $CO^2$Incubator. Monocytes were detached from the bottom of the plate using cold PBS, and Incubated to reach the number of $1\times10^1$ cell/well in 96-well plate with RPMI 1640 medium (supplemented with penicillin-streptomycin; 100 mg/ml, human serum; 20%) over night.

Experiment 2: Analysis of TNF-α Inhibitory Effect

ELISA was performed to find out how the peptides of the PEP RIA series influence TNF-α level. PBMC-derived monocytes were incubated to reach the number of $1\times10^5$ cells per well in a 96-well plate and then treated with LPS (lipopolysaccharide; 10 ng/ml, Sigma) for 2 hours. To the monocytes that were washed three times with PBS, OPTI-MEM culture medium was added to induce cell starvation for an hour, 4 µM of the peptide was taken out and incubated for 2 hours. There were three negative control groups. The first group was not treated with anything. The second group that was treated with estrogen (in this experiment, estradiol was used as a kind of estrogen). The third group was treated with LPS (10 ng/ml) or with LPS (10 ng/ml) as well as estrogen (20 nM). PEP1 that was confirmed to have TNF-α inhibiting activity was used as a positive control to measure TNF-α inhibiting activity. After Incubation, TNF-α was measured by following the ELISA kit manual (R&D, Minneapolis, Minn., USA). The details of quantification method can be found in Experiment 2.2 of Example 1.

Using the method stated above, Peptides with TNF-α inhibiting effect were screened. PBMC-derived monocytes were stimulated with LPS (10 ng/ml), which is endotoxin, for 2 hours and were Induced to starve by adding OPTI-MEM for 1 hour. After that, 4 µM of 179 peptides were treated and incubated for 2 hrs. The amount of TNF-α in the cell culture medium was measured using ELISA, and the peptides with TNF-α inhibiting effect were screened by comparing to the negative and positive controls (FIG. 3 to FIG. 23).

The followings are the peptide sequences that showed TNF-α inhibiting effect when compared to the control group that was treated with only LPS: SEQ ID NO: 9, SEQ ID NO:10, SEQ ID NO: 11, SEQ ID NO: 12, SEQ ID NO: 13, SEQ ID NO: 17, SEQ ID NO: 18, SEQ ID NO: 19, SEQ ID NO: 20, SEQ ID NO: 21, SEQ ID NO: 25, SEQ ID NO: 26, SEQ ID NO: 27, SEQ ID NO: 28, SEQ ID NO: 33, SEQ ID NO: 34, SEQ ID NO: 35, SEQ ID NO: 36, SEQ ID NO: 38, SEQ ID NO: 42, SEQ ID NO: 43, SEQ ID NO: 44, SEQ ID NO: 45, SEQ ID NO: 46, SEQ ID NO: 54, SEQ ID NO: 55, SEQ ID NO: 56, SEQ ID NO: 57, SEQ ID NO: 58, SEQ ID NO: 62, SEQ ID NO: 63, SEQ ID NO: 64, SEQ ID NO: 65, SEQ ID NO: 66, SEQ ID NO: 70, SEQ ID NO: 71, SEQ ID NO: 72, SEQ ID NO: 73, SEQ ID NO: 74, SEQ ID NO: 80, SEQ ID NO: 81, SEQ ID NO: 82, SEQ ID NO: 83, SEQ ID NO: 84, SEQ ID NO: 88, SEQ ID NO: 89, SEQ ID NO: 90, SEQ ID NO: 91, SEQ ID NO: 92, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 108, SEQ ID NO: 109, SEQ ID NO: 110, SEQ ID NO: 111, SEQ ID NO: 112, SEQ ID NO: 113, SEQ ID NO: 116, SEQ ID NO: 117, SEQ ID NO: 118, SEQ ID NO: 119, SEQ ID NO: 124, SEQ ID NO: 131, SEQ ID NO: 140, SEQ ID NO: 141, SEQ ID NO: 142, SEQ ID NO: 148, SEQ ID NO: 149, SEQ ID NO: 150, SEQ ID NO: 156, SEQ ID NO: 157, SEQ ID NO: 158, SEQ ID NO: 159, SEQ ID NO: 164, SEQ ID NO: 165, SEQ ID NO: 166, SEQ ID NO: 167, SEQ ID NO: 168, SEQ ID NO: 172, SEQ ID NO: 173, SEQ ID NO: 174, SEQ ID NO: 175, SEQ ID NO: 176, SEQ ID NO: 177, and SEQ ID NO: 178.

Also, the followings are the peptide sequences that showed TNF-α inhibiting effect when compared to the group treated with LIPS and estrogen: SEQ ID NO: 9, SEQ ID NO: 10, SEQ ID NO: 11, SEQ ID NO: 17, SEQ ID NO: 18, SEQ ID NO: 19, SEQ ID NO: 20, SEQ ID NO: 25, SEQ ID NO: 26, SEQ ID NO: 27, SEQ ID NO: 33, SEQ ID NO: 34, SEQ ID NO: 42, SEQ ID NO: 43, SEQ ID NO: 44, SEQ ID NO: 54, SEQ ID NO: 55, SEQ ID NO: 56, SEQ ID NO: 62, SEQ ID NO: 63, SEQ ID NO: 64, SEQ ID NO: 65, SEQ ID NO: 70, SEQ ID NO: 71, SEQ ID NO: 72, SEQ ID NO: 73, SEQ ID NO: 80, SEQ ID NO: 81, SEQ ID NO: 82, SEQ ID NO: 83, SEQ ID NO: 88, SEQ ID NO: 89, SEQ ID NO: 90, SEQ ID NO: 91, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 108, SEQ ID NO: 109, SEQ ID NO: 110, SEQ ID NO: 116, SEQ ID NO: 117, SEQ ID NO: 140, SEQ ID NO: 148, SEQ ID NO: 149, SEQ ID NO: 156, SEQ ID NO: 157, SEQ ID NO: 164, SEQ ID NO: 165, SEQ ID NO: 166, SEQ ID NO: 167, SEQ ID NO: 172, SEQ ID NO: 173, SEQ ID NO: 174.

Experiment 3: Analysis of Peptides Affecting TNF-α Level in THP1 Cell Line

Experiment was carried out using THP-1 cell line (American Type Culture Collection (ATCC), Manassas, Va., USA) which is human acute monocytic leukemia.

THP-1 cells were incubated to reach the number of 1×10$^5$ cells per well in a 96-well plate with RPMI 1640 medium for 24 hrs, followed by addition of 100 μM of PMA (phorbol 12-myristate 13-acetate) for the differentiation Into macrophage. After differentiation of THP-1 Into macrophage by PMA for a day, LPS was treated for 2 hrs and washed off. Starvation for an hour and PEP1 treatment followed.

THP-1 cell differentiated by PMA was treated with LPS (lipopolysaccharide; 10 ng/ml, Sigma) for 2 hours, followed by 2 times washes with PBS. To the cells, OPTI-MEM culture medium was added to induce cell starvation for an hour, and 1 μM of 179 peptides was taken out and Incubated for an hour. After Incubation, TNF-α level was measured by using the ELISA kit and the peptides which reduce the TNF-α level were screened (FIG. 24 to FIG. 46).

As a result, peptide sequence SEQ ID NO: 5, SEQ ID NO: 7, SEQ ID NO: 36, SEQ ID NO: 38, SEQ ID NO: 73, SEQ ID NO: 75, SEQ ID NO: 78, SEQ ID NO: 107, SEQ ID NO: 109 and SEQ ID NO: 179 appeared to reduce the TNF-α level compared to control group treated only with LPS. In addition, SEQ ID NO: 2, SEQ ID NO: 3, SEQ ID NO: 30, SEQ ID NO: 41, SEQ ID NO: 112 and SEQ ID NO: 113 were selected as peptides which reduce the expression level of TNF-α compared to that of group treated with LPS and estrogen.

Example 3

Analysis of Inflammatory Response Induced by Amyloid-β Protein

HMGB1 first undergoes acetylation and translocation to cytoplasm by external stimulation. Then it is secreted out of the cell, therefore serving the role of inflammation-causing cytokine. Because when one has an inflammation due to such activity, HMGB1 protein is secreted from the cell, and patients with inflammatory diseases such as Churg strauss syndrome, rheumatoid arthritis and Sjogren's syndrome will present with elevated serum levels of HMGB1. Hence, if nucleus contains large amount of HMGB1 even when there is a stimulus that causes inflammation, it Is suggestive of the fact that HMGB1 is not being secreted out of the cell, which means inflammation is being suppressed.

Experiment 1: Analysis of Survival and Proliferation of Neural Stem Cells by Anti-Inflammatory Effects of PEP-1

First of all, PEP-1 was prepared according to the manufacturing methods described in Example 1.

Experiment 1-1: Neural Stem Cell Culture and Amyloid-β Toxicity Assessment

Figure 47:
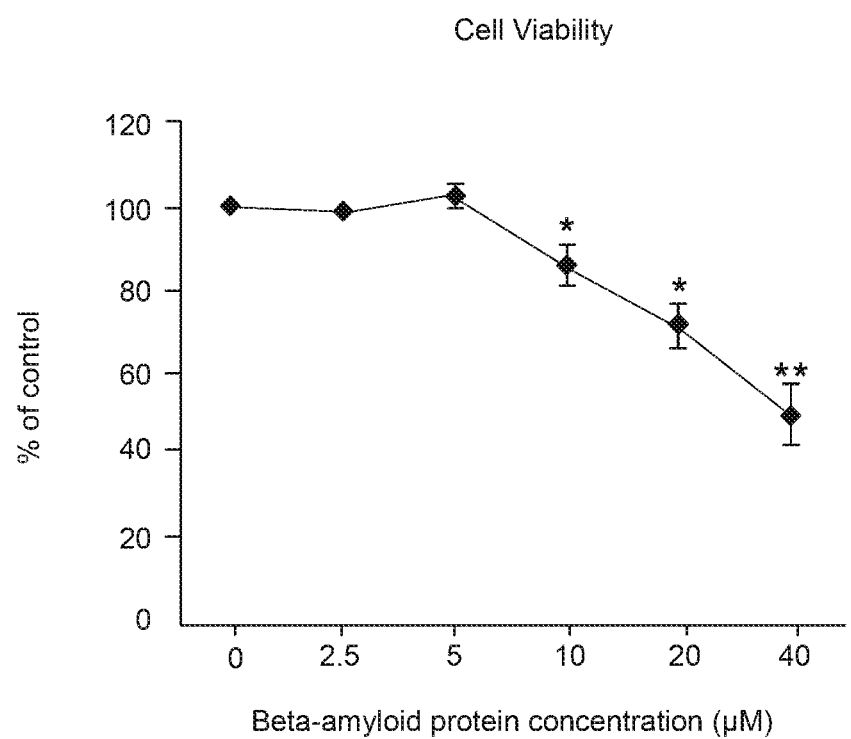
FIG. 47 represents viability of neural stem cell treated with 0, 2.5, 5.0, 10, 20 and 40 μM of amyloid-β protein.
Figure 48:
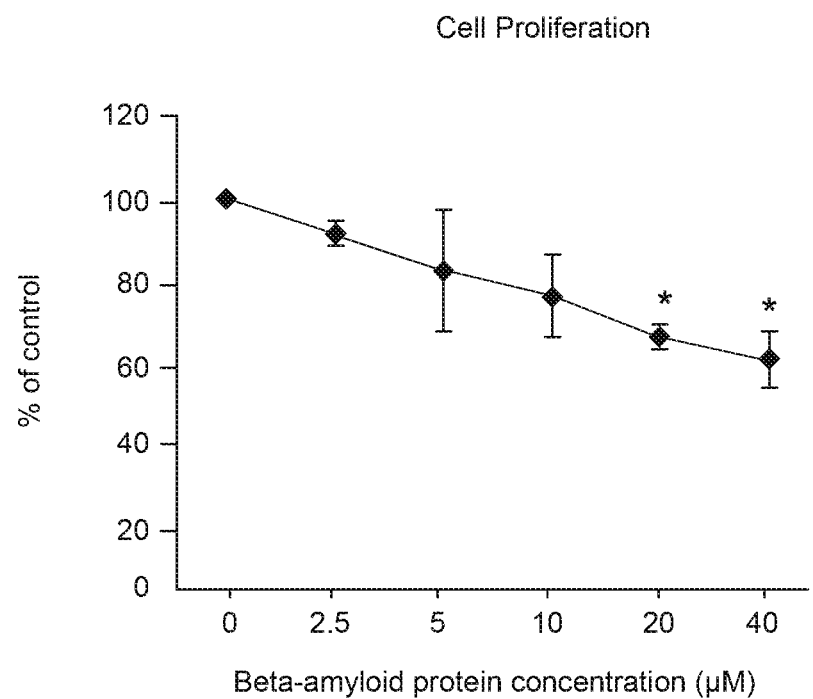
FIG. 48 represents proliferation of neural stem cell treated with 0, 2.5, 5.0, 10, 20 and 40 μM amyloid-β protein.

After removing the cortex from the head of an embryonic rat that had been pregnant for 13 days, it was cultured for a week with Basic Fibroblast Growth Factor (bFGF) to obtain the neural stem cells. To analyze the effects of the amyloid-R protein on the neural stem cells, the pre-oligomerized amyloid-β protein of concentrations 0 to 40 μM was treated on neural stem cells for 48 hours, then CCK-8 assay, BrdU, and TUNEL assay were used for cytotoxicity assessment (refer from B A Yankner et al, 1990 and K N Dahlgren et al, 2002). We used the same concentration of amyloid-1 protein in subsequent experiments after we confirmed that cell survival was reduced to 60% when processed with 20 μM of amyloid-β protein (Refer to FIGS. 47 and 48).

Experiment 1-2: Cell Toxicity Assessment by Treatment with PEP-1

Figure 49:
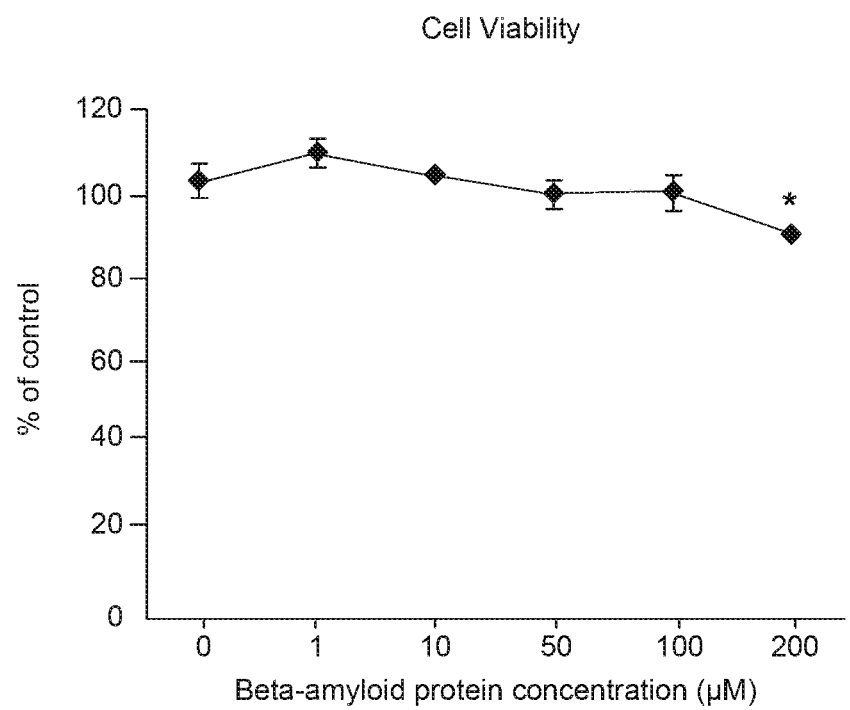
FIG. 49 represents viability of neural stem cell treated with 0, 1, 10, 50, 100 and 200 μM of PEP 1.
Figure 50:
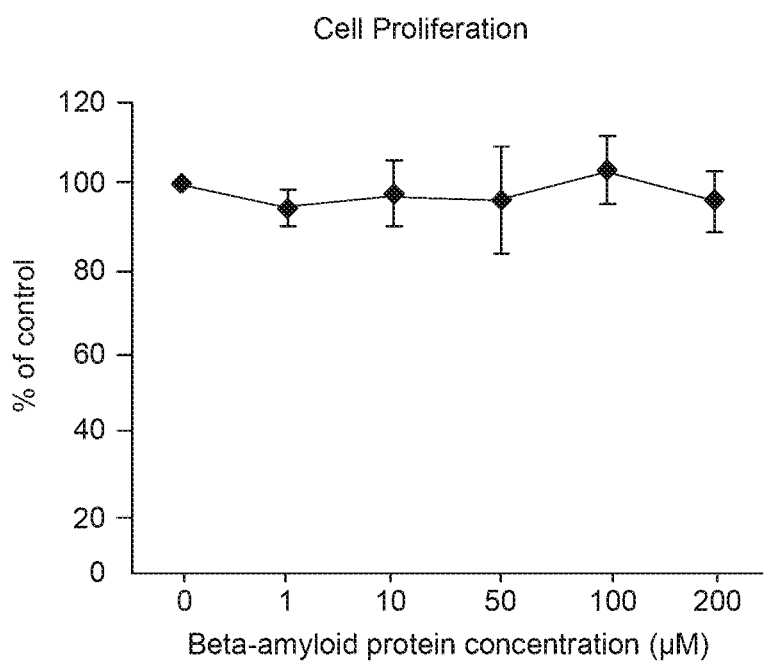
FIG. 50 represents proliferation of neural stem cell treated with 0, 1, 10, 50, 100 and 200 μM of PEP 1.

To evaluate the impact of PEP-1 on the cultured neural stem cells, the neural stem cells were firstly cultured by a well-known method (B A Yankner et, al, 1990 and K N Dahlgren et al, 2002). Then, different concentrations (0, 1, 10, 50, 100, 200 μM) of PEP-1 were treated for 48 hours, followed by cell viability and proliferation assessments using MTT assay, BrdU and TUNEL assay. PEP-1's concentrations from 0 to 200 μM appeared stable in the neuronal system since they did not inhibit both survival and proliferation of neural stem cells (Refer to FIGS. 49 and 50).

Experiment 1-3: Cell Toxicity Assessment by Co-Treatment of Amyloid-β Protein and Telomerase Peptide To determine whether PEP 1 has the effect of suppressing the neurotoxicity caused by amyloid-1 protein, 20 μM amyloid-O protein and various concentrations of PEP-1 were co-treated for 48 hours. The cell viability and apoptosis were measured using MMT assay, CCK-8 assay, LDH assay and TUNEL assay, and neural stem cell proliferation by BrdU assay.

Figure 51:
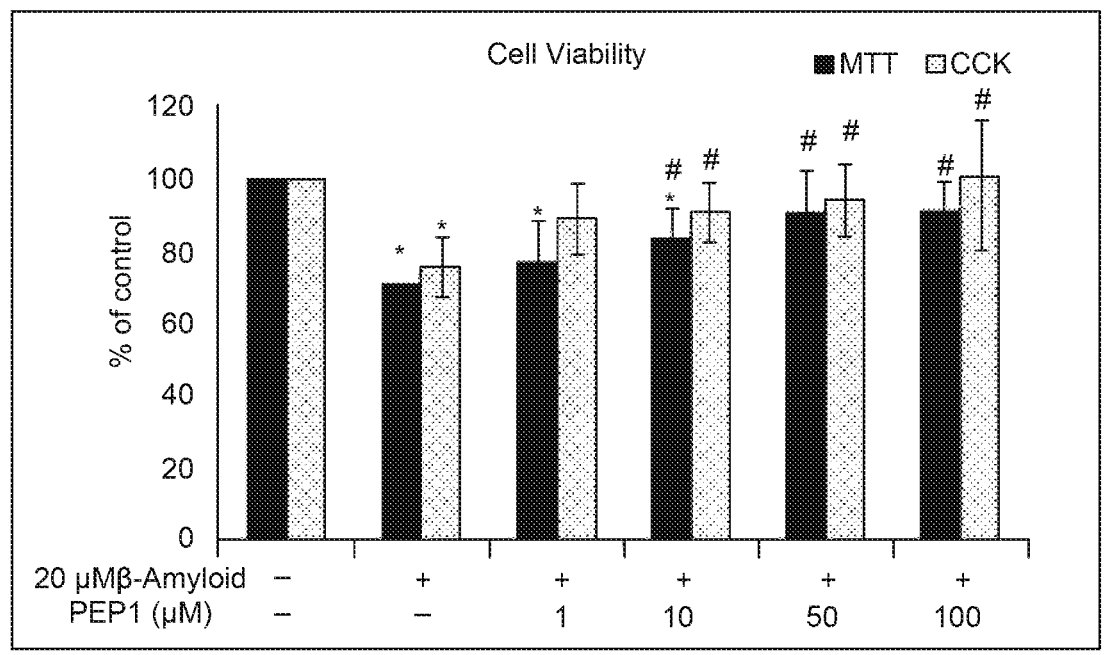
FIG. 51 represents viability of neural stem cell treated with 1, 10, 50 and 100 μM PEP 1; neural stem cells were damaged by 20 μM of amyloid beta protein, and then cell viability was measured after treatment with different concentrations of PEP1. (Control groups were those untreated with amyloid beta protein and telomerase-based peptides).
Figure 52:
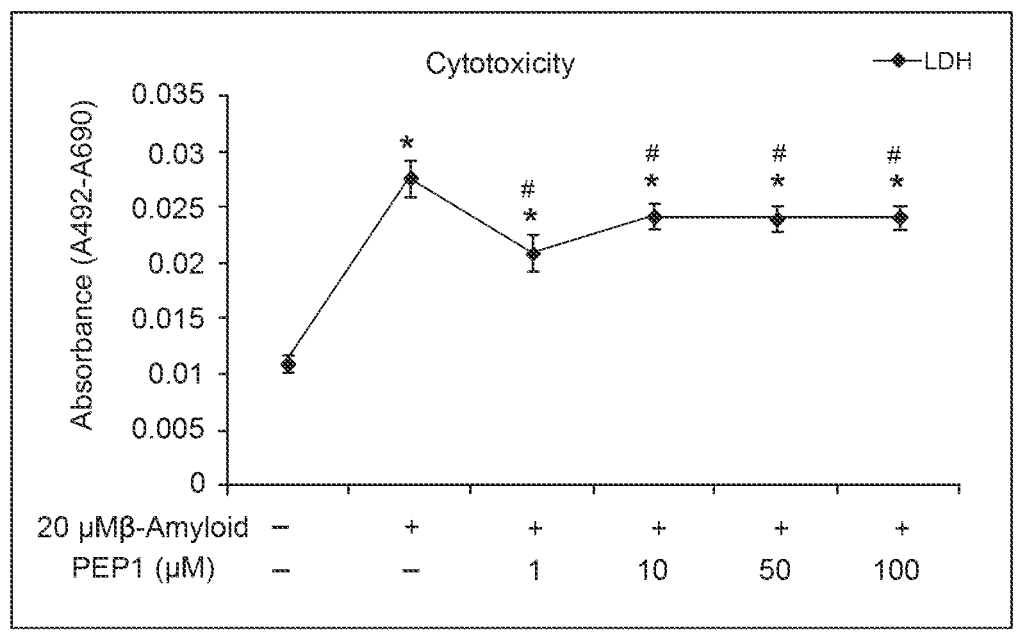
FIG. 52 represents toxicity of neural stem cell treated with 1, 10, 50 and 100 μM PEP 1; neural stem cells were damaged by 20 μM of amyloid beta protein, and then cell toxicity was measured after treatment with different concentrations of PEP1. (Control groups were those untreated with amyloid beta protein and telomerase-based peptides).

The results of MMT assay and CCK-8 assay confirmed that 10 μM of PEP-1 began to protect neural stem cells from neurotoxicity by amyloid-, and the most effective protection was provided in 100 μM. (Refer to FIG. 51). LDH assay was carried out for assessment of the degree of cell death as another method, and we confirmed that the increase in cell death by amyloid-β decreased by PEP-1, and efficacy was seen starting at 1 μM concentration (Refer to FIG. 52).

Figure 53:
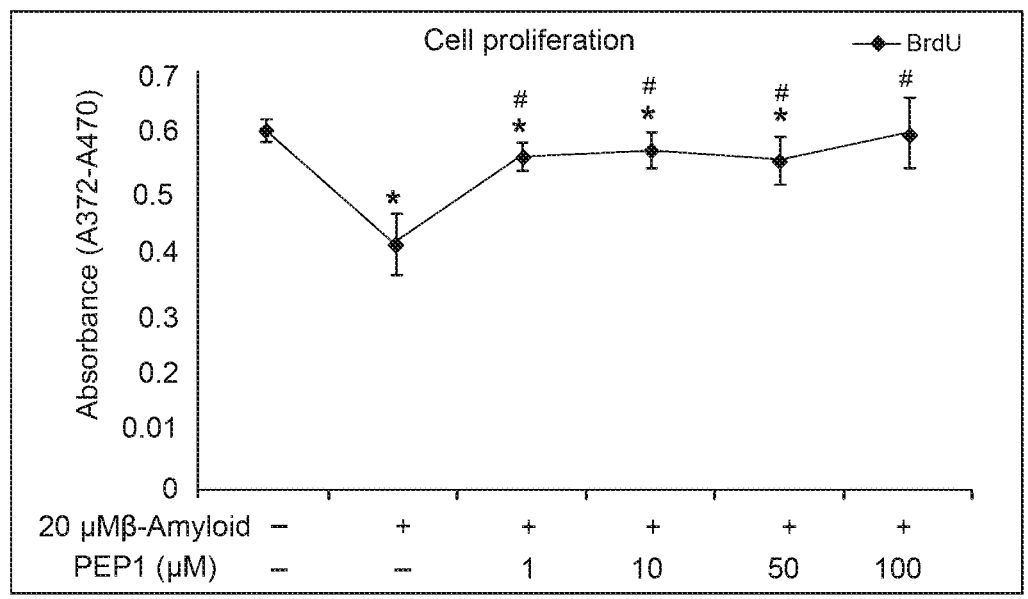
FIG. 53 represents proliferation of neural stem cells treated with 1, 10, 50 and 100 µM PEP 1; neural stem cells were damaged by 20 µM of amyloid beta protein, and then cell proliferation was measured after treatment with different concentrations of PEP1. (Control groups were those untreated with amyloid beta protein and telomerase-based peptides).

We also confirmed with BrdU assay that the decreased cell proliferation due to amyloid-O protein was restored when processed with PEP-1 (Refer to FIG. 53).

Figure 54:
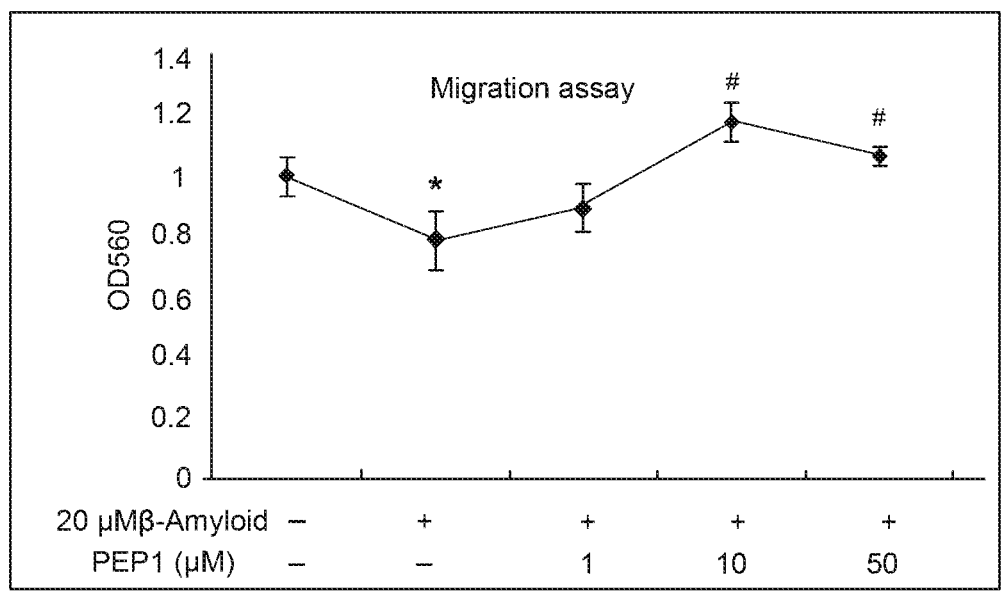
FIG. 54 represents migration of neural stem cells treated with 1, 10, 50 and 100 µM PEP 1; neural stem cells were damaged by 20 µM of amyloid beta protein, and then cell migration was measured after treatment with different concentrations of PEP1. (Control groups were those untreated with amyloid beta protein and PEP1).

Cell mobility is a vital matter due to the nature of neural stem cell. According to the experimental results of cell mobility, we confirmed that the decreased cell proliferation due to amyloid-β protein was restored when processed with PEP-1, and that it Increased even more when in 10 μM concentration, compared to control. This suggests that in the future clinical trials, processing prior to stem cell transplantation may draw more effective results. (Refer to FIG. 54).

Figure 55:
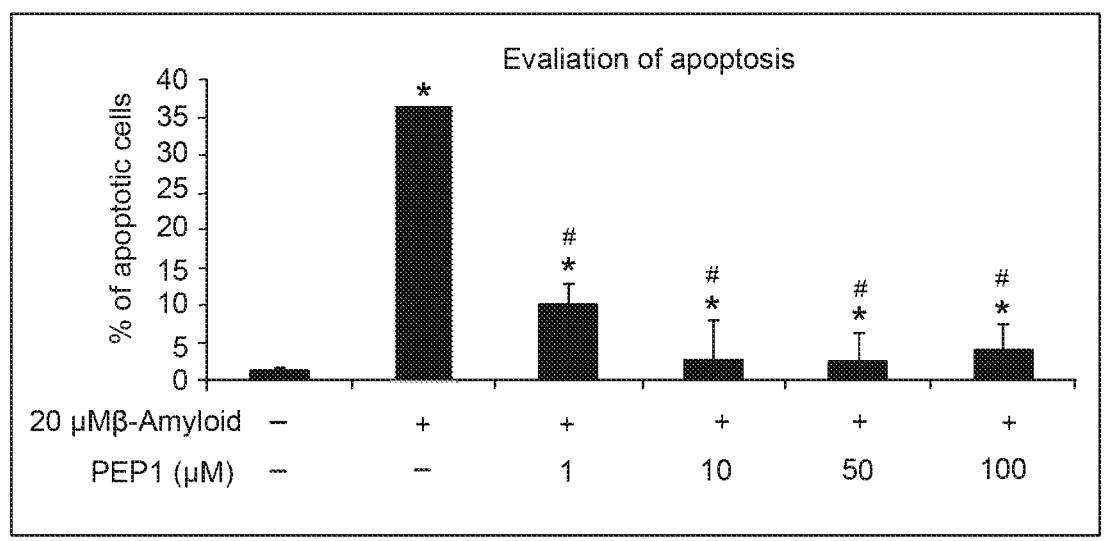
FIG. 55 represents apoptosis of neural stem cells treated with 1, 10, 50 and 100 µM PEP 1; neural stem cells were damaged by 20 µM of amyloid beta protein, and then cell apoptosis was measured after treatment with different concentrations of PEP1. (Control groups were those untreated with amyloid beta protein and telomerase-based peptides).

To confirm the degree of neuronal stem cells damage, TUNEL assay was performed. Neuronal stem cell death was observed to be significantly increased in 20 μM amyloid-β protein treatment group, and neuronal stem cell death decreased when treated with 1 to 100 μM of PEP 1. (Refer to FIG. 55)

Figure 56:
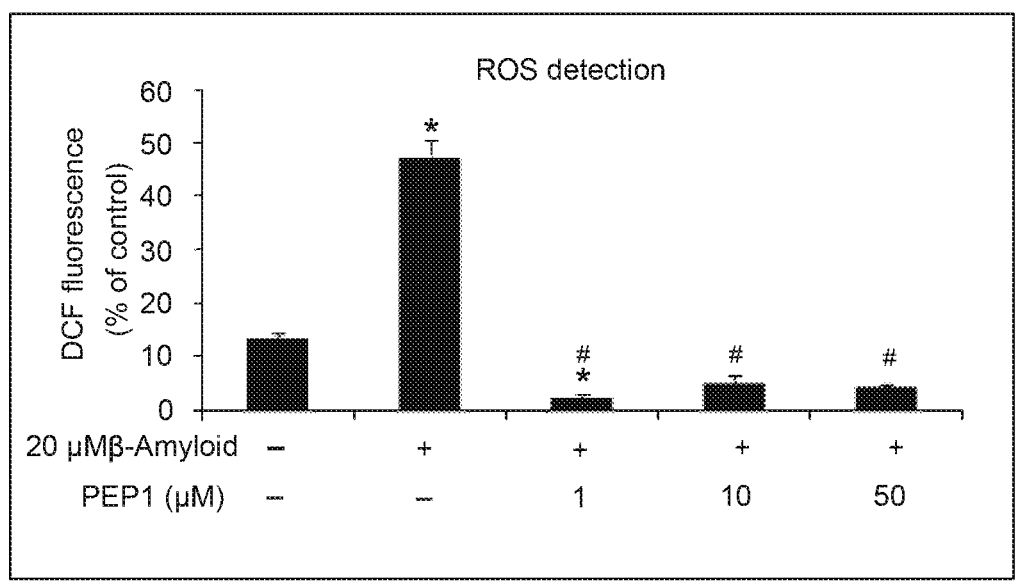
FIG. 56 represents ROS (Reactive Oxygen Species) inhibitory effect of PEP1 in neural stem cells damaged by amyloid beta peptide; neural stem cells were damaged by 20 µM of amyloid beta protein, and then inhibition of ROS was measured after treatment with different concentrations of PEP1 (1, 10, 50 and 100 µM). (Control groups were those untreated with amyloid beta protein and PEP1).

The mechanism of action of PEP-1's protective effect on apoptosis by amyloid-β protein was Investigated. First, it was investigated whether PEP-1 is capable of minimizing the oxidative damage caused by amyloid-β protein. Change in generation of reactive oxygen species after treatment with amyloid-β protein and PEP-1 was observed by using DCF-DA staining (Molecular Probes, Eugene, Oreg.). In the group in which reactive oxygen species increased due to 20 μM of amyloid-1 protein, the increased reactive oxygen species decreased by PEP-1 treatment (1 μM, 10 μM, 50 μM) (Refer to FIG. 56).

Experiment 1-4: Comparative Analysis of Protein Expression Levels Between the Groups Treated with and without PEP-1

Protein expression level of PEP-1 treated group and untreated group was analyzed by 2D-electrophoresis technique and antibody microarray technique. Prepared 200 μg by extracting proteome from the neural stem cells cultured in Experiment 1-1 of example 3. In addition, the group in which PEP-1 was not treated was used as the comparison group in the same condition.

2D-electrophoresis was performed using 12% acrylamide gels. First gel electrophoresis was performed at PI 4~10N, using a gel size of 8.5×7 cm. After electrophoresis, it was dyed with Colloidal Coomassie Blue, and then compared expression by using PDQuest software to analyze each spot.

Figure 57:
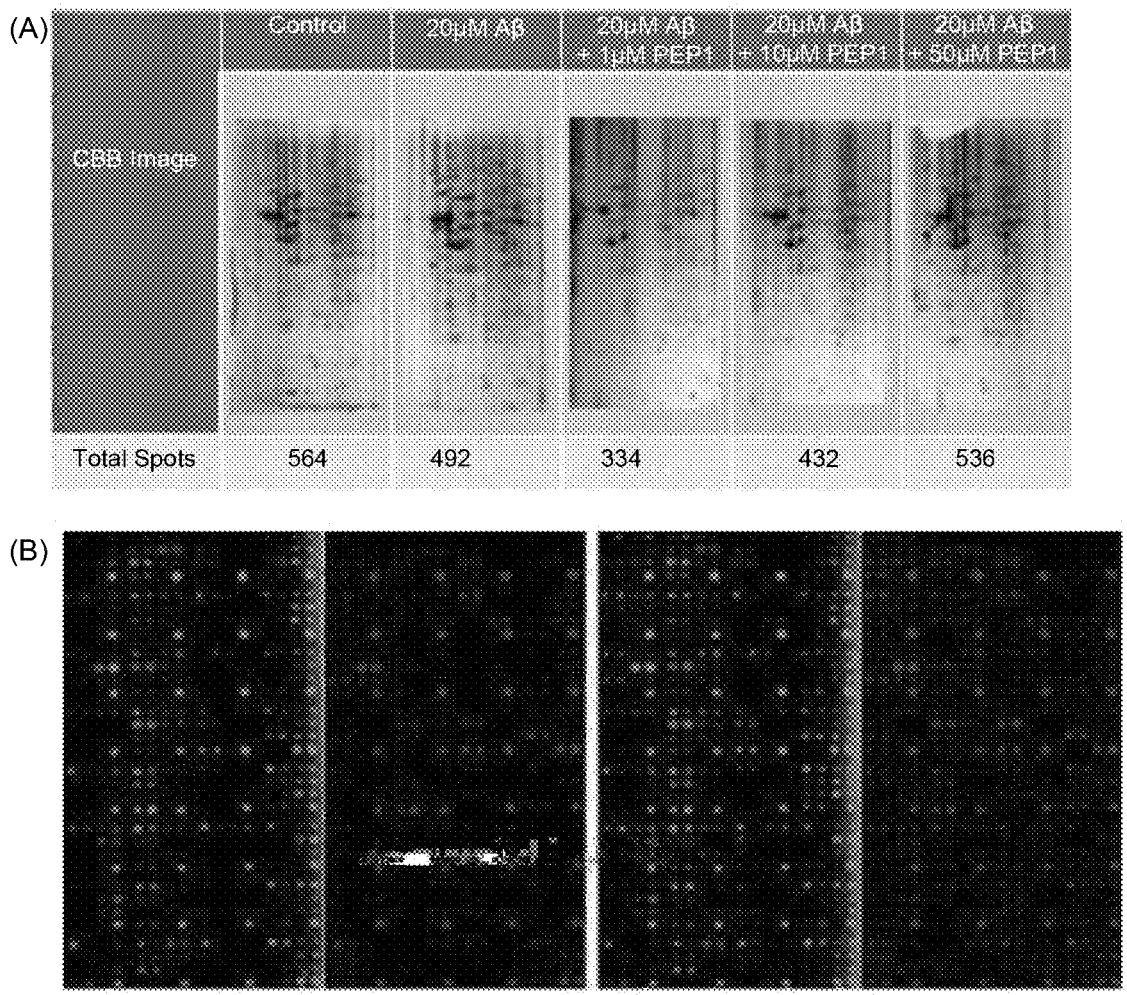
FIG. 57 represents the results of protein expression levels analyzed by (A) 2D-electrophoresis and (B) Antibody Array; neural stem cells were damaged by 20 µM of amyloid beta protein, and then protein expression level was measured after treatment with different concentrations of PEP1 (1, 10 and 50 µM). (Control groups were those untreated with amyloid beta protein and PEP1).

Difference in the expression levels of more than 1.5 times was Identified using MALDI-TOF MS (Matrix Desorption/Ionization Time of Flight Mass Spectrometry). Among these, proteins correlated with inflammation-related signaling, such as i-NOS and HMGB-1 were identified (Refer to Table 6). The changes in protein expression levels either increased or decreased by 1.5 times by amyloid-β protein, but it was confirmed that expression level was regulated close to that of negative control when PEP-1 was added (Refer to FIG. 57).

Antibody microarray was carried out by using cell signaling kit (CSAA1, Panorama™ Ab Microarray Cell Signaling kit), array slides were scanned by GenePix Personal 4100A scanner (Molecular Devices) and the data were analyzed by GenePix Pro 5.0 (Molecular Devices).

The Table 6 below is an analysis of expression levels of proteins associated with inflammation by 2D electrophoresis technique. The control group represents protein expression level of cells that were not treated with neither amyloid-β protein nor PEP-1. It shows increased or decreased multiple of protein expression based on the control group's expression level.

We confirmed with the results of analysis that like the suggested in Table 6 below, Inflammation related protein over-expression or under-expression was controlled by PEP-1; the protein expression level was close to that of negative control group.

TABLE 6

| Protein | Negative Control | 20 ug β-amyloid treated group (fold) | 20 ug β-amyloid + PEP 1 treated group (fold) |
|---|---|---|---|
| HSP 70 | 1.0 | −2.3 | 1.2 |
| HSP 90 | 1.0 | −1.8 | 1.0 |
| HMGB1 | 1.0 | −1.5 | 2.8 |
| GADD 153 | 1.0 | 1.6 | 1.2 |
| i-NOS | 1.0 | 1.9 | −1.1 |
| e-NOS | 1.0 | 1.9 | −1.1 |
| Pyk2 | 1.0 | 2.0 | 1.2 |
| MAP Kinase | 1.0 | 2.2 | 1.0 |

Phosphatidylinositol 3-kinase (PI3K)/AKT signaling pathway serves a crucial role in the growth and survival of neuronal stem cells. PI3K pathway is activated by growth factors and regulatory factors, and is involved in the normal regulation of neuronal stem cell growth and survival. AKT signaling pathways disable several pro-apoptotic factors, including a well-known apoptotic signaling molecule, GSK33.

Figure 58:
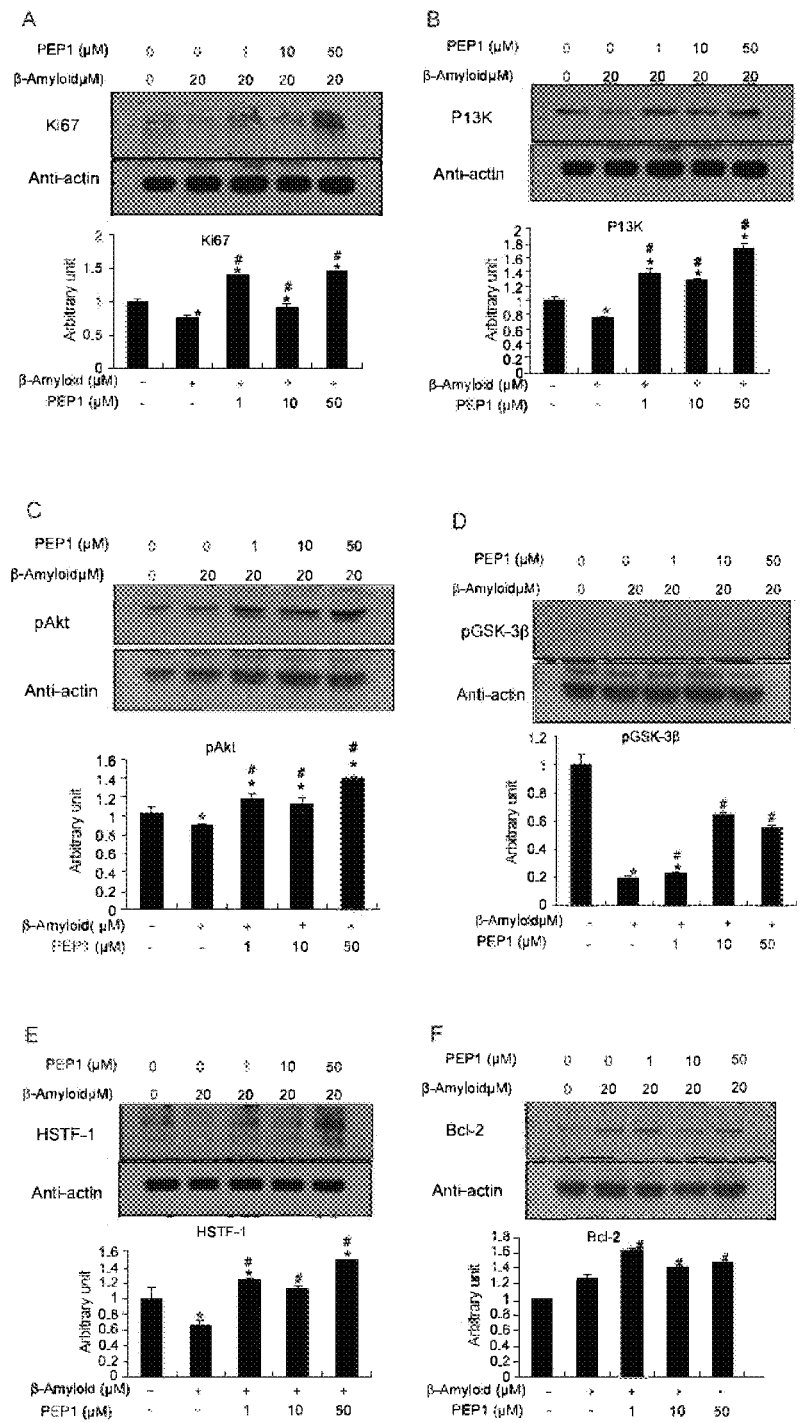
FIG. 58 represents the results of western blot showing the expression level of inflammation-related proteins: neural stem cells were damaged by 20 µM of amyloid beta protein, and then cells were treated with different concentrations of PEP1 (1, 10 and 50 µM).
Figure 58:
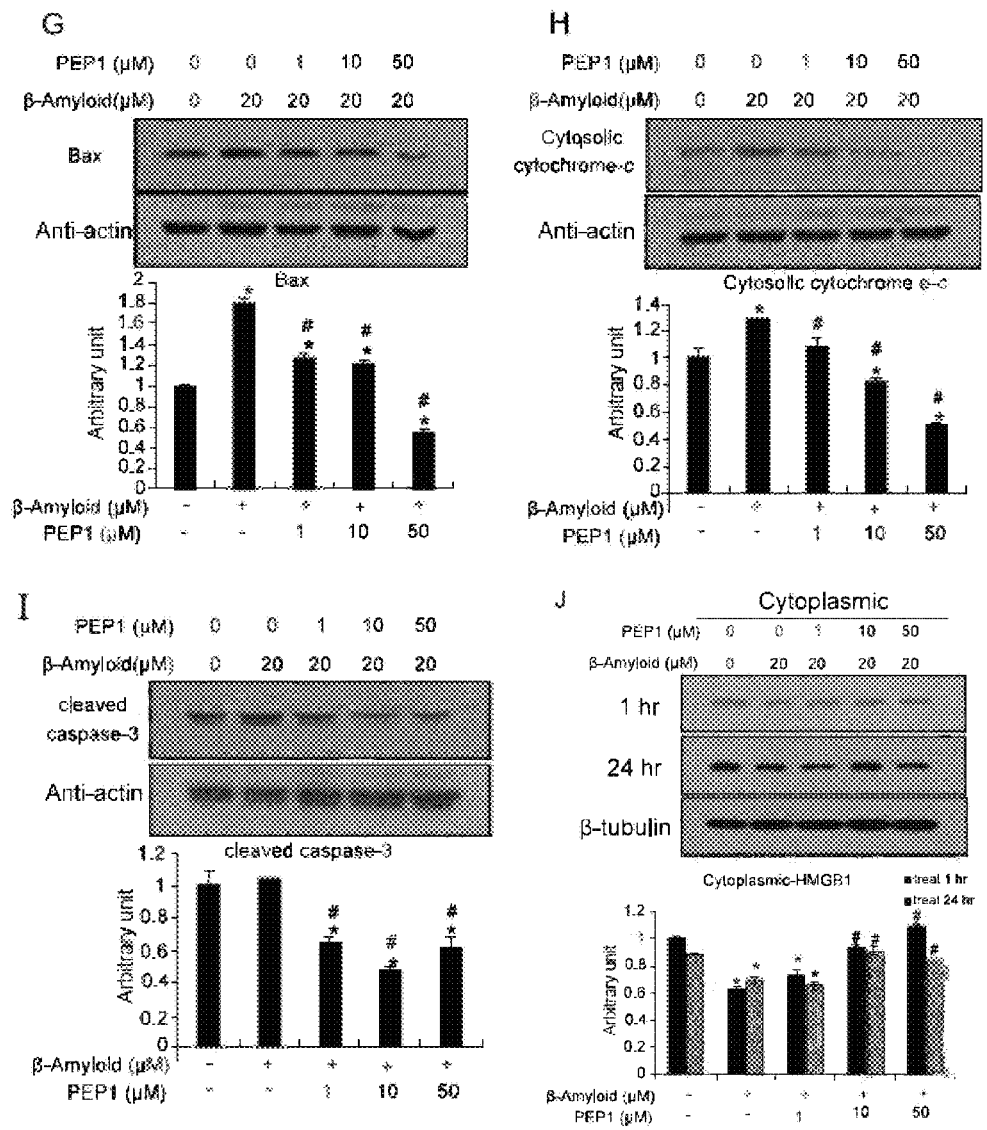

To further investigate the anti-inflammatory effects of PEP-1, we performed Western blot on HMGB1, since it showed a major change in protein analysis. As a result, the processing of the PEP-1 increased the protein expression levels in anti-apoptotic proteins such as K167, pAKT, PI3K, HSTF-1 and Bcl-2, and decreased the protein expression levels of apoptotic signals such as Bax, GSK3β, Cytochrom-c, caspase-3 (Refer to FIG. 58).

HMGB1, a non-histone structure protein that binds to DNA, serves diverse roles within a cell; such as stabilizing nucleosome structure and regulating gene expression. As one of the inflammation-causing substance that Is excreted in the late phase of inflammatory response, it is excreted by macrophages and monocytes when inflammation is stimulated, but when neuron is significantly damaged and leads to cell necrosis, it will be excreted out of the cell, causing an intense inflammatory response. The increase of HMGB1 by PEP-1 treatment after the decrease by amyloid-β treatment in the cytoplasm of the nerve cells reflects the fact that PEP-1 inhibits secretion of HMGB1 out of the cell caused by neuron cell death; therefore suggesting that PEP-1 has powerful anti-inflammatory effects (Refer to FIG. 58).

Figure 59:
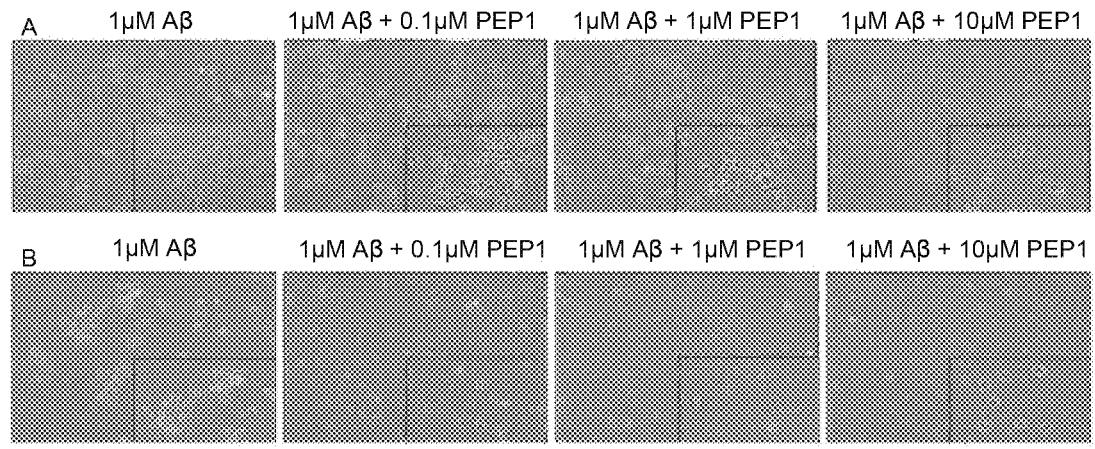
FIG. 59 represents the inhibitory effect of PEP 1 on amyloid beta protein aggregation; (A) shows the reduced oligomerization of amyloid beta proteins when co-treated with 1 µM amyloid beta protein and PEP 1 (0.1, 1 and 10 µM). (B) shows the case when PEP-1 was treated on the amyloid-β protein that was already induced for aggregation.

In addition, we Investigated the response of PEP-1 to the amyloid-β aggregation. Aggregation of protein was inhibited when treated with PEP-1 (Refer to FIG. 59 (A)) in induction of aggregation of amyloid-β, and protein underwent degradation when PEP-1 was treated on the amyloid-β protein that was already induced for aggregation (Refer to FIG. 59(B)).

In the mechanism of action of PEP-1, we have previously confirmed the increase in cell survival signaling and decrease in apoptosis signaling of PI3K. To investigate whether these effects are direct or indirect, we treated PI3K-inhibitor, LY294002 (Promega). As a result, the increased cell viability after treating with PEP 1 decreased when treated with LY294002. Thus, we can conclude that PI3K is directly associated with PEP 1's neuroprotective effect (Refer to FIG. 60).

PEP-1 inhibits apoptosis of neural stem cells by amyloid-O protein. Also, the improvement of cell mobility of neural stem cells was confirmed, therefore suggesting a variety of possibilities in clinical application. The inhibition effects from neurotoxicity caused by beta-amyloid protein was verified by the anti-inflammatory effect of the mechanism of action of PEP 1, increased survival factors of neuro stem cells and decreased apoptotic factors, especially activation of PI3K signaling pathway and antioxidant effects.

Example 4

Effects of PEP RIA Series' Peptides (Sequence No. 2 to 179) on Inflammation by Amyloid-β Protein

Experiment 1. Cell Culture

Undifferentiated PC12 cells (ATCC, Rockville, Md., USA) were maintained in logarithmic-phase growth on poly-1-lysine (Sigma, Saint Louis, Mo., USA)—precoated 100 mm dishes (Corning, Pa., USA) In RPMI 1640 medium (GIBCO, Grand Island, N.Y., USA) containing 10% heat-Inactivated horse serum, 5% heat-Inactivated fetal bovine serum, 100 units/ml penicillin, and 100 g/ml streptomycin. Cultures were incubated at 37° C. in a humidified atmosphere with 5% $CO^2$. The cultures were grown to 50% confluence and were harvested in $Ca^2/Mg^2$—free Hank's balanced salt solution containing 1 mM EDTA. Cells were plated at a density of 1×10 cells/100 mm dish and Incubated for 24 hrs. For neuronal differentiation, PC12 cells were serum-starved for 12 hrs (RPMI1640 medium containing 100 units/ml penicillin and 100 g/ml streptomycin without horse serum or fetal bovine serum); thereafter, the cells were maintained in serum-free medium. After two days the medium was replaced with fresh serum-free medium. On day three, NGF (50 ng/ml, Sigma, Saint Louis, Mo., USA) was added to the medium, and the cultures were maintained for an additional three days. After differentiation, nPC12 cells were incubated with 20 μM amyloid-1 with several concentrations of peptides [0 (control), 1, 10, and 50 μM] for 48 hrs.

Experiment 2. Western Blot Analysis

Levels of HMGB1 were analyzed by western blotting. Briefly, 5×10⁶ cells were washed twice in cold PBS, Incubated for 10 min on ice in lysis buffer [50 mM Tris (pH 8.0), 150 mM NaCl, 0.02% sodium azide, 0.2% SDS, 100 μg/mi phenyl methyl sulfonyl fluoride (PMSF), 50 μl/ml aprotinin, 1% Igepal 630, 100 mM NaF, 0.5% sodium deoxy choate, 0.5 mM EDTA, 0.1 mM EGTA]; unbroken cells and nuclei were pelleted by centrifugation for 10 min at 2000×g and the lysates were cleared by centrifugation at 10,000×g. The antibodies used were: anti-HMGB1 (1:1000, Cell Signaling, Beverly, Mass., USA) and anti-β-tubulin (1:1000, Cell Signaling, Beverly, Mass., USA). The membranes were washed with Tris-buffered saline containing 0.05% Tween-20 (TBST), and then processed using HRP-conjugated anti-rabbit antibody (Amersham Pharmacia Biotech, Piscataway, N.J., USA) followed by ECL detection (Amersham Pharmacia Biotech,). The blots were quantified with an image analyzer (GE Healthcare, ImageQuant LAS 4000).

Figure 60:
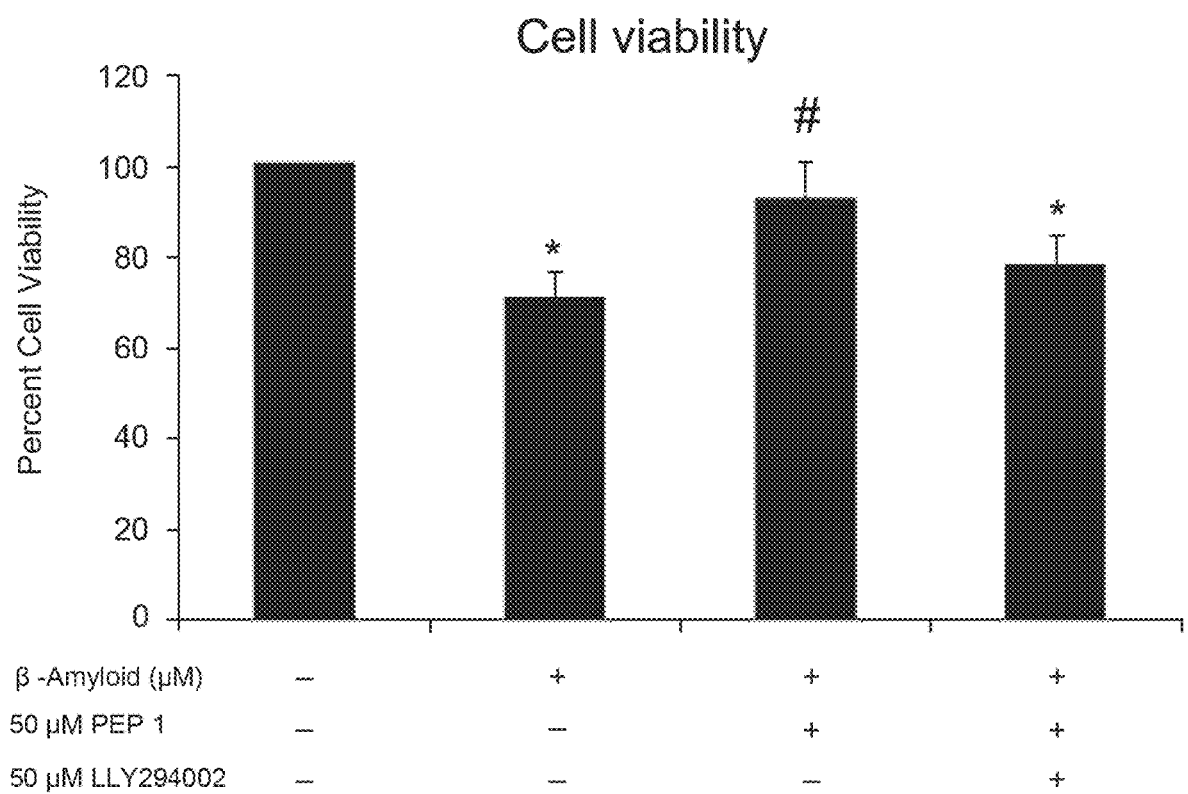
FIG. 60 represents the effect of PI3K-inhibitor, LY294002 on the cell viability treated with PEP 1. The increased cell viability after treating with PEP 1 decreased when treated with LY294002.
Figure 61:
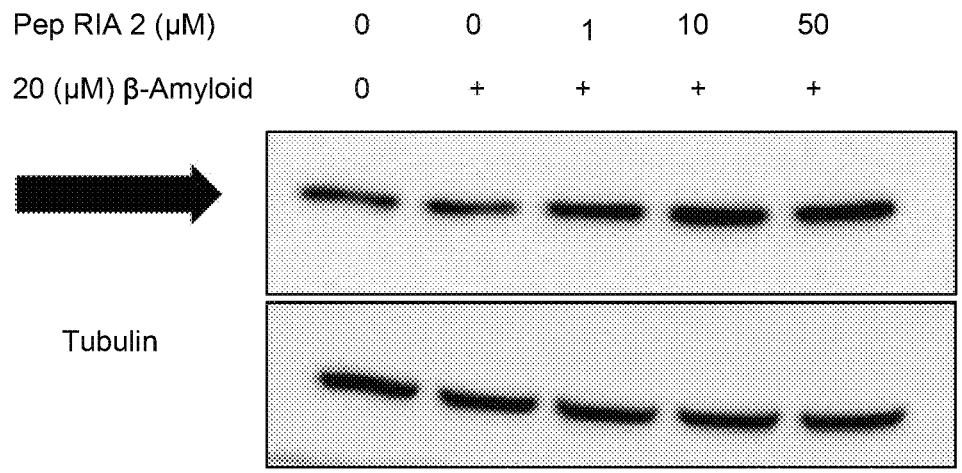
FIG. 61 to FIG. 159 are the results from the western blot analysis of selected peptides showing accumulation of HMGB1 in the cell.
Figure 62:
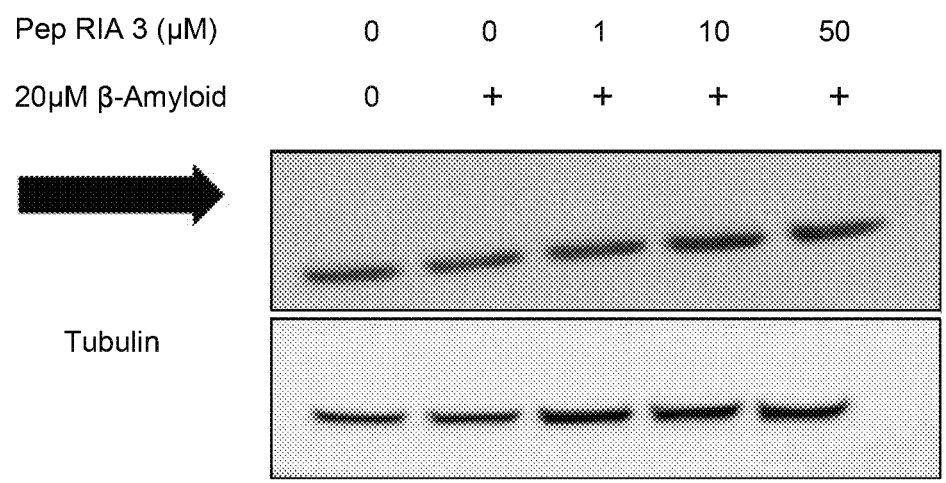
Figure 63:
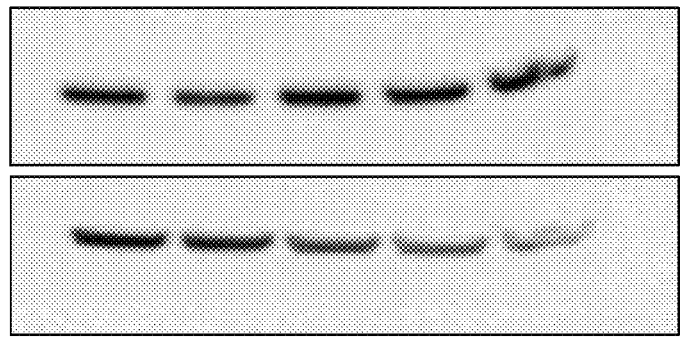
Figure 64:
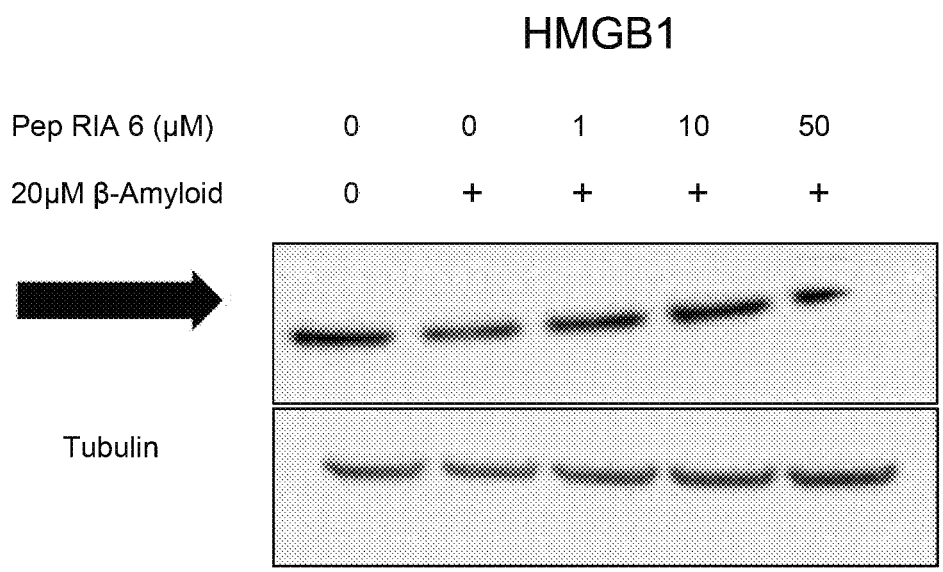
Figure 65:
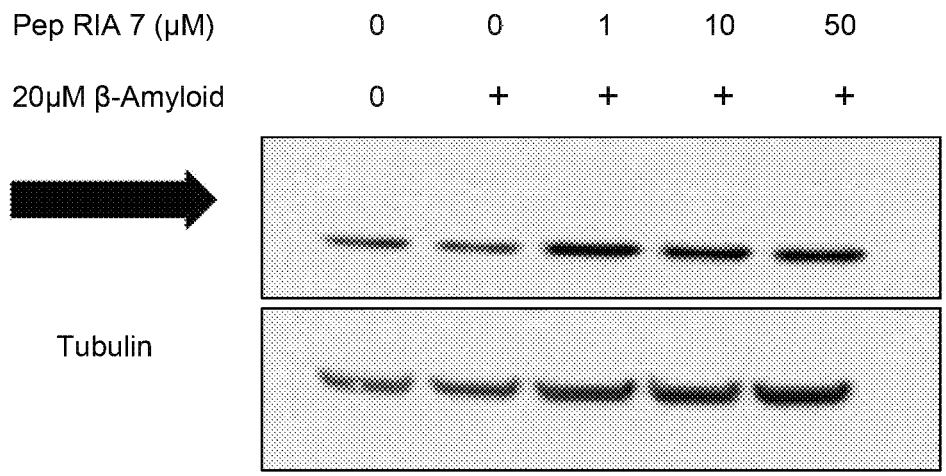
Figure 66:
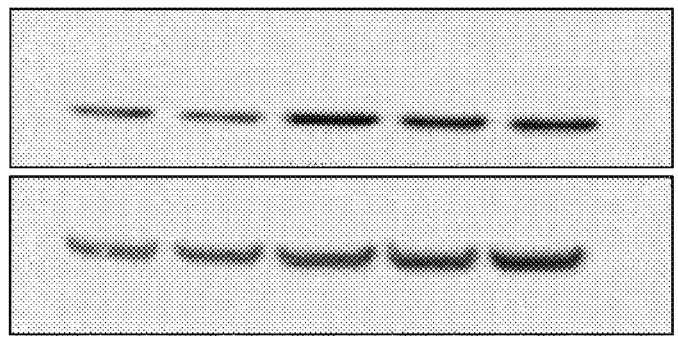
Figure 67:
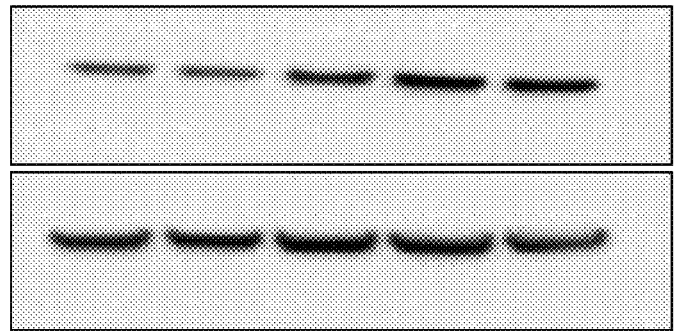
Figure 68:
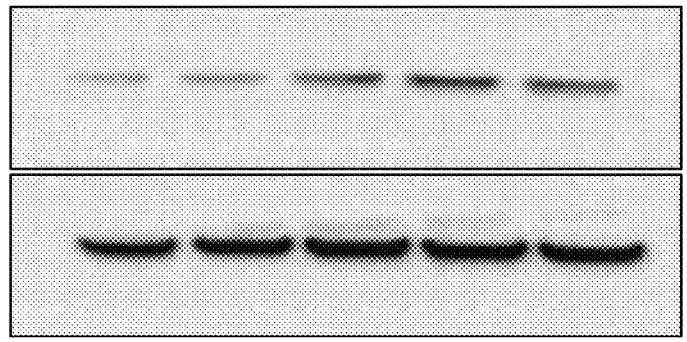
Figure 69:
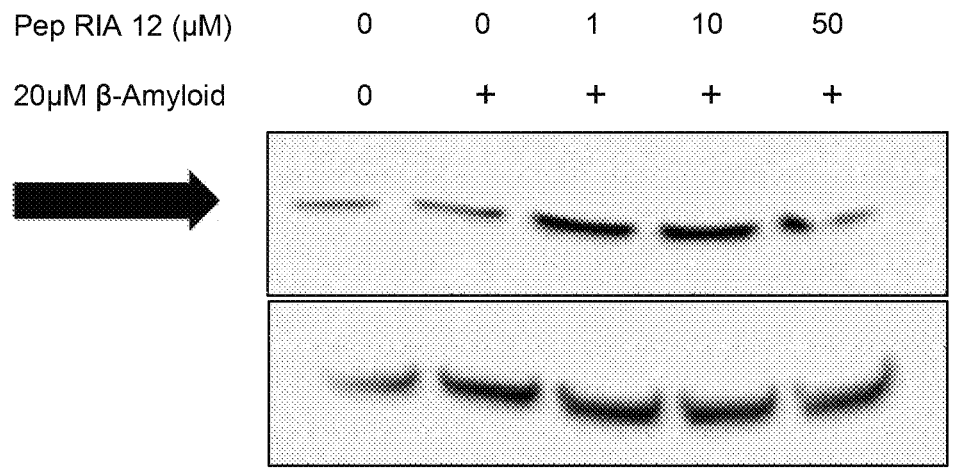
Figure 70:
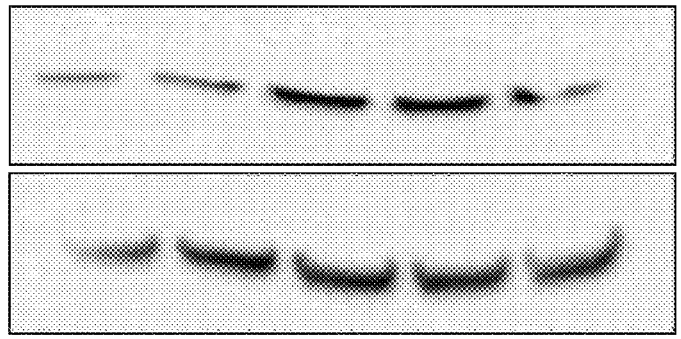
Figure 71:
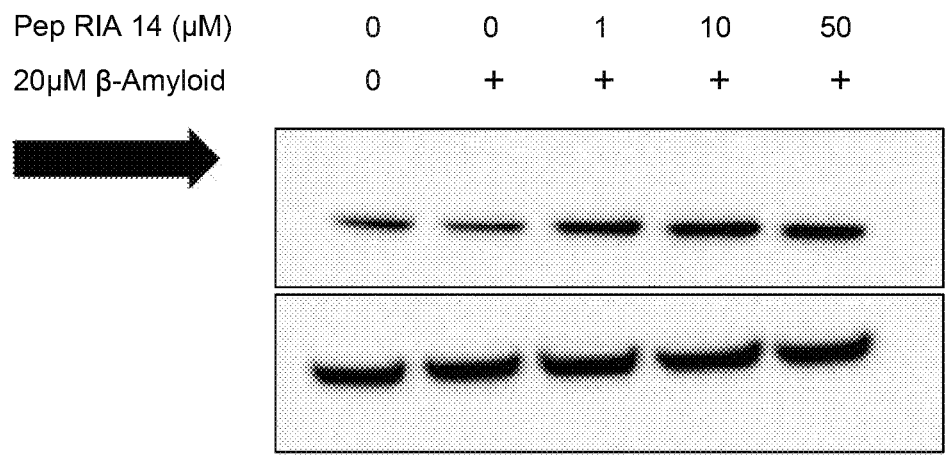
Figure 72:
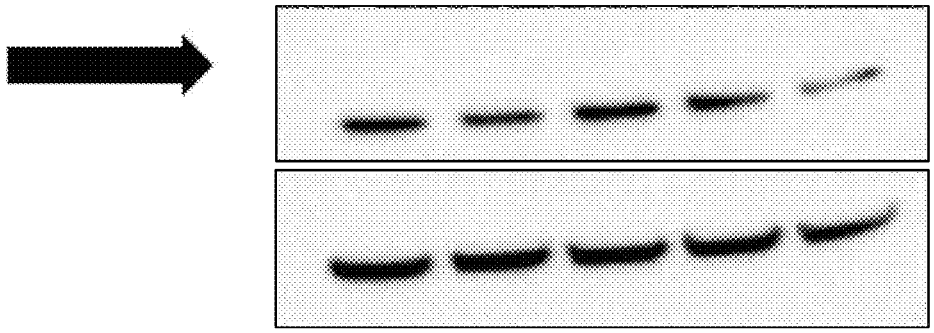
Figure 73:
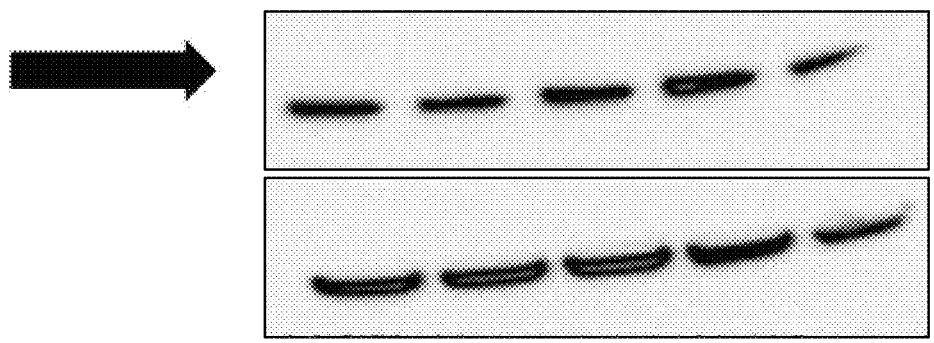
Figure 74:
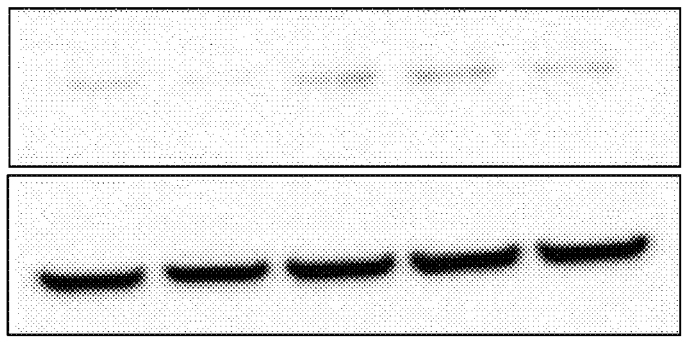
Figure 75:
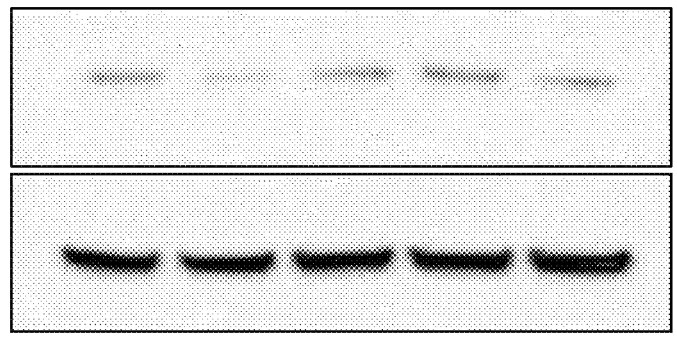
Figure 76:
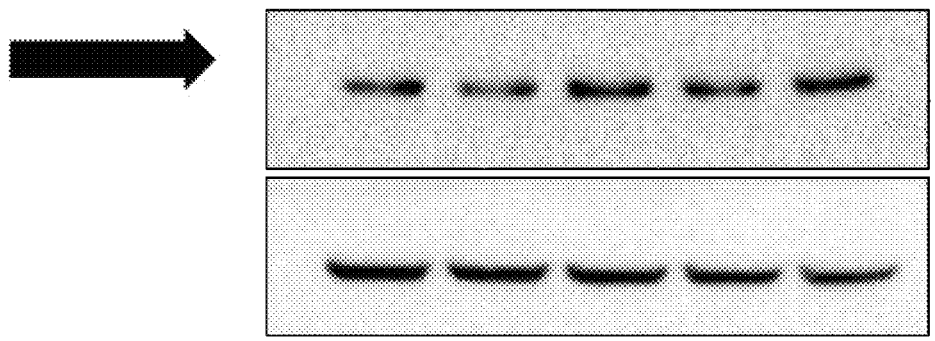
Figure 77:
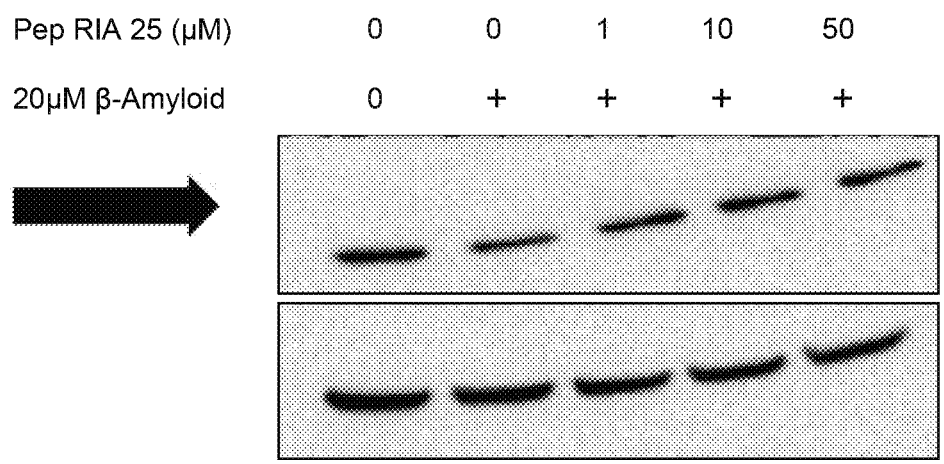
Figure 78:
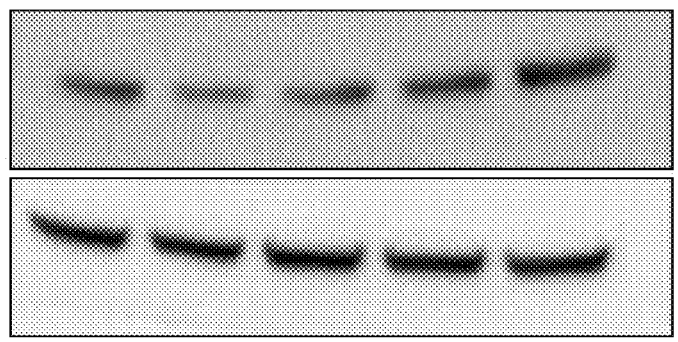
Figure 79:
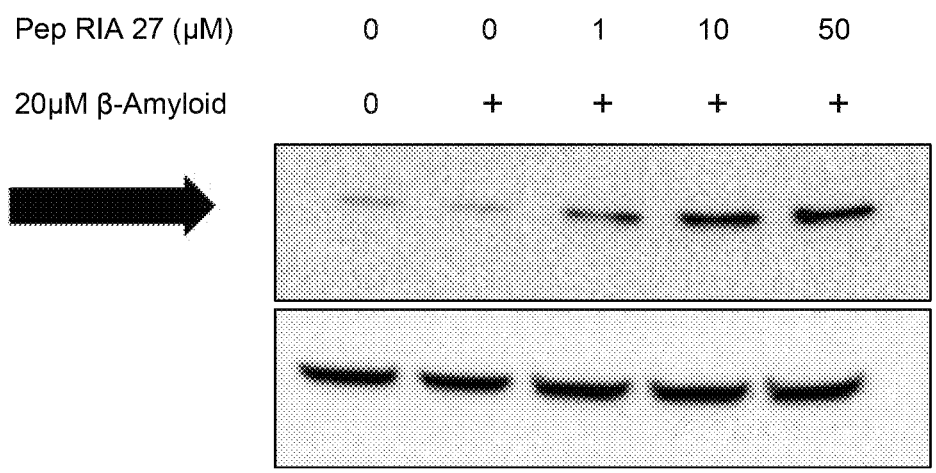
Figure 80:
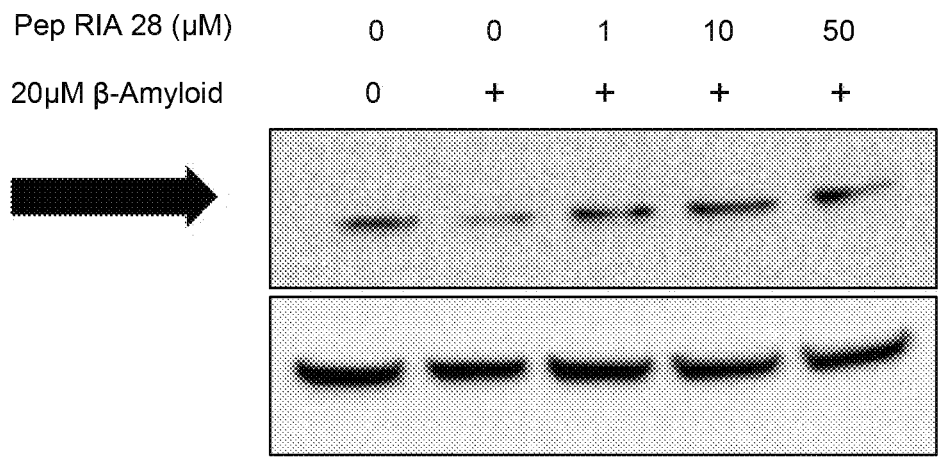
Figure 81:
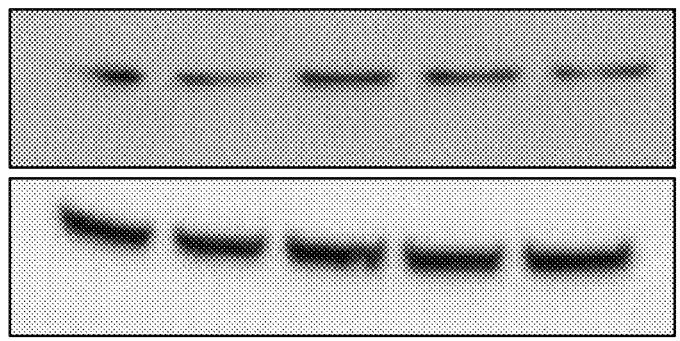
Figure 82:
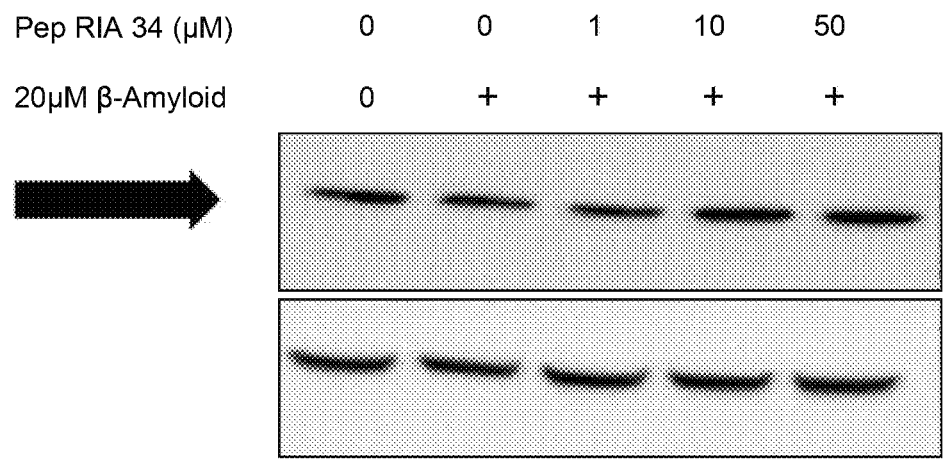
Figure 83:
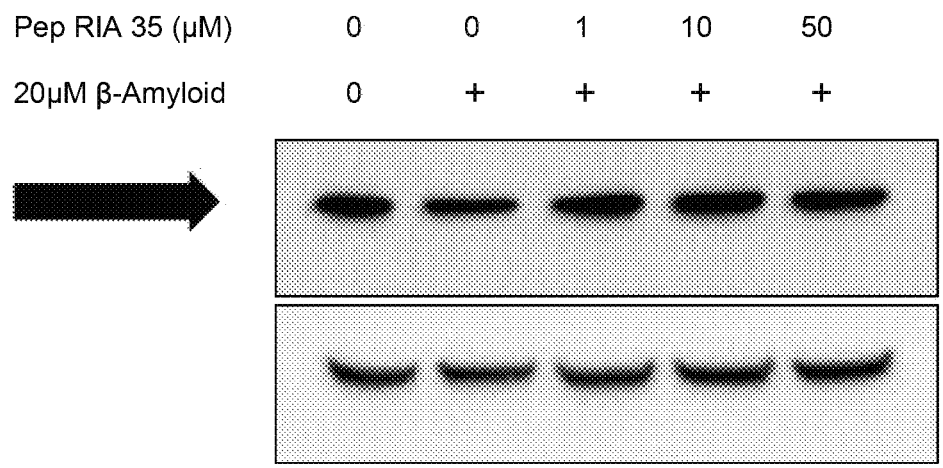
Figure 84:
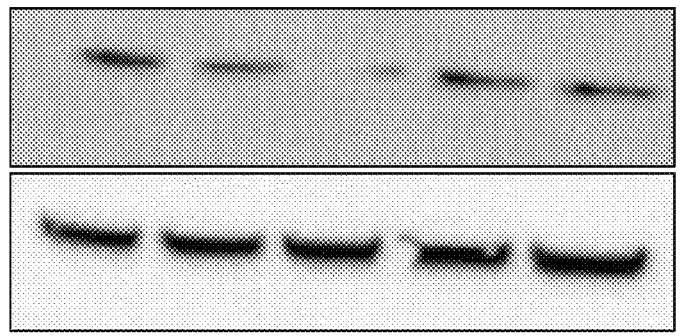
Figure 85:
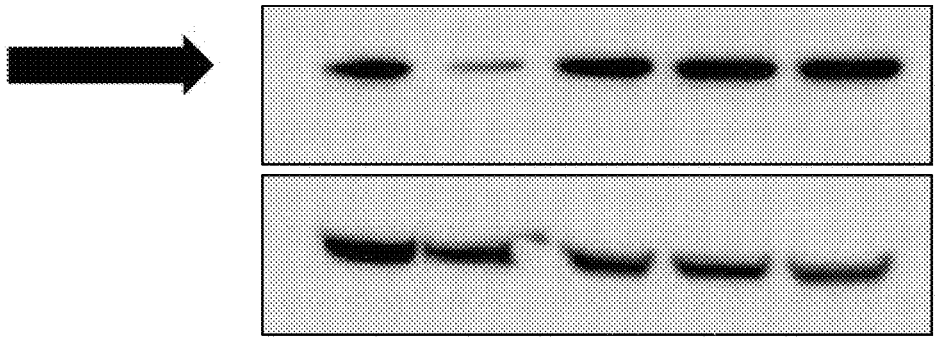
Figure 86:
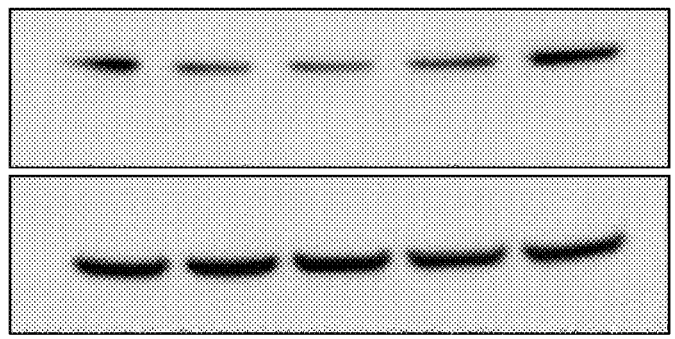
Figure 87:
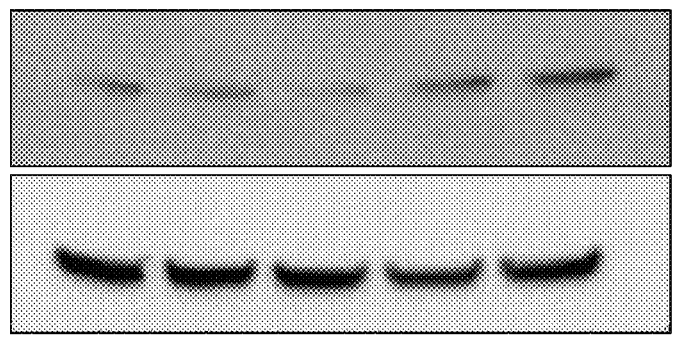
Figure 88:
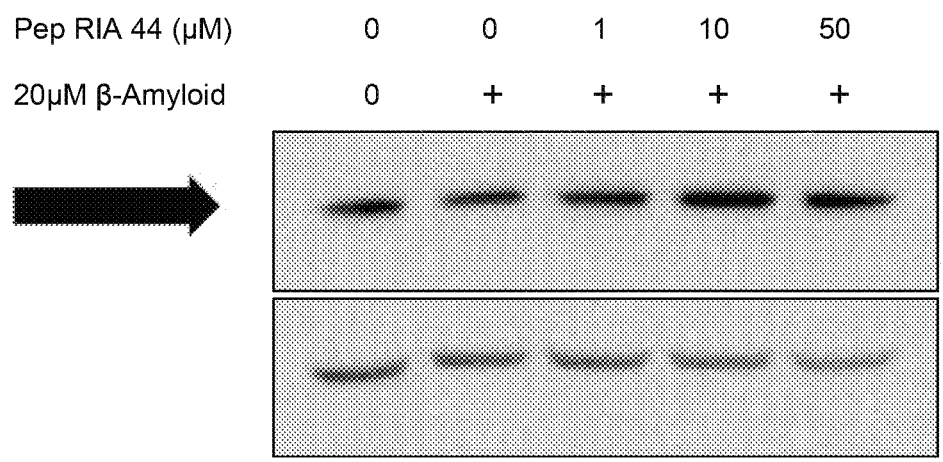
Figure 89:
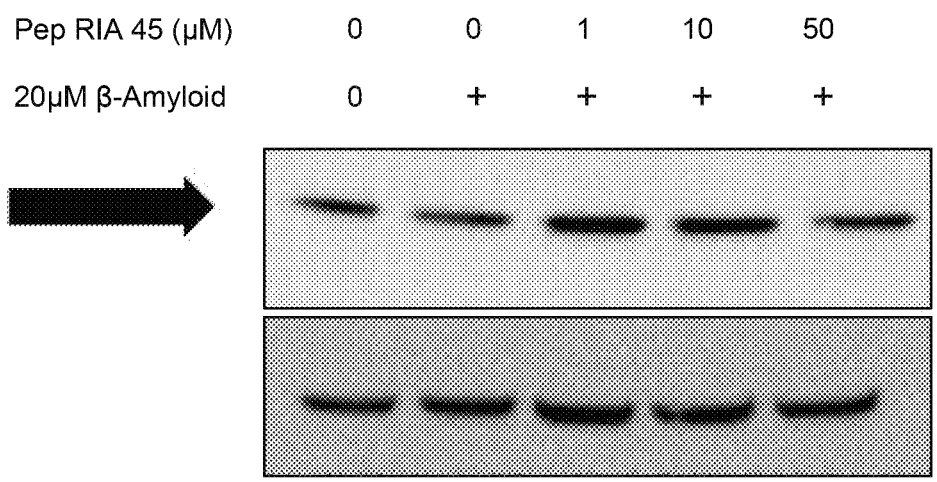
Figure 90:
Figure 91:
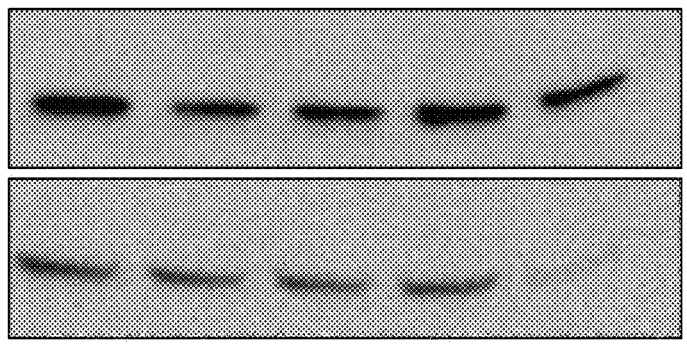
Figure 92:
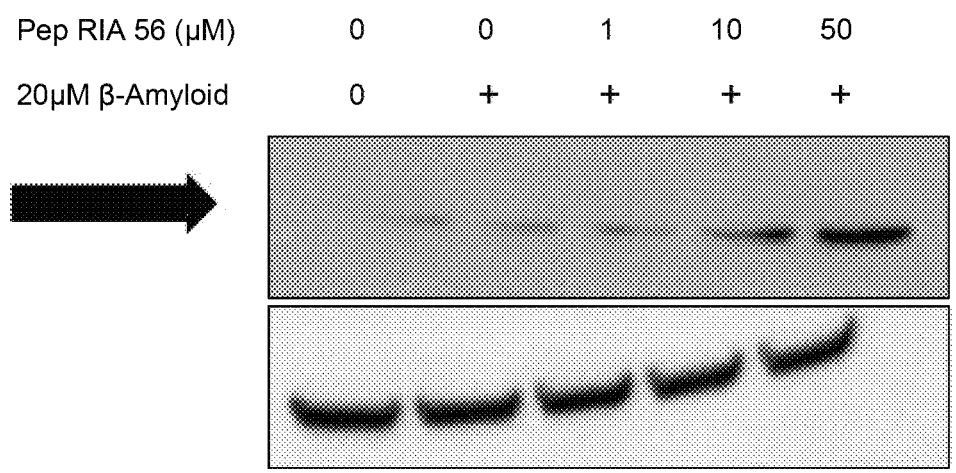
Figure 93:
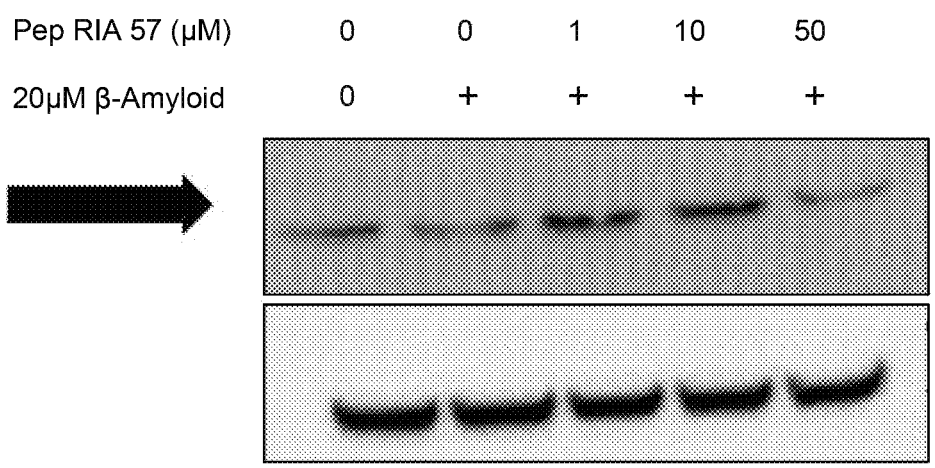
Figure 94:
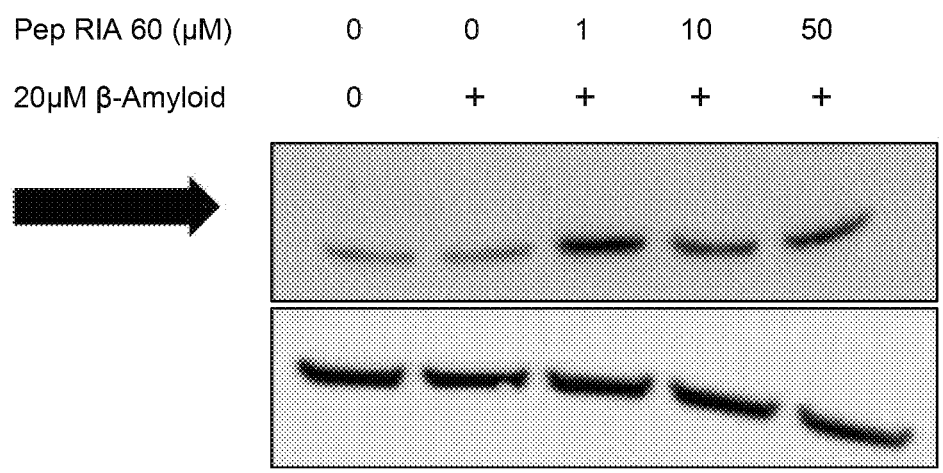
Figure 95:
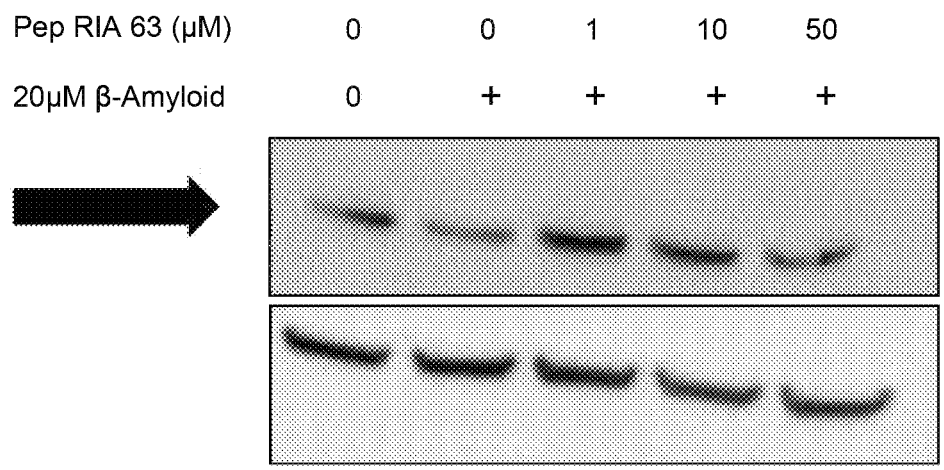
Figure 96:
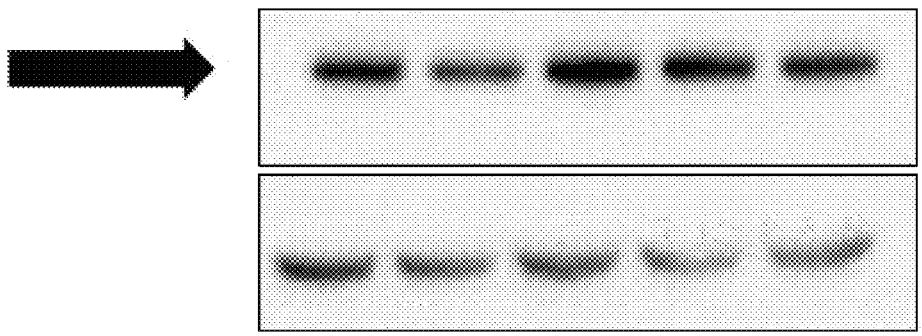
Figure 97:
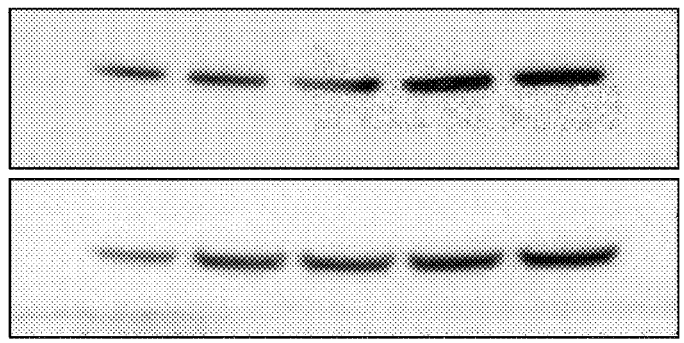
Figure 98:
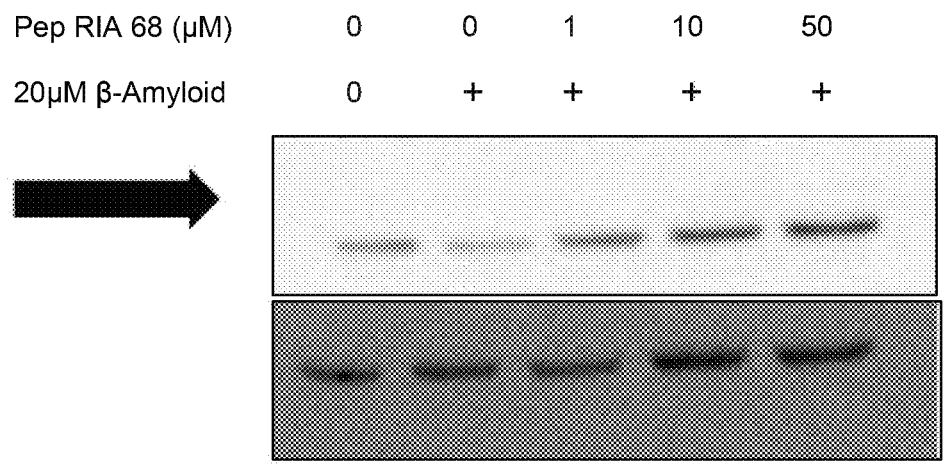
Figure 99:
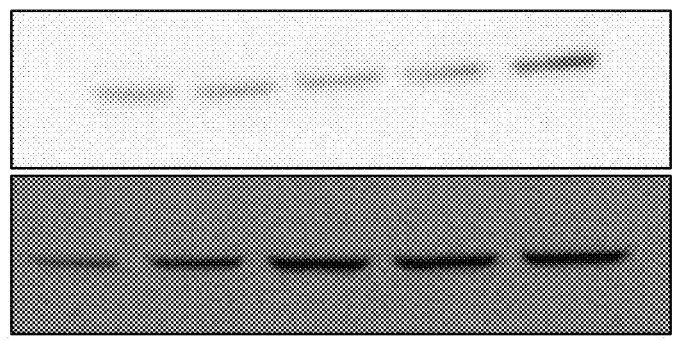
Figure 100:
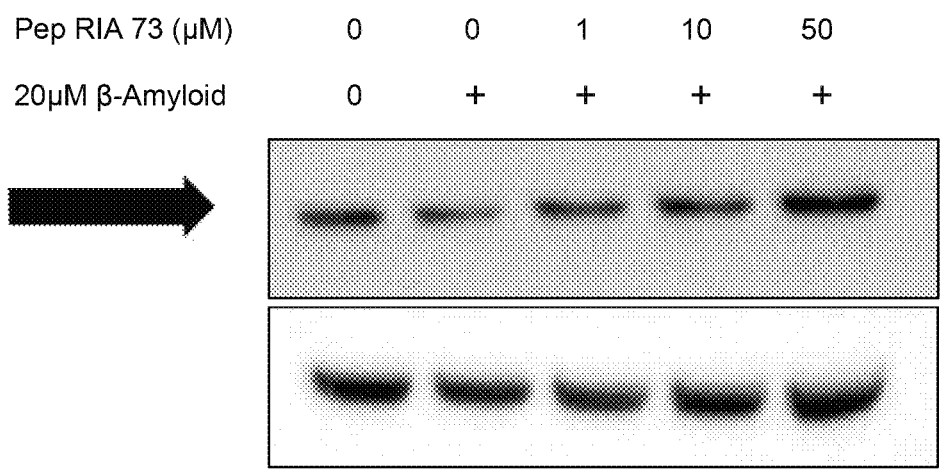
Figure 101:
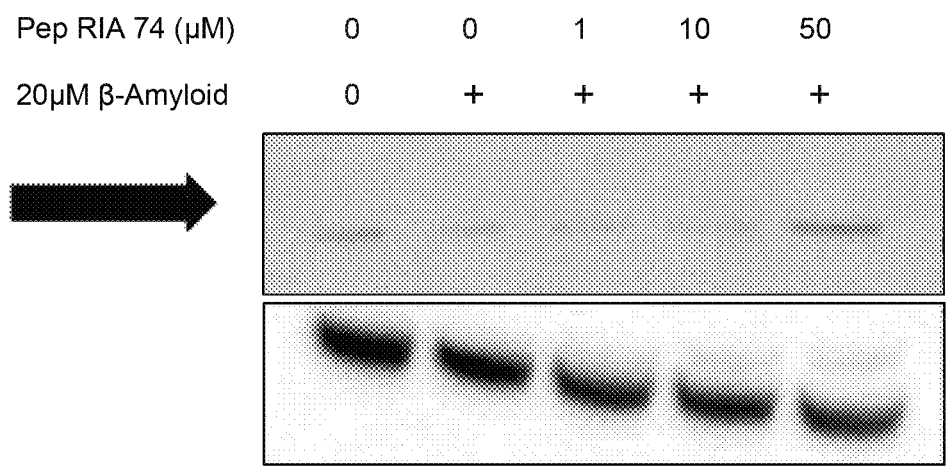
Figure 102:
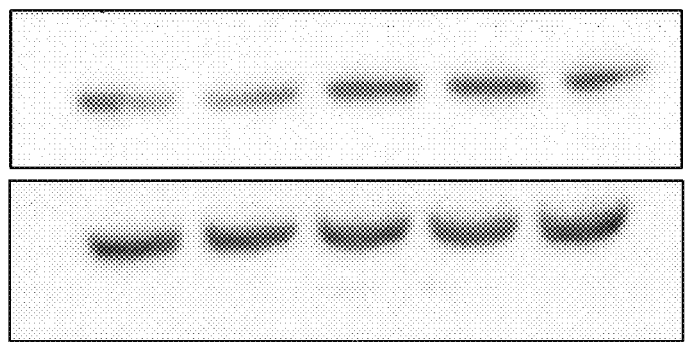
Figure 103:
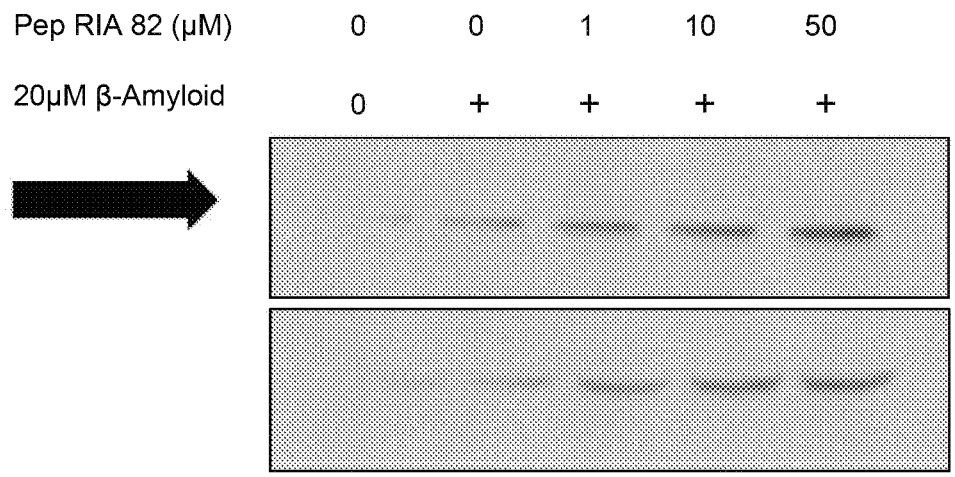
Figure 104:
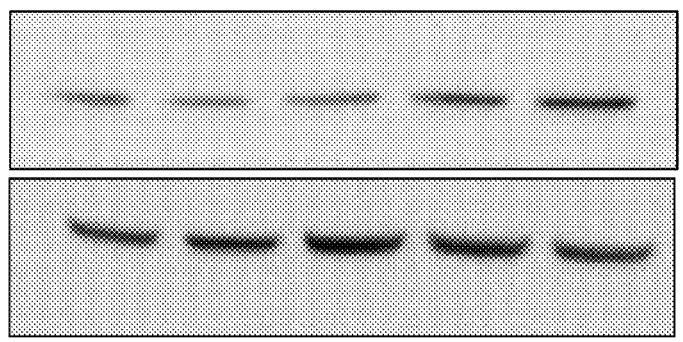
Figure 105:
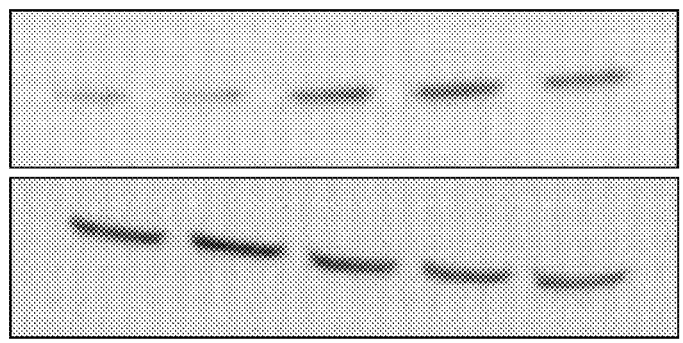
Figure 106:
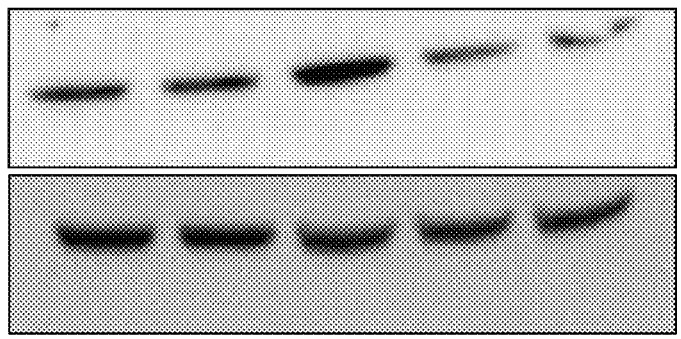
Figure 107:
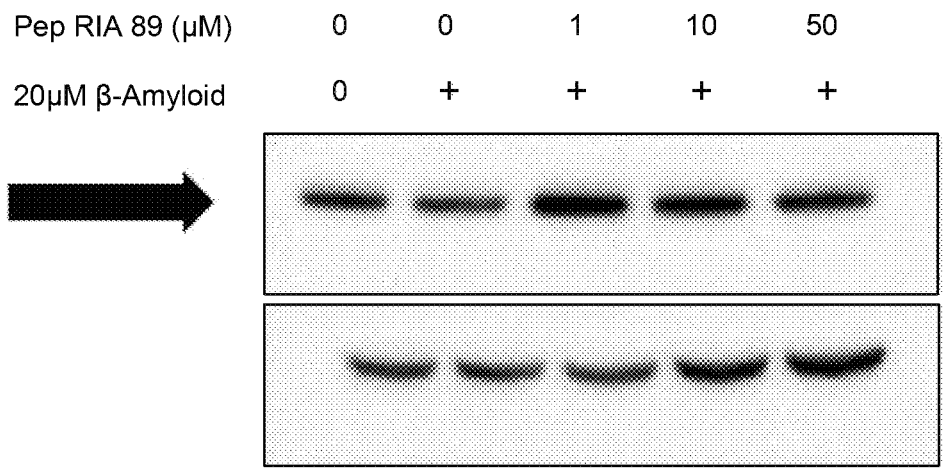
Figure 108:
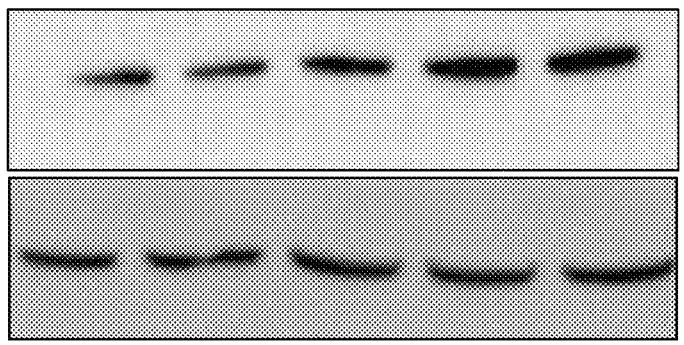
Figure 109:
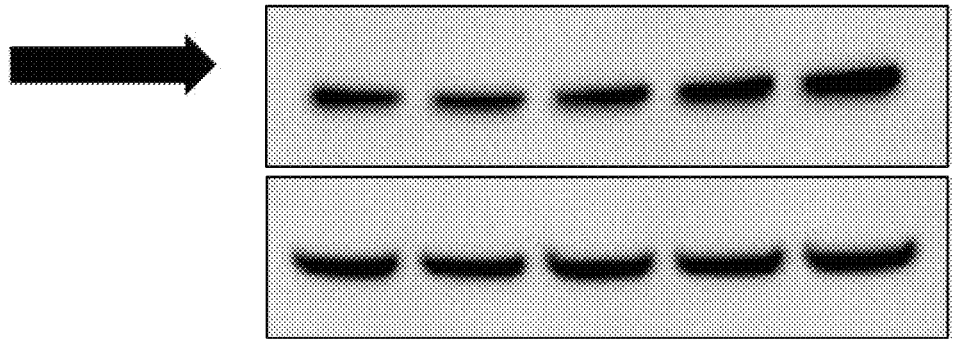
Figure 110:
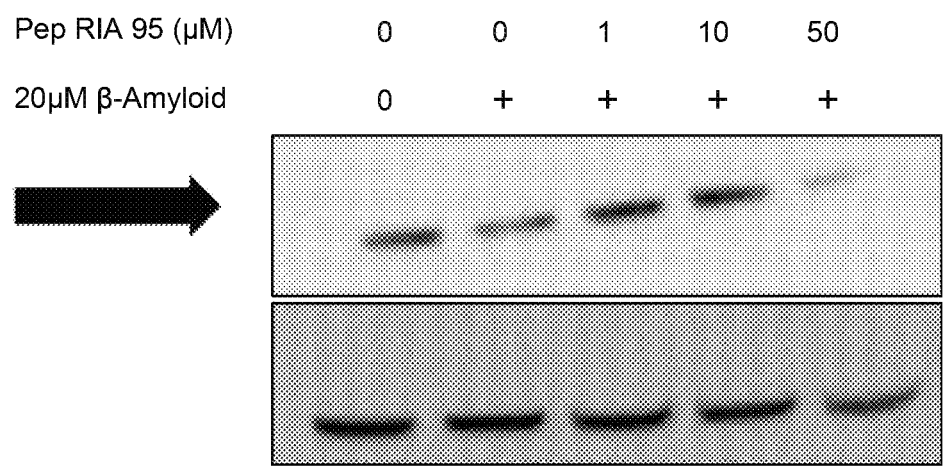
Figure 111:
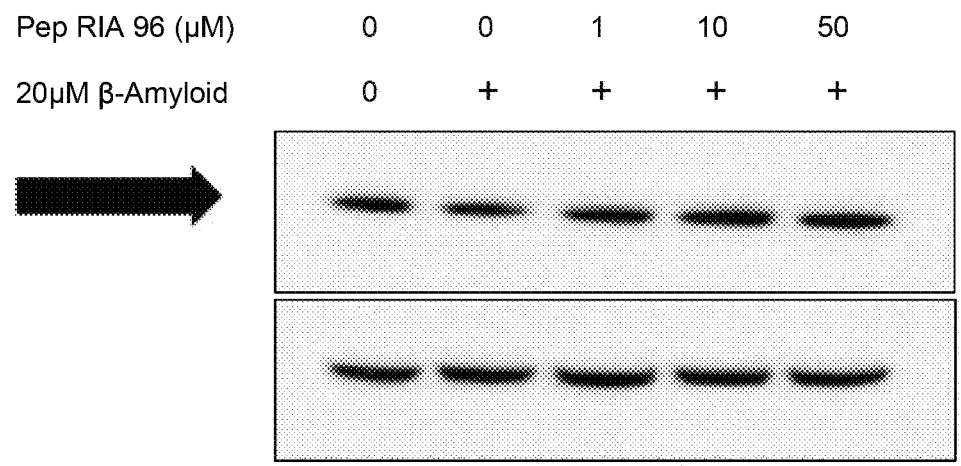
Figure 112:
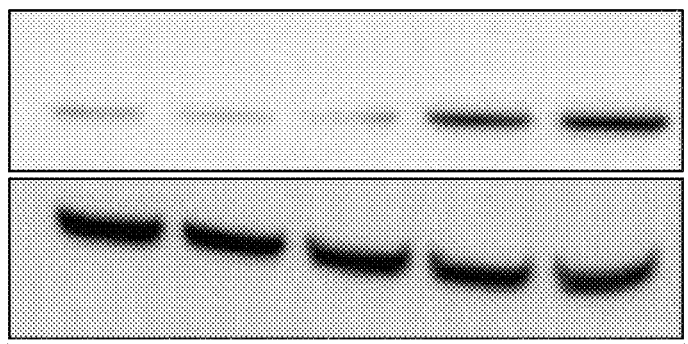
Figure 113:
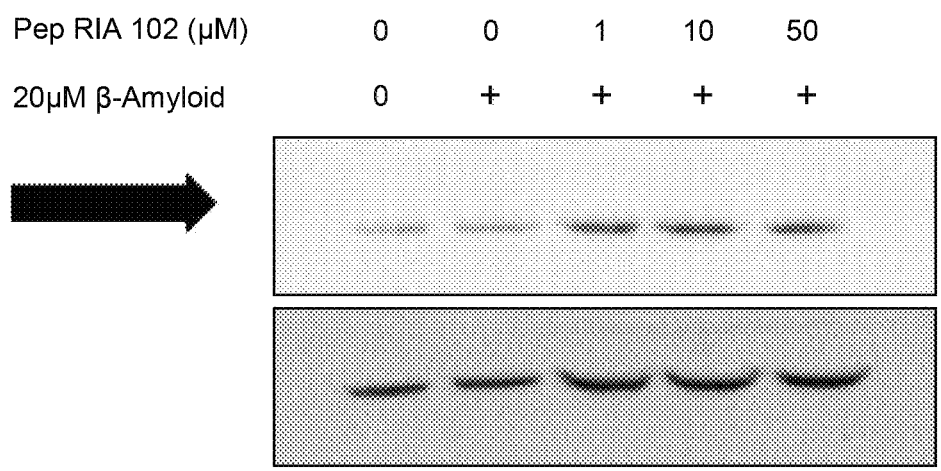
Figure 114:
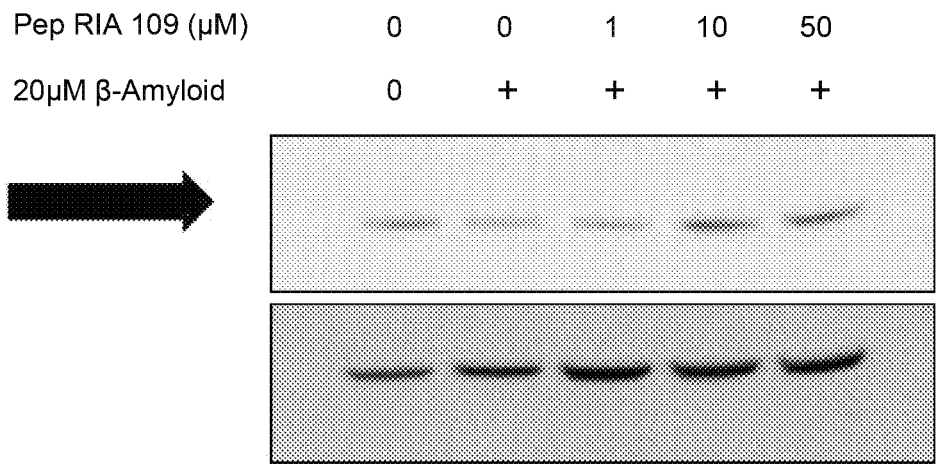
Figure 115:
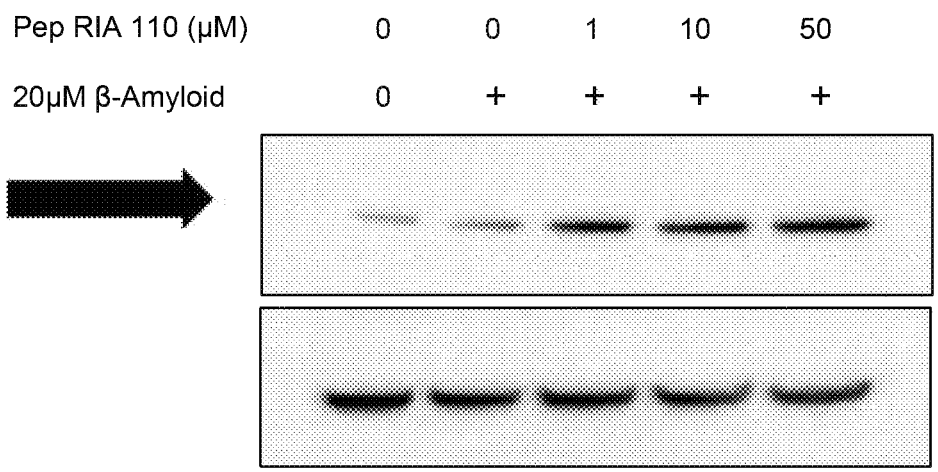
Figure 116:
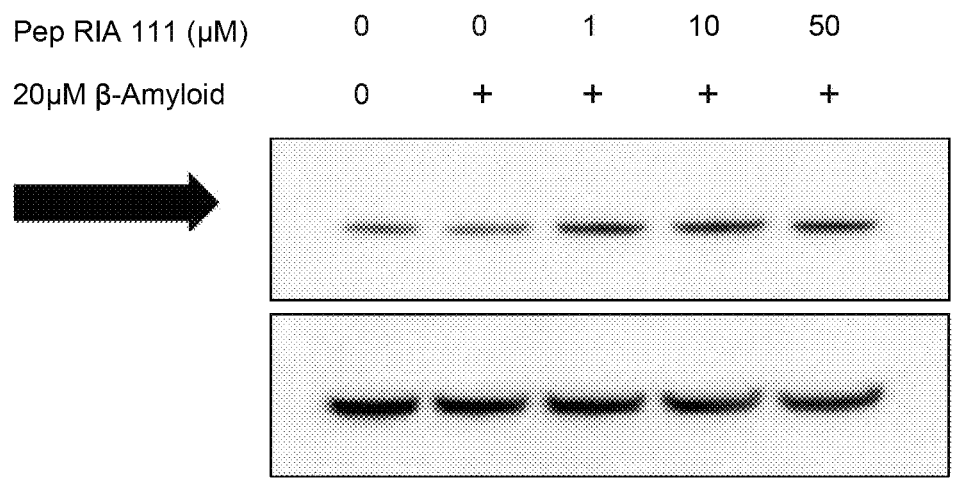
Figure 117:
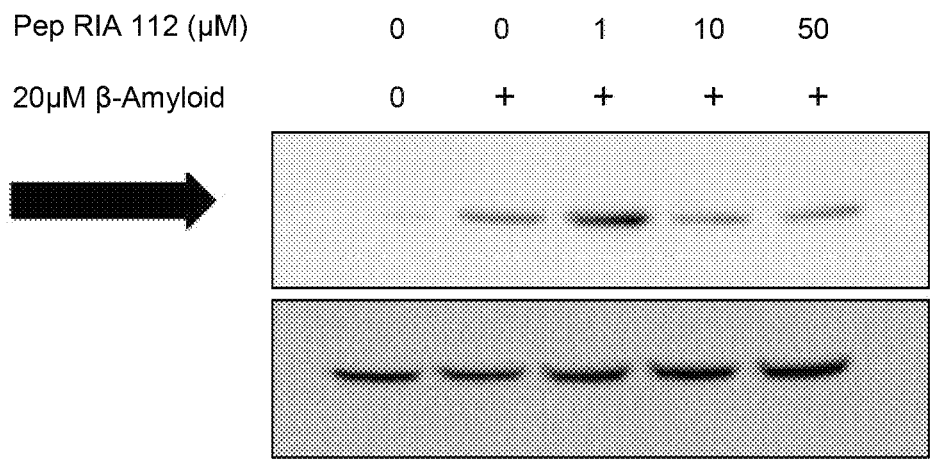
Figure 118:
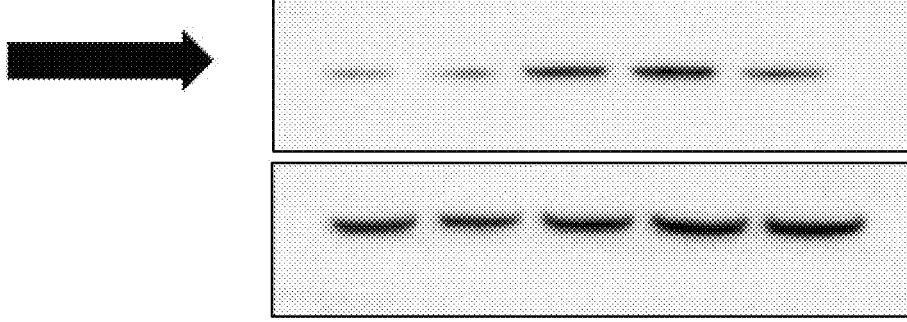
Figure 119:
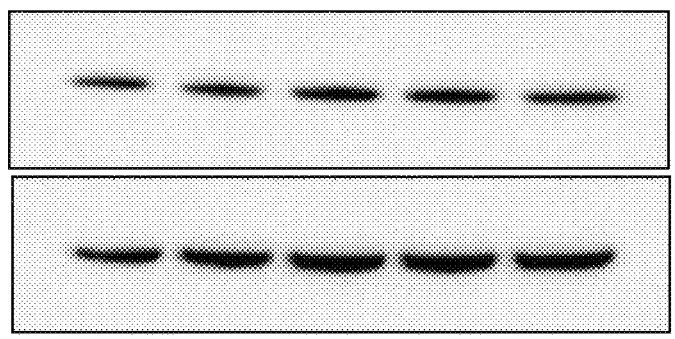
Figure 120:
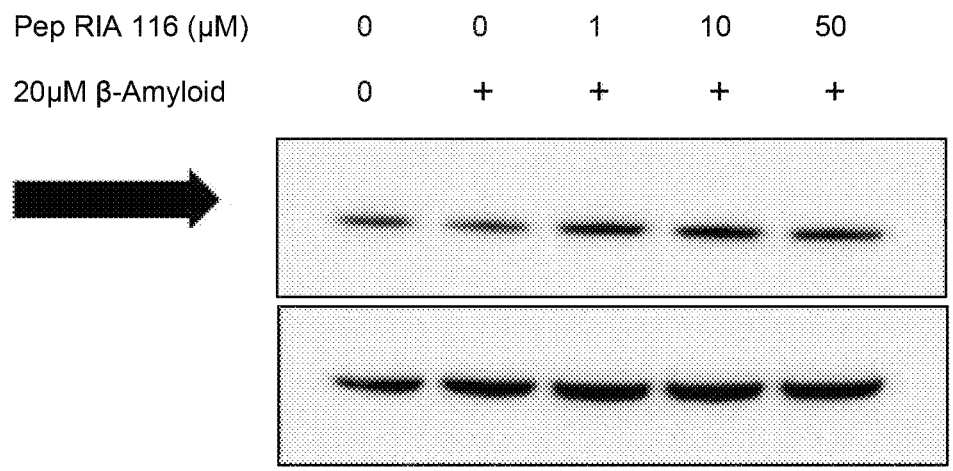
Figure 121:
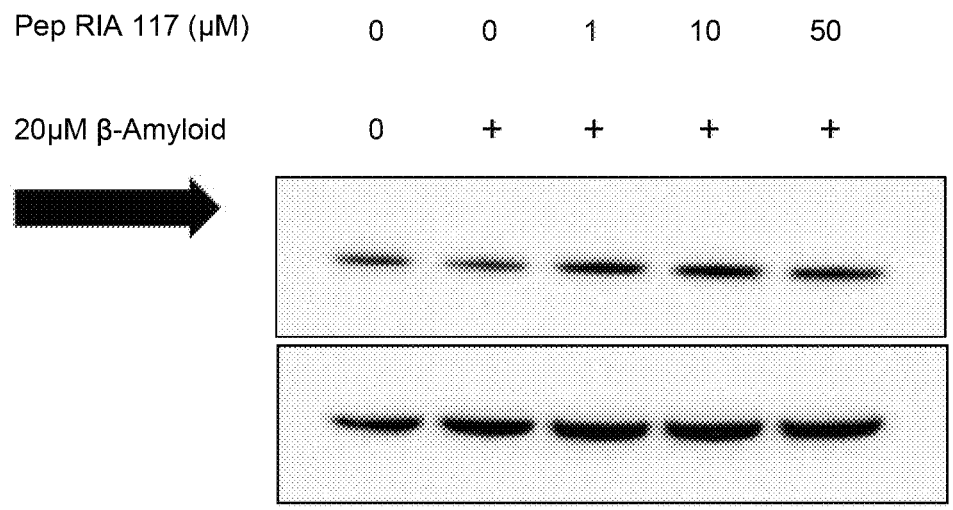
Figure 122:
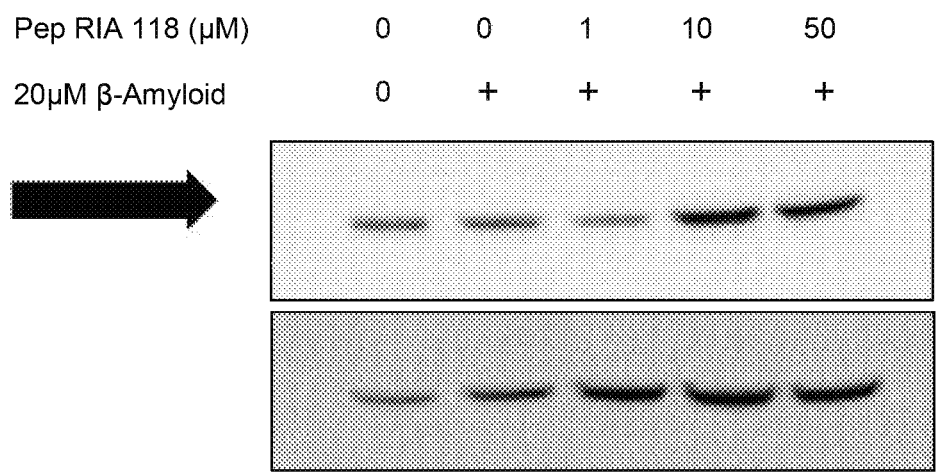
Figure 123:
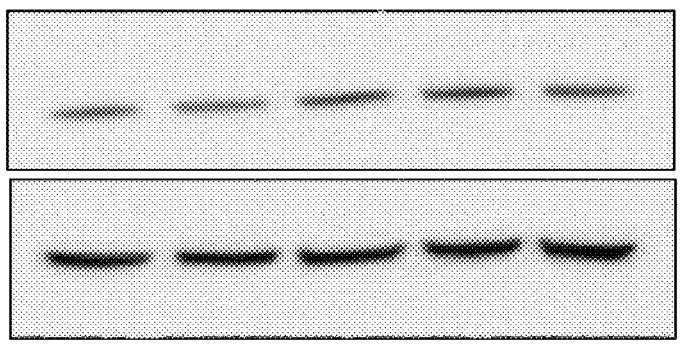
Figure 124:
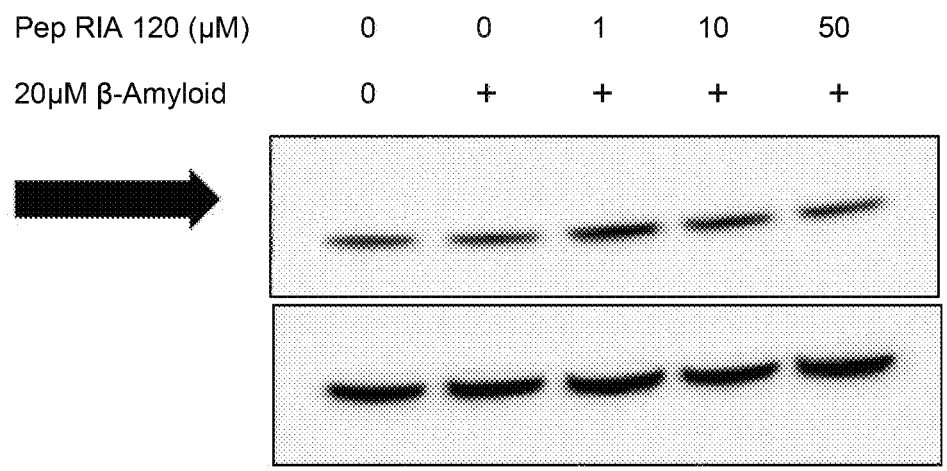
Figure 125:
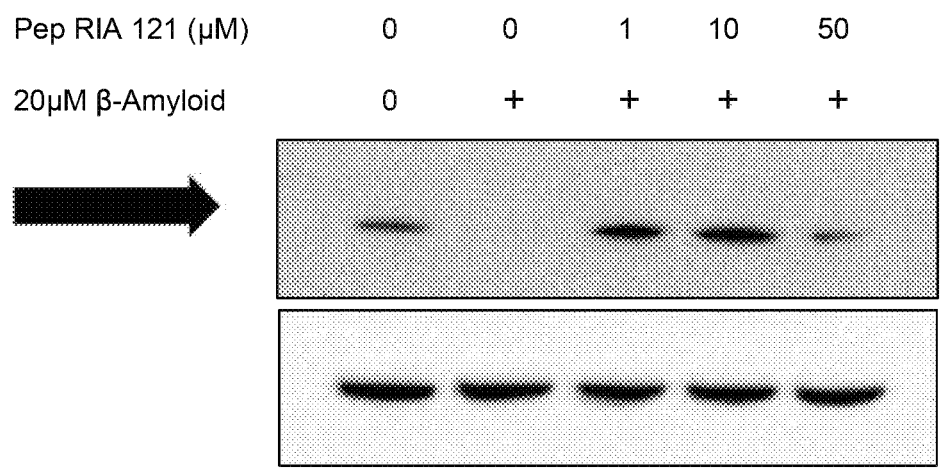
Figure 126:
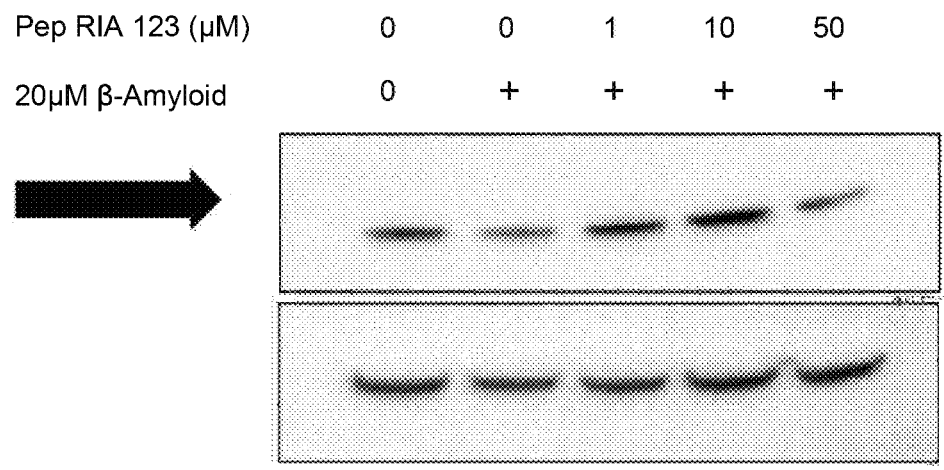
Figure 127:
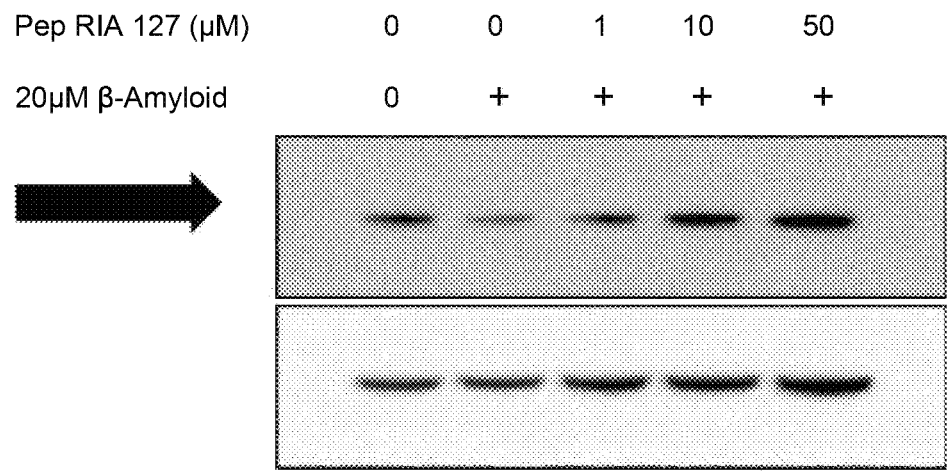
Figure 128:
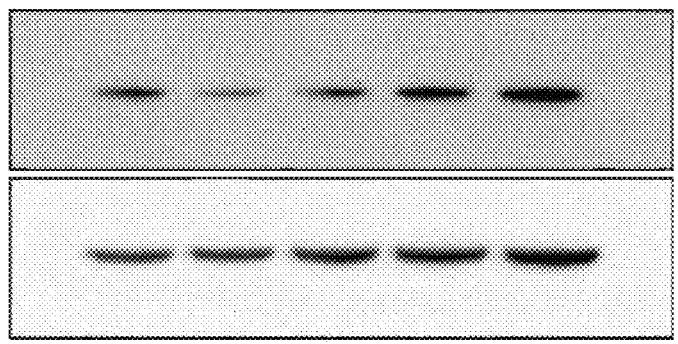
Figure 129:
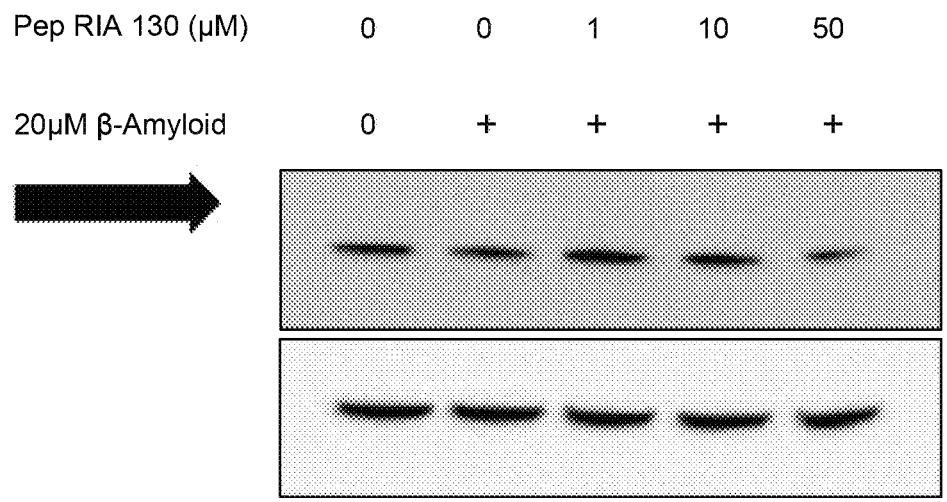
Figure 130:
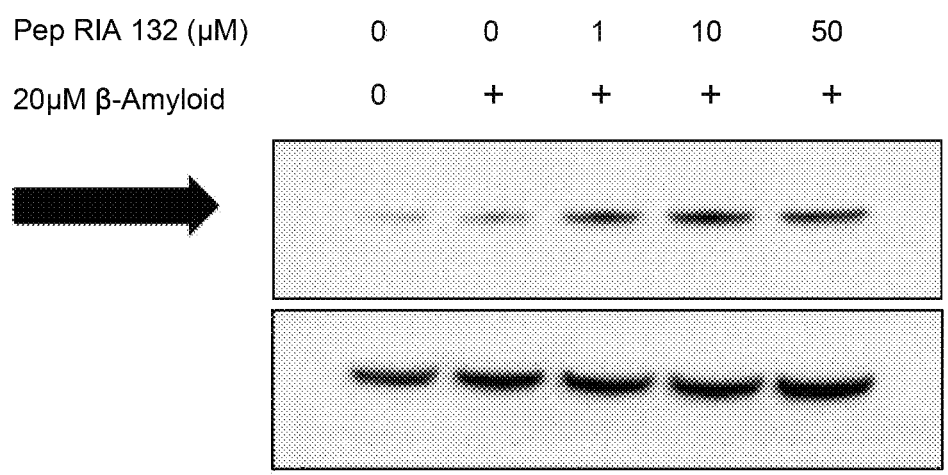
Figure 131:
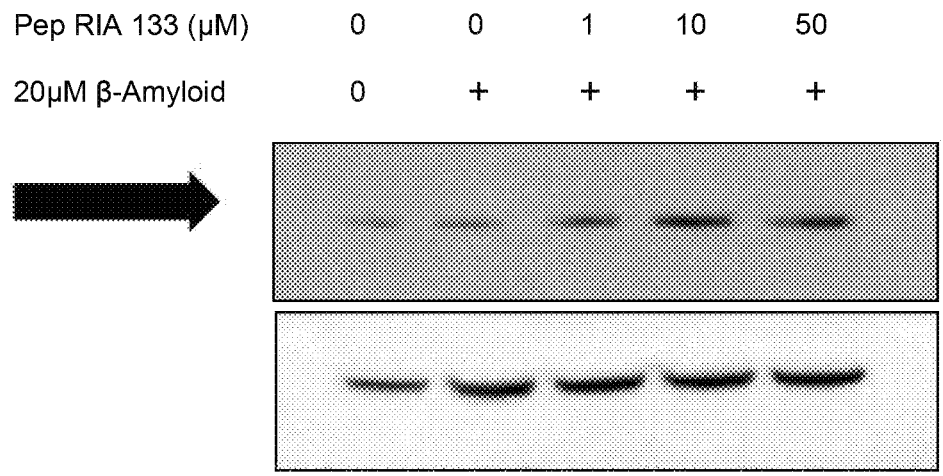
Figure 132:
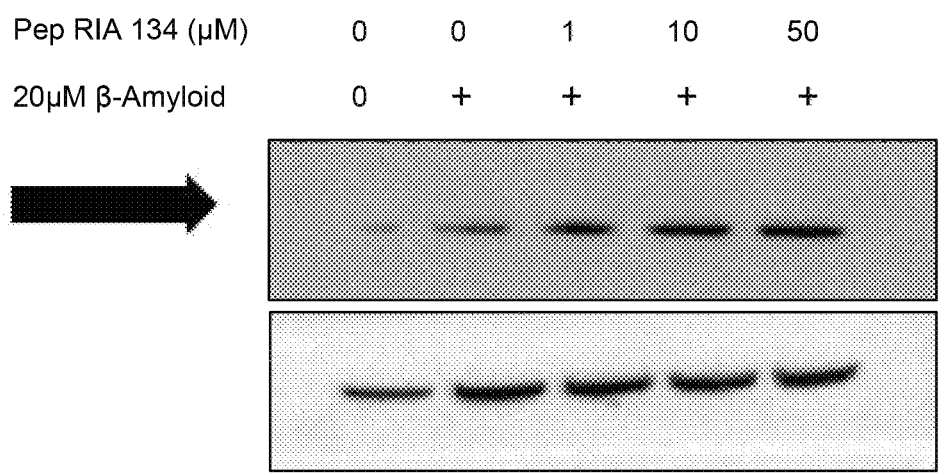
Figure 133:
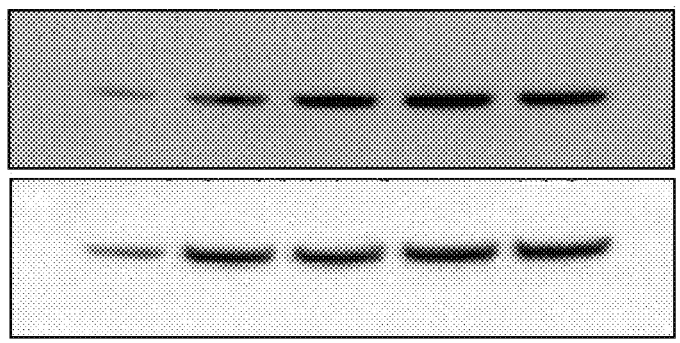
Figure 134:
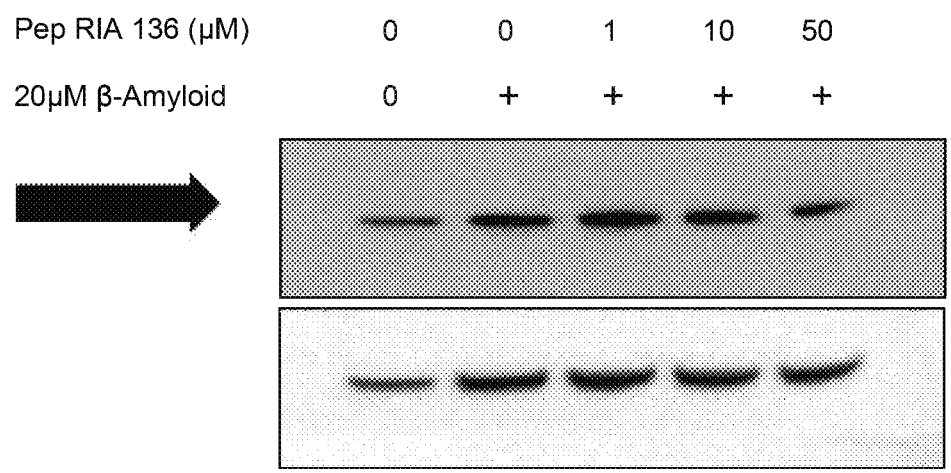
Figure 135:
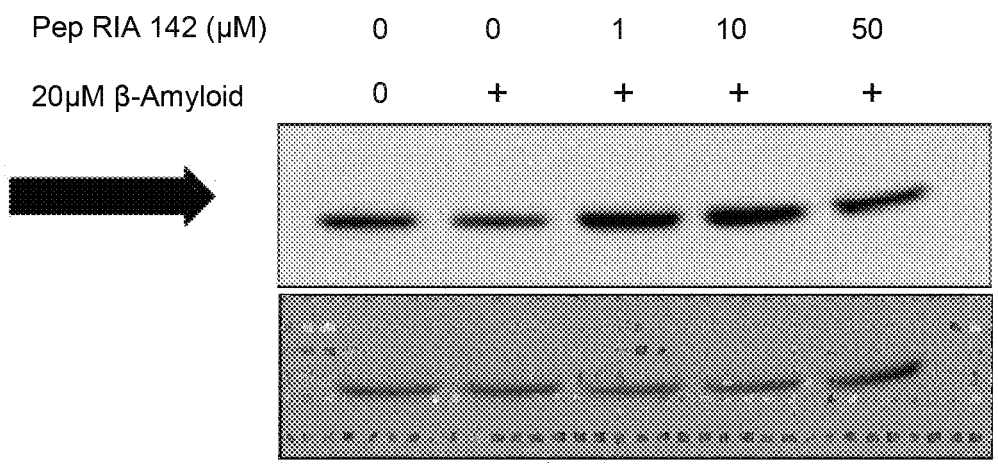
Figure 136:
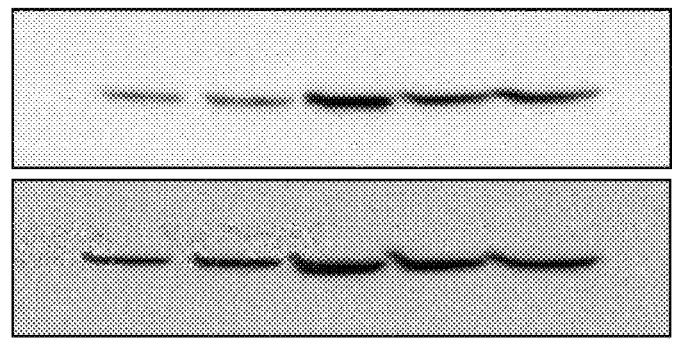
Figure 137:
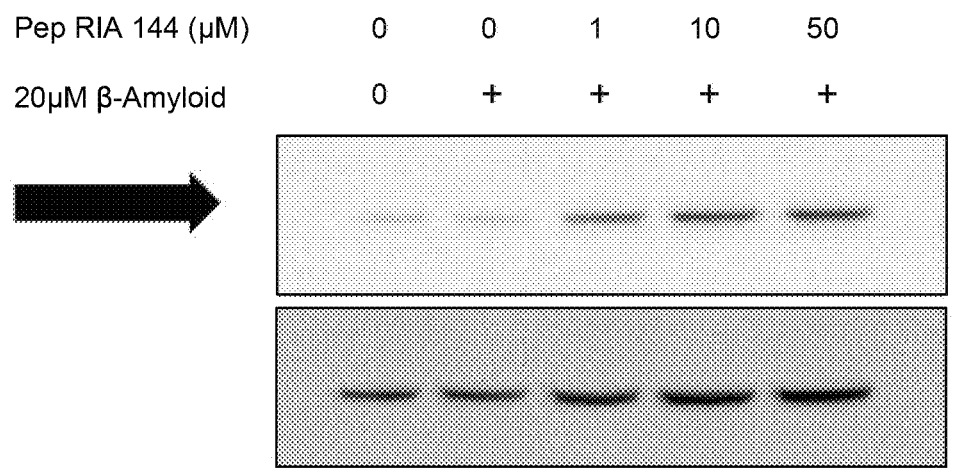
Figure 138:
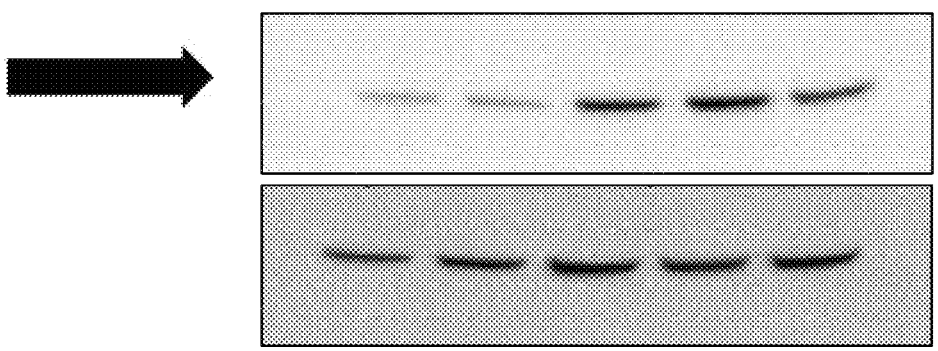
Figure 139:
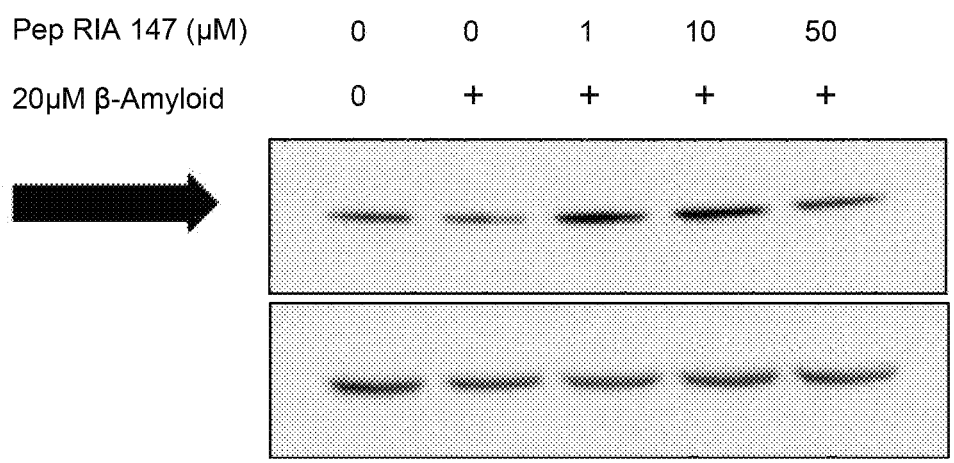
Figure 140:
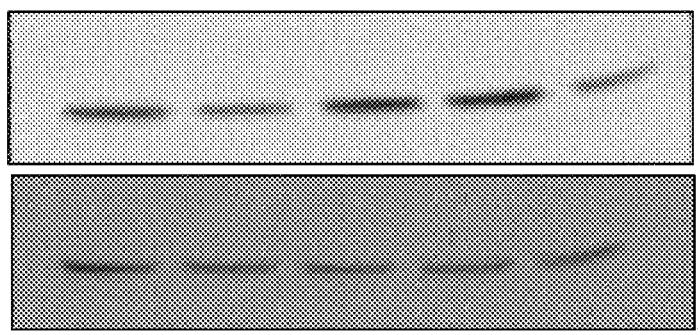
Figure 141:
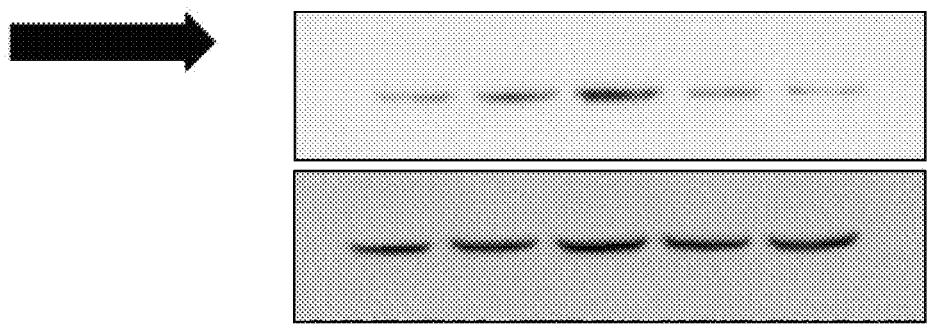
Figure 142:
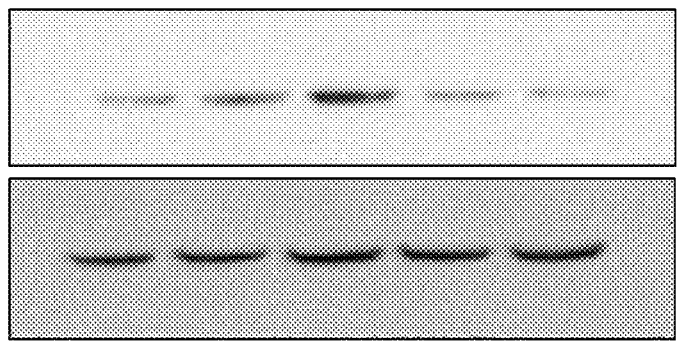
Figure 143:
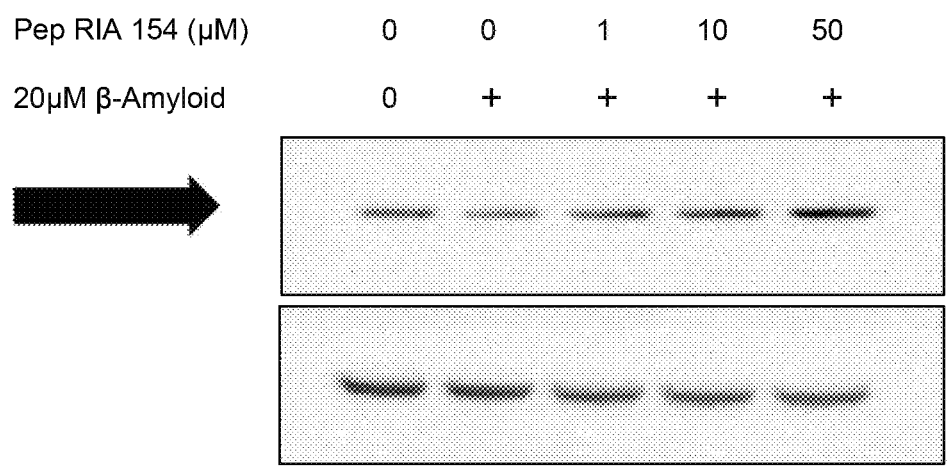
Figure 144:
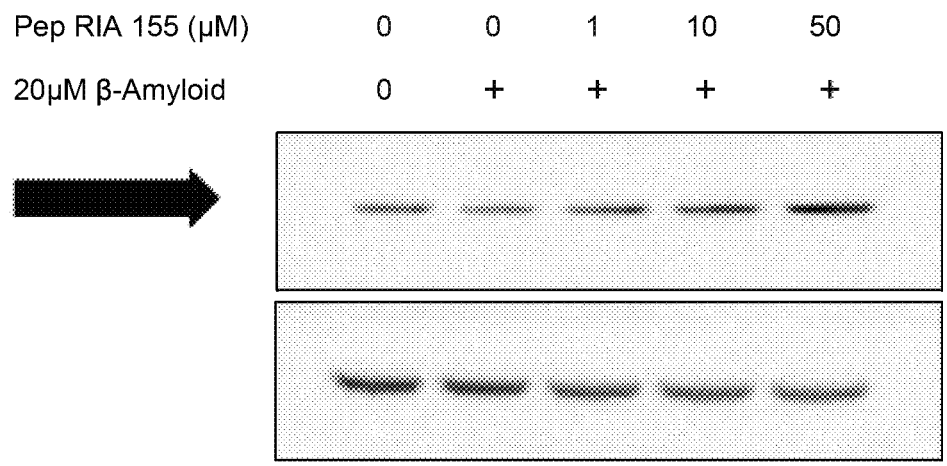
Figure 145:
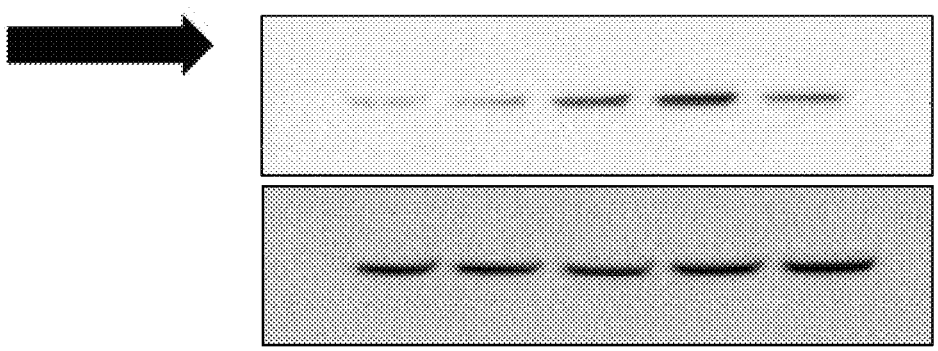
Figure 146:
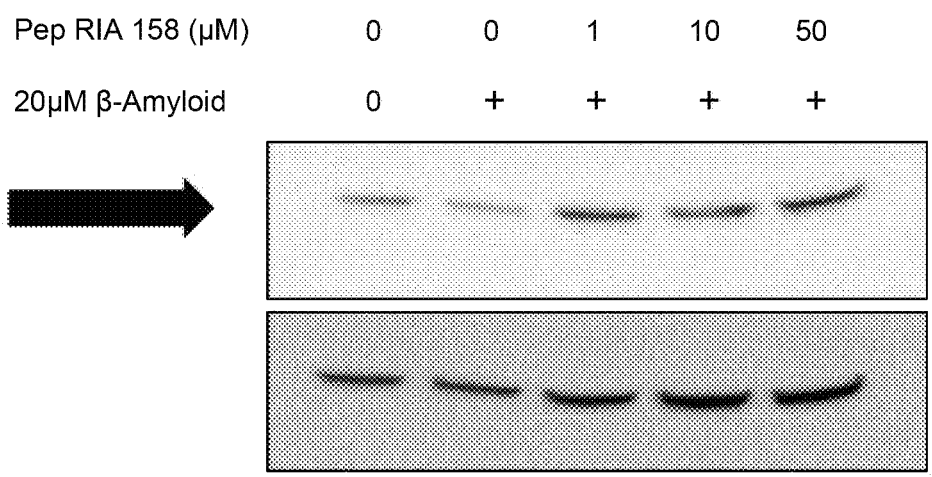
Figure 147:
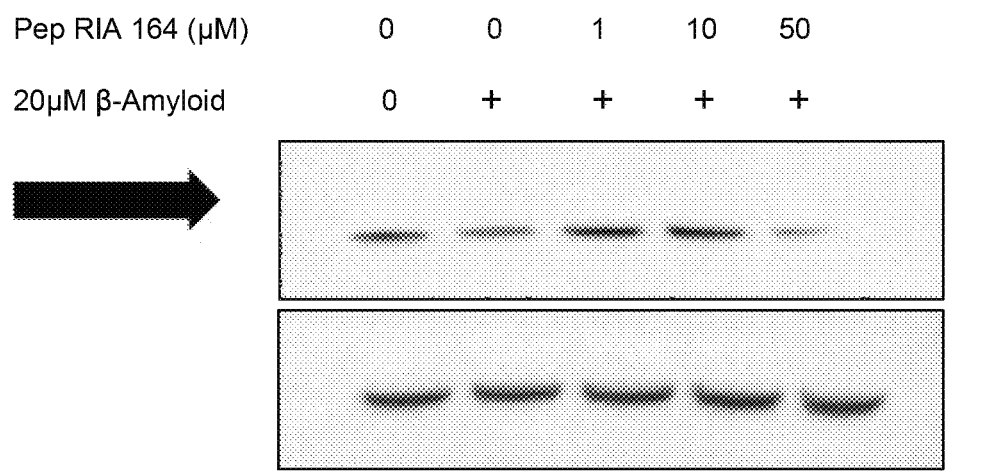
Figure 148:
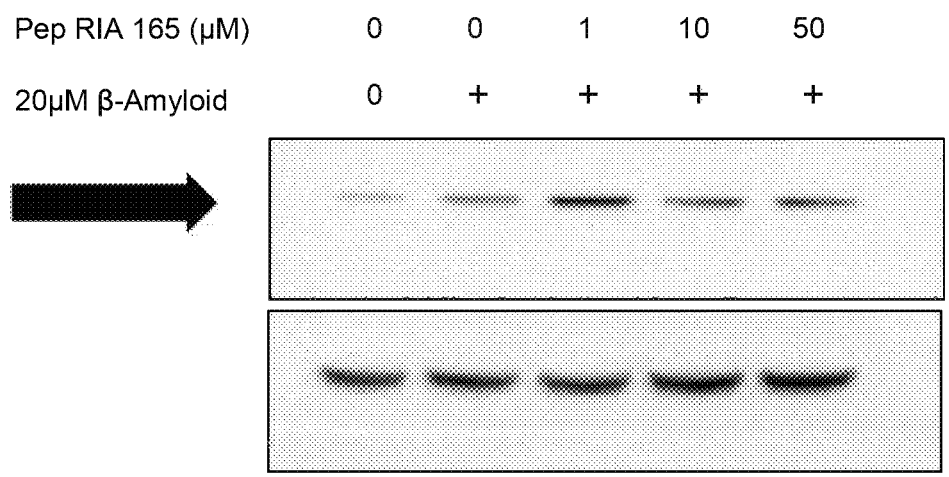
Figure 149:
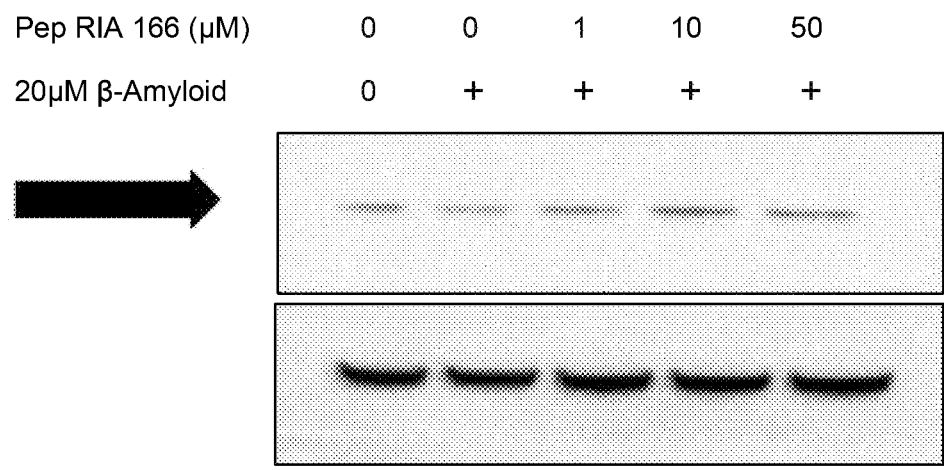
Figure 150:
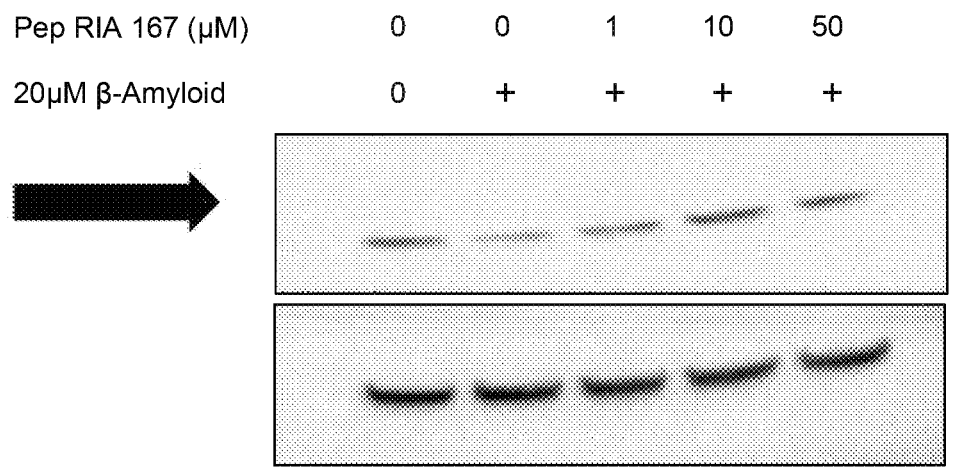
Figure 151:
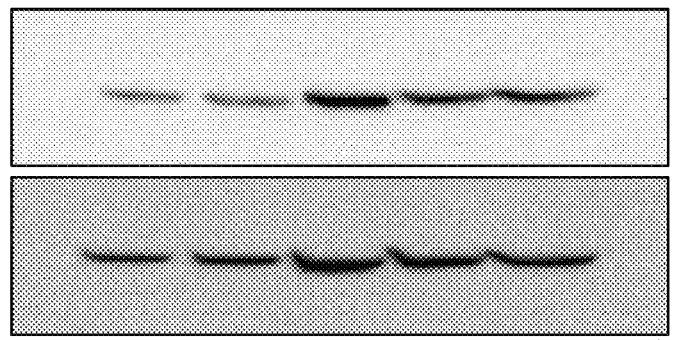
Figure 152:
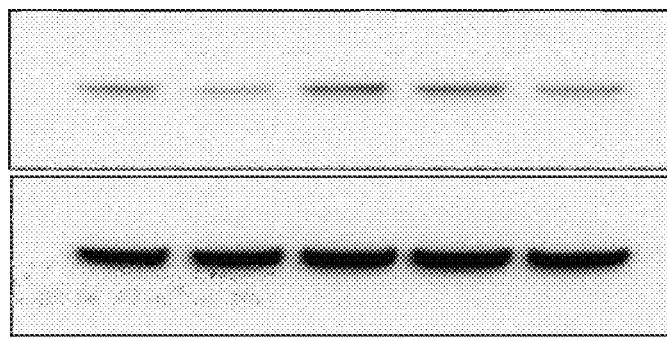
Figure 153:
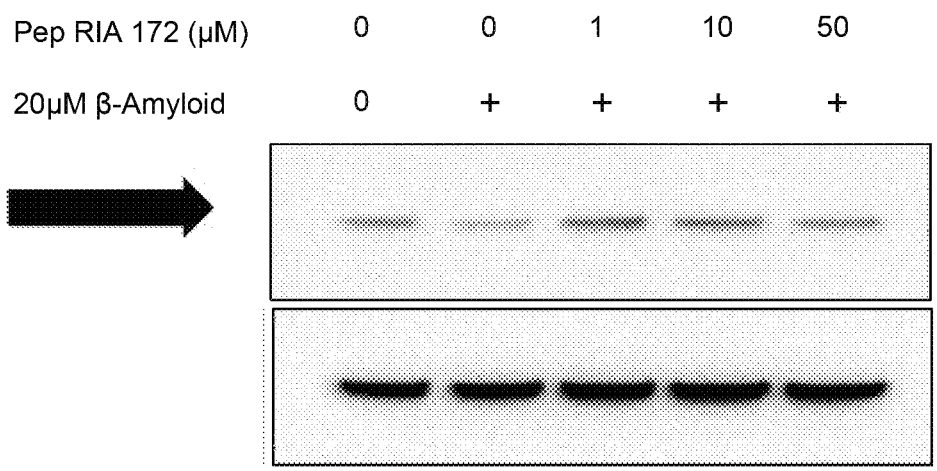
Figure 154:
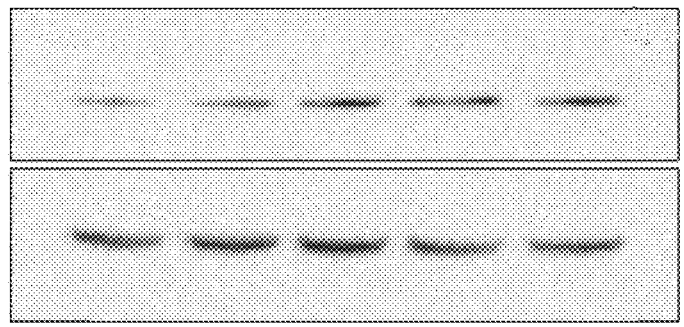
Figure 155:
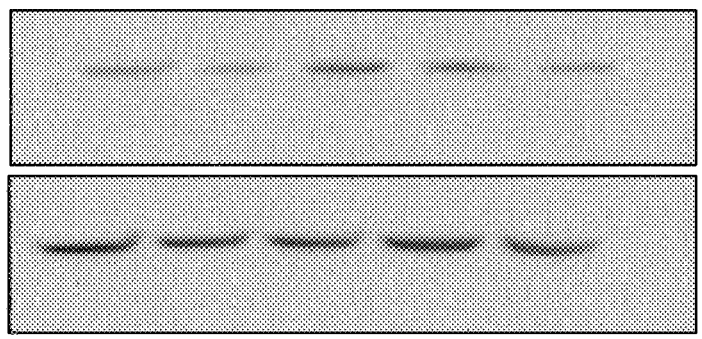
Figure 156:
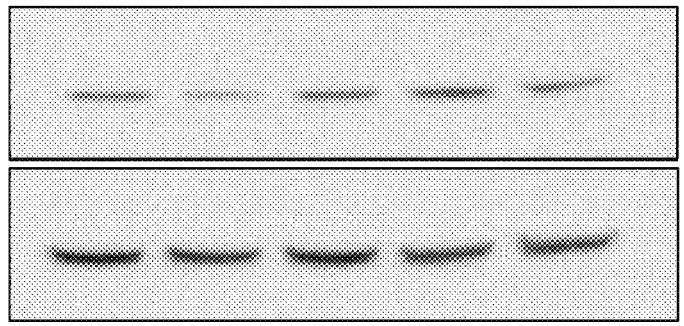
Figure 157:
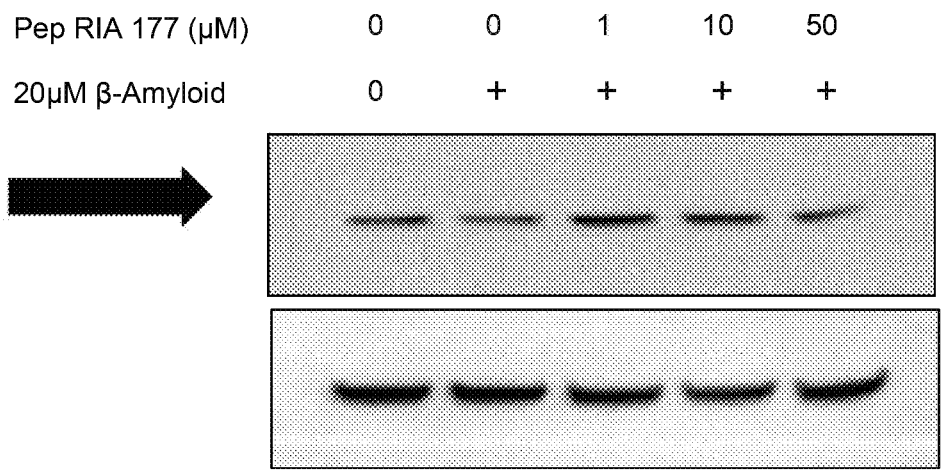
Figure 158:
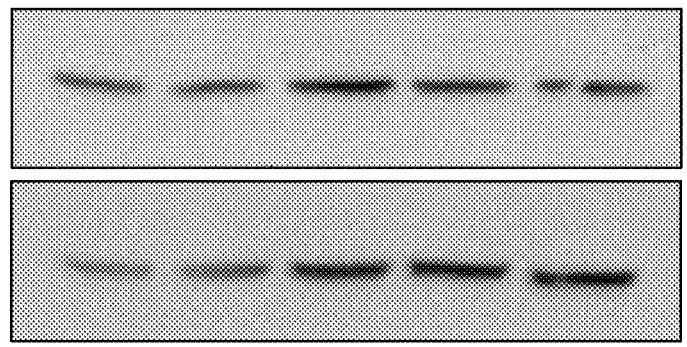
Figure 159:
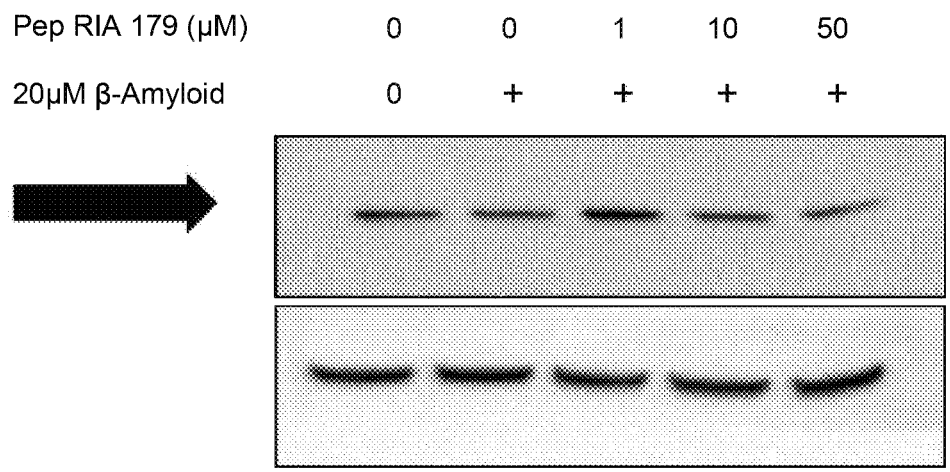

As a result of the western blot analysis, peptides showing accumulation of HMGB1 in the cell were selected. FIG. 60 to FIG. 159 are the western blot results of selected peptides. Tubulins in these figures are used for confirming protein expression. The sequences of the selected peptides are as follows:

SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 22, SEQ ID NO: 23, SEQ ID NO: 24, SEQ ID NO: 26, SEQ ID NO: 27, SEQ ID NO: 28, SEQ ID NO: 29, SEQ ID NO: 30, SEQ ID NO: 35, SEQ ID NO: 36, SEQ ID NO: 37, SEQ ID NO: 38, SEQ ID NO: 40, SEQ ID NO: 43, SEQ ID NO: 45, SEQ ID NO: 46, SEQ ID NO: 47, SEQ ID NO: 48, SEQ ID NO: 57, SEQ ID NO: 58, SEQ ID NO: 61, SEQ ID NO: 64, SEQ ID NO: 65, SEQ ID NO: 66, SEQ ID NO: 68, SEQ ID NO: 70, SEQ ID NO: 73, SEQ ID NO: 74, SEQ ID NO: 75, SEQ ID NO: 82, SEQ ID NO: 83, SEQ ID NO: 87, SEQ ID NO: 88, SEQ ID NO: 89, SEQ ID NO: 91, SEQ ID NO: 93, SEQ ID NO: 95, SEQ ID NO: 96, SEQ ID NO: 98, SEQ ID NO: 102, SEQ ID NO: 109, SEQ ID NO: 110, SEQ ID NO: 111, SEQ ID NO: 112, SEQ ID NO: 113, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 123, SEQ ID NO: 127, SEQ ID NO: 128, SEQ ID NO: 130, SEQ ID NO: 132, SEQ ID NO: 133, SEQ ID NO: 134, SEQ ID NO: 135, SEQ ID NO: 136, SEQ ID NO: 142, SEQ ID NO: 143, SEQ ID NO: 144, SEQ ID NO: 145, SEQ ID NO: 147, SEQ ID NO: 148, SEQ ID NO: 149, SEQ ID NO: 153, SEQ ID NO: 154, SEQ ID NO: 155, SEQ ID NO: 157, SEQ ID NO: 158, SEQ ID NO: 164, SEQ ID NO: 165, SEQ ID NO: 166, SEQ ID NO: 167, SEQ ID NO: 170, SEQ ID NO: 171, SEQ ID NO: 172, SEQ ID NO: 173, SEQ ID NO: 175, SEQ ID NO: 176, SEQ ID NO: 177, SEQ ID NO:178, and SEQ ID NO:179.

The invention claimed is:

1. A composition comprising a peptide having anti-inflammatory activity, wherein the peptide consists of the amino acid sequence of SEQ ID NO: 108.

2. The composition according to claim 1, which the peptide originates from human telomerase.

3. An anti-inflammatory composition comprising the peptide according to claim 1 as an active ingredient.

4. The anti-inflammatory composition according to claim 3 for treatment of inflammatory diseases, wherein the inflammatory disease is a central or peripheral nervous system related disease.

5. The anti-inflammatory composition according to claim 3, which is a pharmaceutical composition for treatment of inflammatory diseases, wherein the inflammatory disease is a central or peripheral nervous system related disease.

6. The anti-inflammatory composition according to claim 5, wherein the central or peripheral nervous system related diseases is selected from the group consisting of Alzheimer's disease, meningitis, encephalitis, multiple sclerosis, cerebral infarction, cerebral embolism, Guillain-Barre syndrome, neuritis, and uveitis.

7. A method for treating inflammatory diseases by administering the composition according to claim 1, wherein the inflammatory disease is a central or peripheral nervous system related disease selected from the group consisting of Alzheimer's disease, meningitis, encephalitis, multiple sclerosis, cerebral infarction, cerebral embolism, Guillain-Barre syndrome, neuritis and uveitis.

* * * * *